United States Patent [19]
Hall et al.

[11] Patent Number: 5,591,605
[45] Date of Patent: *Jan. 7, 1997

[54] PLANT STRUCTURAL GENE EXPRESSION

[75] Inventors: Timothy C. Hall, College Station, Tex.; John D. Kemp, Las Cruces, N.M.; Jerry L. Slightom, Kalamazoo, Mich.; Dennis W. Sutton, Las Cruces, N.M.

[73] Assignee: Mycogen Plant Science, Inc., San Diego, Calif.

[*] Notice: The term of this patent shall not extend beyond the expiration date of Pat. No. 5,102,746.

[21] Appl. No.: 296,073

[22] Filed: Aug. 24, 1994

Related U.S. Application Data

[63] Continuation of Ser. No. 32,826, Mar. 17, 1993, abandoned, which is a continuation of Ser. No. 741,034, Aug. 6, 1991, abandoned, which is a continuation of Ser. No. 144,775, Jan. 20, 1988, Pat. No. 5,102,796, which is a continuation of Ser. No. 485,614, Apr. 15, 1983, abandoned.

[51] Int. Cl.⁶ .......................... C12N 15/29; C12N 15/84; A01H 5/00; A01H 5/10
[52] U.S. Cl. .................. 435/70.1; 435/69.1; 435/172.3; 435/240.4; 435/320.1; 800/205; 800/255; 800/DIG. 11; 800/DIG. 23; 800/DIG. 40; 536/23.6; 536/24.1
[58] Field of Search ................................. 435/69.1, 70.1, 435/172.3, 240.4, 320.1; 800/205, 255, DIG. 11, 23, 40; 536/24.1, 23.6

[56] References Cited

U.S. PATENT DOCUMENTS

| | | | |
|---|---|---|---|
| 4,418,149 | 11/1983 | Ptashne et al. | |
| 4,536,475 | 8/1985 | Anderson | 435/172.3 |
| 5,102,796 | 4/1992 | Hall et al. | 435/172.3 |

FOREIGN PATENT DOCUMENTS

| | | |
|---|---|---|
| 0140504 | 5/1985 | European Pat. Off. |
| 8402913 | 8/1984 | WIPO |
| 8402919 | 8/1984 | WIPO |
| 8402920 | 8/1984 | WIPO |

OTHER PUBLICATIONS

O'Hare et al, PNAS 78:1527–1531 (1981).
Otten et al, Mol. Gen. Genet. vol. 183 pp. 209–213 (1981).
Chilton et al, Stadler Symp. vol. 13 pp. 39–52 (1981).
Chilton, Genetic Engineering of Osmonegulation edited by Rains et al, Plenum Pub Corp pp. 23–31 (1980).
Almad et al, The Fifteenth Miami Winter Symposium pp. 14, 15 & 17 Jan. 17–21 1983.
Barton et al, Cell 32:1033–1043 (1983).
Bevan et al, Ann. Rev. Genet. 16:357–384 (1982).
Marx, Science 219: 803 (1983).
Merlo, Adv. Plant Pathol. 1:139–178 (1982).
Leemans et al, Molecular Biology of Plant Tumors edited by Kahl et al pp. 537–545 (1982).
Montagu et al, Plasmids of Medical Environmental and Commercial Importance edited by Timmis et al pp. 71–95 (1979).
Brinster et al, Cell vol. 27 pp. 223–231 Nov. 1981.
Sun et al, Nature vol. 289 pp. 37–41 Jan. 1981.
Ream et al, Science 218:854–859 (1982).

(List continued on next page.)

*Primary Examiner*—David T. Fox
*Attorney, Agent, or Firm*—Saliwanchik & Saliwanchik

[57] ABSTRACT

The invention provides genetically modified plant cells having a plant structural gene introduced and expressed therein under the control of a T-DNA promoter. In particular, the invention provides genetically modified plant cells having the phaseolin gene introduced and expressed therein under the control of a T-DNA promoter. Also provided are novel strains of bacteria containing and replicating T-DNA which has been modified to contain an inserted plant structural gene under the control of a T-DNA promoter. Further, the invention provides novel plasmids having the ability to replicate in *E. coli* and comprising T-DNA which has been modified to contain an inserted plant structural gene under the control of a T-DNA promoter.

58 Claims, 35 Drawing Sheets

OTHER PUBLICATIONS

Fink, M. S. Thesis University of Wisconsin—Madison 1982.
Slightom et al, PNAS 80:1897–1901 (1983).
Colbene—Garapin et al, J. Mol. Biol 150:1–14 (1981).
Joos, H. (1983) Cell 32:1057–1068.
Herrera–Estrella et al. (1983) Nature 303:209–213.
Banker et al, Plant Molecular Biology vol. 2 pp. 335–350 (1983).
Fraley et al., (1983) Proc. Natl. Acad. Sci. USA 80:4803–4807.
Velten et al., (1984) EMBO J. 3:2723–2730.
*Abstracts: First International Congress of Plant Molecular Biology*, p. 115, PO–1–270 (Galau ed. 1985).
DeGreve et al., (1982) J. Mol. & Appl. Genet. 1:499–511.
Depicker et al., (1982) J. Mol. & Appl. Genet. 1:561–573.
Daese et al., (1983) EMBO J. 2:419–426.
Gelvin et al., (1982) Proc. Nat. Acad. Sci. USA 79:76–80.
Holsters et al., (1982) Molec. Gen. Genet. 185:283–289.
Garfinkle et al., (1981) Cell 27:143–153.
Proceedings of 15th Miami Winter Symposium, (1984).
*Biotechnology News*, p. 1 (Feb. 1, 1983);.
*Agricultural Genetics Reports*, pp. 1–2 (Jan./Feb. 1983);.
*Genetic Technology News*, pp. 5–6 (Mar. 1983);.
*Genetic Engineering Letter*, p. 1 (Jan. 24, 1983);.
*Genetic Technology News*, p. 1 (Feb. 1983);.
Gamborg, "Somatic Cell Hybridization by Protoplast Fusion and Morphogenesis," in *Plant Tissue Culture and Its Bio-Technological Application*, pp. 287–301 (Barz et al., eds. 1977).

Burr & Burr, (1982) Cell 29:977–986.
Hernalsteens et al., (1980) Nature 287:654–656.
*Advances in Gene Technology: Molecular Genetics of Plants and Animals* (F. Ahmad, K. Downey, J. Schultz & R. Voellmy, eds. 1983).
*Plant Molecular Biology Newsletter: Conference Abstract Issue* (1983).
Schell et al. (1983) Bio/technology 1:175–180.
*The Wall Street Journal*, p. 12 (Jan. 20, 1983); and.
*The Washington Post*, p. A5 (Jan. 19, 1983).
Otten et al. 1981. Mol. Gen. Genet. 183:209–213.
Wullems et al. 1981. Cell 24:719–727.
Horsch et al. 1984. Science 223:496–498.
DeGreve et al. 1982. Nature 300:752–755.
Leemans et al., 1982. pp. 537–545 In: Molec. Bid. Plant Tumors, Kahl et al., eds., Academic Press: New York.
Goodman et al. 1982 Science 236:48–54.
Fraley et al. 1983. Proc. Natl. Acad. Sci. USA 80:4803–4807.
Knopf, U. 1974. Sub. Cell. Biochem. 3:39–48.
Lippincott et al. 1978. Science 199:1075–1078.
Hernalsteens et al. 1984. EMBO J 3(13): 3039–3041.
DeCleene et al. 1976. Botanical Review 42(4): 389–466.
de Framond et al. 1983. Adv. Gene Technol., Academic Press, Inc., pp. 159–169.
Green et al. 1983. Adv. Gene Technol., Academic Press, Inc., pp. 147–157.

T-DNA REGION OF pTi15955

FIG. 2A

```
AGAAACATGAACCATCGCTACCTTAGTGAGGACGTGAAGCACATTTTGGTGCTCTGGGTTGAGATAGCTGAAGTGATCGGCGTGCAAGTTCCAGAAATGA
----+----|----+----|----+----|----+----|----+----|----+----|----+----|----+----|----+----|----+----|  1100
ArgAsnMetAsnHisArgTyrLeuSerGluAspValLysHisIleLeuValLeuTrpValGluIleAlaGluValIleGlyValGlnValProGluMetL

AATCTGTAGTGCAGGAGGCAAGCGACGTGCTGAACGAGGACCTCTCTCATACTGGTAGGGGCTATCGTCTCAACCTGGAAGGTTCAAACGCGAATGC
----+----|----+----|----+----|----+----|----+----|----+----|----+----|----+----|----+----|----+----|  1200
ysSerValValGlnGluAlaSerAspValLeuAsnGluAspLeuSerHisThrGlyArgGlyLeuSerLeuGluGlyIleArgLeuGlnThrArgMetAl

CATAGTCAGGGCTCTCAATGGAGTTTGAATCAAATCTTCCAGTCGCTTTAATGAGATATGCGAGACGCCTATGATCGCATGATATTTGCTTTCAATTCTG
----+----|----+----|----+----|----+----|----+----|----+----|----+----|----+----|----+----|----+----|  1300
aIleValArgAlaLeuAsnGlyValEnd

TTGTGCACGTTGTAAAAAAACCTGAGACATGTGTAGCTCAGATCCTTACCGCCGGTTTCATTCTAATGAATATATCACCCGTTACTATCGTATTTT
----+----|----+----|----+----|----+----|----+----|----+----|----+----|----+----|----+----|----+----|  1400
```

```
177.4   CAATTTCTCTCCAAATGTGATGATAAATGTTTGTCCTGTAGGAATTTTTCCTATCTAGCACAGAAGCCCAACAATCTACTTGCAAGAGTTCAGCAAGCA       800
cDNA31  ------------------------------------------------------------------------------------------------
                                              GAATTTTTCCTATCTAGCACAGAAGCCCAACAATCTACTTGCAAGAGTTCAGCAAGCA
                                              GluPhePheLeuSerSerThrGluAlaGlnGlnSerTyrLeuGlnGluPheSerLysHi 177.4   TATTCTAGAGGCCTCCTTCAATGTAAGAAAAGAAAACAGCATCTAACTACATATTTGCGTTGCCATTTAGCTAGTACTTTGTCTAAATGTCACACTTGTTG     900
cDNA31  ------------------------------------------------------------------------------------------
        TATTCTAGAGGCCTCCTTCAAT                                                                    (IVS 3, 124 bp)
        sIleLeuGluAlaSerPheAsn 177.4   AATTTGTTGAATGATATCATTATATATGTTTGCATGATTTTTATAGAGCAAATTCGAGGAGATCAACAGGGTTCTCTGTTTGAAGAGAGGAGGACAGCAAGAG    1000
cDNA31  ------------------------------------------------------------------------------------------
                                              AGCAAATTCGAGGAGATCAACAGGGTTCTCTGTTTGAAGAGAGGAGGACAGCAAGAG
                                              SerLysPheGluGluIleAsnArgValLeuPheGluGluGluGluGlyGlyGlnGlnGlu 177.4   GGAGTGATTGTGAACATTGATTCTGAACAGATTAAGGAACTGAGCAAACATGCAAAATCTAGTTCAAGGAAATCCCTTTCCAAACAAGATAACACAATTG      1100
cDNA31  GGAGTGATTGTGAACATTGATTCTGAACAGATTAAGGAACTGAGCAAACATGCAAAATCTAGTTCAAGGAAATCCCTTTCCAAACAAGATAACACAATTG
        GlyValIleValAsnIleAspSerGluGlnIleLysGluLeuSerLysHisAlaLysSerSerSerArgLysSerLeuSerLysGlnAspAsnThrIleG 177.4   GAAACGAATTTGGAAACCTGACTGAGAGGACCGATAACTCCTGAATGTGTTAATCAGTTGTTCTATAGAGATGGAAGAGGTAAATACAAAGAAAAACCATAT    1200
cDNA31  GAAACGAATTTGGAAACCTGACTGAGAGGACCGATAACTCCTGAATGTGTTAATCAGTTGTTCTATAGAGATGGAAGAGGTAAATACAAAGAAAAACCATAT
        lyAsnGluPheGlyAsnLeuThrGluArgThrAspAsnSerLeuAsnValLeuIleSerSerIleGluMetGluGlu 177.4   AGACAAACTCAGCAATTGAGTTCTATTATTCACTGTCGTCTTGGTTAGAAAATCTTAGTATTGAGACTATAATTAAATAATGGTTTTTTTGTTAACAAA      1300
cDNA31  ------------------------------------------------------------------------------------------
                                                              (IVS 4, 128 bp)

177.4   TTTAGGGAGCTCTTTTTGTGCCACACTGAGTTCTAAGGCCATTGTTATACTAGTGGTTAATGAAGGAGAAGCACATGTTGAACTTGTTGGCCCAAAAGG      1400
cDNA31  GGAGCTCTTTTTGTGCCACACTGAGTTCTAAGGCCATTGTTATACTAGTGGTTAATGAAGGAGAAGCACATGTTGAACTTGTTGGCCCAAAAGG
        GlyAlaLeuPheValPheHisTyrTyrSerLysAlaIleValIleLeuValAsnGluGlyGluAlaHisValGluLeuValGlyProLysGl 177.4   AAATAAGGAAACCTTGGAATATGAGAGCTACAGAGCTGAGCTTTCTAAAGACGATGTATTTGTAATCCCAGCAGCATATCCAGTTGCCATCAAGGCTACC     1500
cDNA31  AAATAAGGAAACCTTGGAATATGAGAGCTACAGAGCTGAGCTTTCTAAAGACGATGTATTTGTAATCCCAGCAGCATATCCAGTTGCCATCAAGGCTACC
```

```
TGATAGTTTAAACCGAAGGCGGGAAACGACAATCTGATCATGAGCGGAGAATTAAGGGAGTCACGTTATGACCCCGCCGATGACGCGGGACAAGCCGTT      100
----+----|----+----|----+----|----+----|----+----|----+----|----+----|----+----|----+----|----+----|

TTACGTTTGGAACTGACAGAACCGCAACGTTGAAGGAGCCACTGAGCCGGGTTTCTGGAGTTTAATGAGCTAAGCACATACGTCAGAAACCATTATTG       200
----+----|----+----|----+----|----+----|----+----|----+----|----+----|----+----|----+----|----+----|

CGGCTTCAAAAGTCGCCTAAGGTCACTATCAGCTAGCAAATATTCTTGTCAAAAATGCTCCACTGACGTTCCATAAATTCCCCTCGGTATCCAATTAGA    300
----+----|----+----|----+----|----+----|----+----|----+----|----+----|----+----|----+----|----+----|

GTCTCATATTCACTCTCAATCCAAATAATCTGCAATGGCAATTACCTTATCCGCAACTTCTTTACCTATTTCCGCCAGATCACCATCCGCTTCCCTTG     400
----+----|----+----|----+----|----+----|----+----|----+----|----+----|----+----|----+----|----+----|
                       MetAlaIleThrLeuSerAlaThrSerLeuProIleSerAlaAlaAspHisHisProLeuProLeu

ACCGTAGGTGTCCTCGGTTCTGGTCACGGCTTGGTTCGCCTGGGGACTGCATTAGCGGGCTTCCCACGGCGCTGTGGGCACCAGATCATC            500
----+----|----+----|----+----|----+----|----+----|----+----|----+----|----+----|----+----|----+----|
ThrValGlyValLeuGlySerGlyHisGlyLeuValLeuAlaLeuAlaAlaTrpPheAlaSerArgHisValProThrAlaLeuTrpAlaProAlaAspHisP

CAGGATCGATCTCAGCAATCAAGGCCAGTGATTGAAGGAGTTATCACCACCGAGGGAATGATTAACGGTCCATTTAGGGTCTCAGCCTGTGATGACCTTGCCGC   600
----+----|----+----|----+----|----+----|----+----|----+----|----+----|----+----|----+----|----+----|
roGlySerIleSerAlaIleIleLysAlaSerGluGlyValIleThrThrGluGlyMetIleAsnGlyProPheArgValSerAlaCysAspLeuAlaAl

AGTTATTCGCTCCAGCCGTGTACTGATTATTGTAACCCGTGCGGGACGTTCACGACAGCTTCGTCAACGACAGCTTCAACGGCGAACTGCAACA            700
----+----|----+----|----+----|----+----|----+----|----+----|----+----|----+----|----+----|----+----|
aValIleArgSerSerArgValLeuIleIleValThrArgAlaAspValHisAspSerPheValAsnGluLeuAlaAsnPheAsnGlyGluLeuAlaThr

AAGGATATTGTCGTGTGCGGCCATGGCTTCTCCATCAAGTACGAGAGACAGCTGCGATTCAAGGACAGCTGCGAATATTCGAGAGCGGATAATTCGCCATAACGT  800
----+----|----+----|----+----|----+----|----+----|----+----|----+----|----+----|----+----|----+----|
LysAspIleValValCysGlyHisGlyPheSerIleLysTyrGluLysIleLysAlaSerPheGluThrAspAsnSerProIleThrS

CTAAGCTATCGGATCAAAAAAAATGTAACGTCAACATCAAGGAAATGAAAGCGTCTTTCGGACTGTCTCATGTTCCCAATTCATCGCGATGATGCTGGCGT     900
----+----|----+----|----+----|----+----|----+----|----+----|----+----|----+----|----+----|----+----|
erLysLeuSerAspAspProGlnLysLysCysAsnValAsnIleLysGluMetLysAlaSerPheGlyLeuSerCysPheProIleHisArgAspAspAlaGlyVa

GATTGATCTACCCGAAGATACCAAGAGAACATCTTTGCCCAGCTATTTTCCGCTAGAATCATCTGCAAGTGCTATTCTTTTCCAACTAT               1000
----+----|----+----|----+----|----+----|----+----|----+----|----+----|----+----|----+----|----+----|
lIleAspLeuProGluAspThrLysAsnIlePheAlaGlnLeuPheSerAlaArgIleIleCysIleProProLeuProLeuGlnValLeuPheSerAsnTyr
```

FIG. 4A

```
ATCACTCATGCGGTTCCGGCAGTCATGAACATCGGAAGACTCCGGACCAGCCAATTCTCTTACTAAAAGAGCTGAGAAGTGGCTTCTTGAACTAGACG      1100
---+---------+---------+---------+---------+---------+---------+---------+---------+---------+---
IleThrHisAlaValProAlaValMetAsnIleGlyArgLeuArgAspProAlaAsnSerLeuThrLysArgAlaGluLysTrpLeuLeuGluLeuAspG

AGCGAACCCCACGAGCCGAGAAGGGCTTTTCTTTTATGGTGAAGGATCCAACACTTACGTTGCAACGTCCAAGAGCAAATAGACCACGAACGCCGGAA      1200
---+---------+---------+---------+---------+---------+---------+---------+---------+---------+---
luArgThrProArgAlaGluLysGlyPhePheTyrGlyGluGlySerAsnThrTyrValCysAsnValGlnGluGlnIleAspHisGluArgArgLy

GGTTGCCGCAGGTGTGGACTGCTCTCAATTCTCTTCTGCAGGAATGCAATGATACTGACTATGAAACTTTGAGGGAATACTGCCTAGCA      1300
---+---------+---------+---------+---------+---------+---------+---------+---------+---------+---
sValAlaAlaAlaCysGlyLeuLeuArgLeuAsnSerLeuLeuGlnGluLeuAsnAspGluTyrAspThrAspTyrGluThrLeuArgGluTyrCysLeuAla

CCGTCACCTCATAACGTGCATCATGCCCTGACAACATCGGCTATTTTTCTGAAGAATTATGCTCGTTGGAGGATGTCGCGGCAATTGCAG      1400
---+---------+---------+---------+---------+---------+---------+---------+---------+---------+---
ProSerProHisAsnValHisHisAlaCysProAspAsnMetGluHisArgTyrPheSerGluGluLeuCysSerLeuGluAspValAlaAlaIleAlaA

CTATTGCCAAAATGAAATCCCTCACGCATGCATTCAATATTATTCATGCGGGGAAAGGCAAGATTAATCCAACTGGCAAATCATCCAGCGTGAT      1500
---+---------+---------+---------+---------+---------+---------+---------+---------+---------+---
laIleAlaLysIleGluIleProLeuThrHisAlaPheIleAsnIleIleHisAlaGlyLysGlyLysIleAsnProThrGlyLysSerSerSerValIl

TGGTAACTTCAGTTCCAGCGACTTGATTCGTTTTGGTGCTACCCACGTTTCAATAAGGACGAGATGGTGGAGTAAAGAAGGAGTGCGTCGAAGCAGATC      1600
---+---------+---------+---------+---------+---------+---------+---------+---------+---------+---
eGlyAsnPheSerSerSerAspLeuIleArgPheGlyAlaThrHisValPheAsnLysAspGluMetValGluEnd

GTTCAAACATTTGGCAATAAAGTTTCTTAAGATTGAATCCTGTTGCCGATGATTATCATATAATTTCTGTTGAATTACGTTAAGCATGTAAT      1700
---+---------+---------+---------+---------+---------+---------+---------+---------+---------+---

AATTAACATGTAATGCATGACGTTATTTATGAGATGGGTTTTTATGATTAGAGTCCCGCAATTATACATTTAATACGCGATAGAAAACAAAATATAGCGC      1800
---+---------+---------+---------+---------+---------+---------+---------+---------+---------+---
```

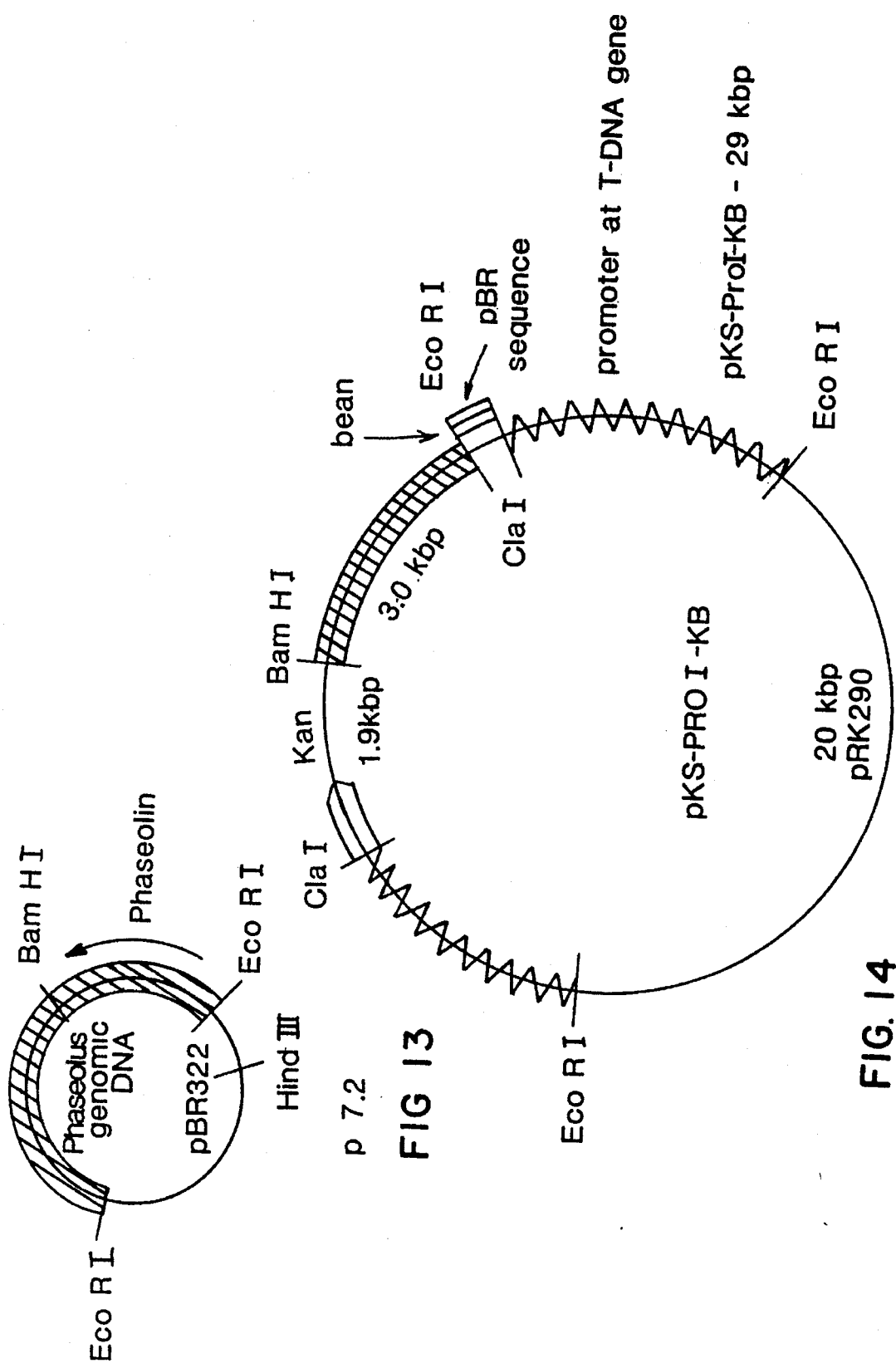

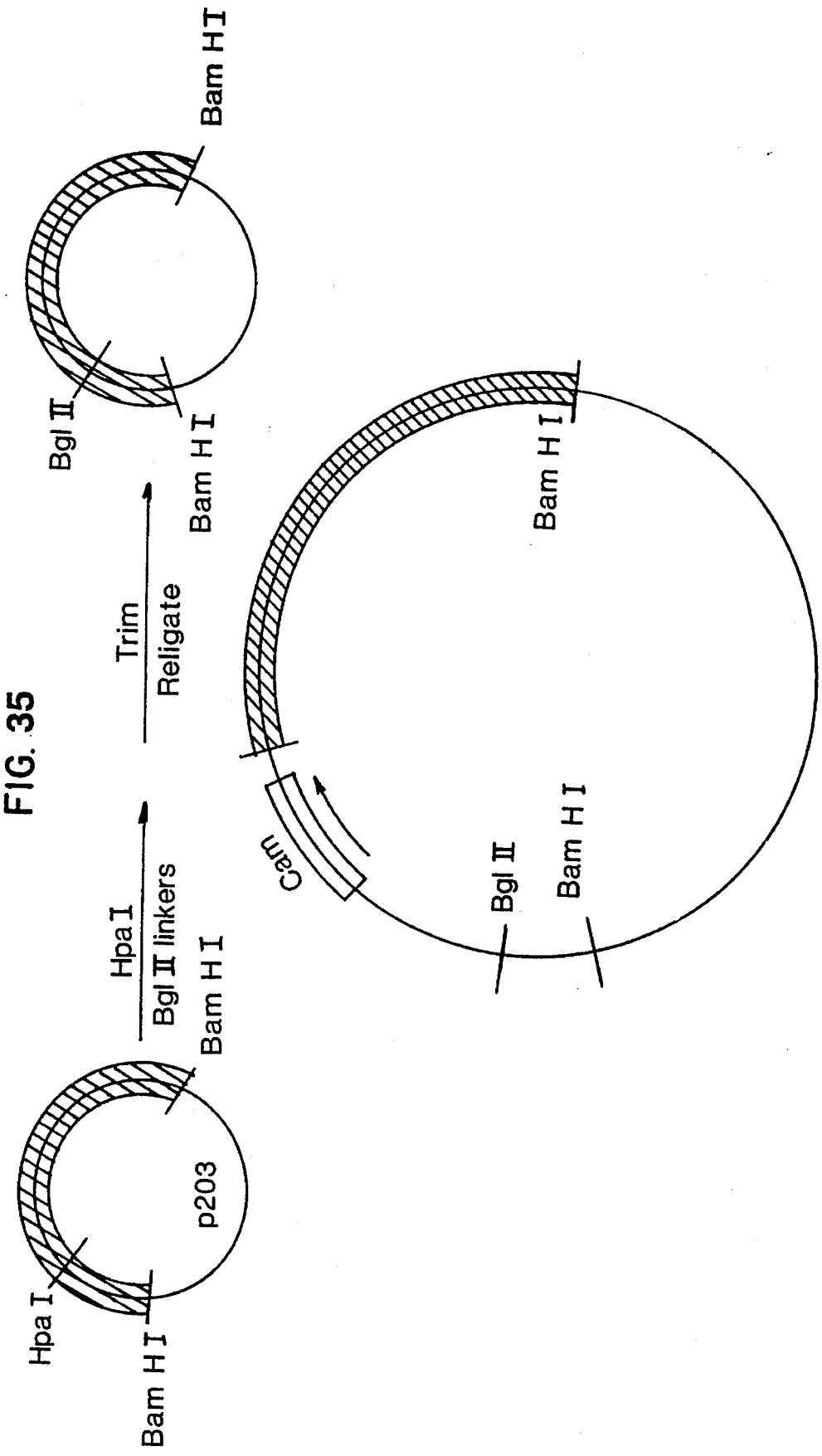

FIG. 38

PLANT STRUCTURAL GENE EXPRESSION

This application is a continuation of application Ser. No. 08/032,826, filed Mar. 17, 1993, now abandoned, which is a continuation of application Ser. No. 07/741,034, filed 6 Aug. 1991, now abandoned, which is a continuation of application Ser. No. 07/144,775, filed 20 Jan. 1988, now U.S. Pat. No. 5,102,796, which is a continuation of application Ser. No. 06/485,614, filed 15 Apr. 1983, now abandoned.

BACKGROUND

Shuttle Vectors

Shuttle vectors, developed by Ruvkun and Ausubel (1981) Nature 289:85–88, provide a way to insert foreign genetic materials into a position of choice in a large plasmid, virus, or genome. There are two main problems encountered when dealing with large plasmids or genomes. Firstly, the large plasmids may have many sites for each restriction enzyme. Unique, site-specific cleavage reactions are not reproducible and multi-site cleavage reactions followed by ligation lead to great difficulties due to the scrambling of the many fragments whose order and orientation one does not want changed. Secondly, the transformation efficiency with large DNA plasmids is very low. Shuttle vectors allow one to overcome these difficulties by facilitating the insertion, often in vitro, of the foreign genetic material into a smaller plasmid, then transferring, usually by in vivo techniques, to the larger plasmid.

A shuttle vector consists of a DNA molecule, usually a plasmid, capable of being introduced into the ultimate recipient bacteria. It also includes a copy of the fragment of the recipient genome into which the foreign genetic material is to be inserted and a DNA segment coding for a selectable trait, which is also inserted into the recipient genome fragment. The selectable trait ("marker") is conveniently inserted by transposon mutagenesis or by restriction enzymes and ligases.

The shuttle vector can be introduced into the ultimate recipient cell typically a bacterium of the genus Agrobacterium by a tri-parental mating (Ruvkun and Ausubel, supra), direct transfer of a self-mobilizable vector in a bi-parental mating, direct uptake of exogenous DNA by Agrobacterium cells ("transformation", using the conditions of M. Holsters et al. (1978) Molec. Gen. Genet. 163:181–187), by spheroplast fusion of Agrobacterium with another bacterial cell, by uptake of liposome-encapsulated DNA, or infection with a shuttle vector that is based on a virus that is capable of being packaged in vitro. A tri-parental mating involves the mating of a strain containing a mobilizable plasmid, which carries genes for plasmid mobilization and conjugative transfer, with the strain containing the shuttle vector. If the shuttle vector is capable of being mobilized by the plasmid genes, the shuttle vector is transferred to the recipient cell containing the large genome, e.g., the Ti or Ri plasmids of Agrobacterium strains.

After the shuttle vector is introduced into the recipient cell, possible events include a double cross over with one recombinational event on either side of the marker. This event will result in transfer of a DNA segment containing the marker to the recipient genome replacing a homologous segment lacking the insert. To select for cells that have lost the original shuttle vector, the shuttle vector must be incapable of replicating in the ultimate host cell or be incompatible with an independently selectable plasmid preexisting in the recipient cell. One common means of arranging this is to provide in the third parent another plasmid which is incompatible with the shuttle vector and which carries a different drug resistance marker. Therefore, when one selects for resistance to both drugs, the only surviving cells are those in which the marker on the shuttle vector has recombined with the recipient genome. If the shuttle vector carries an extra marker, one can then screen for and discard cells that are the result of a single cross-over between the shuttle vector and the recipient plasmid, resulting in cointegrates in which the entire shuttle vector is integrated with the recipient plasmid. If the foreign genetic material is inserted into or adjacent to the marker that is selected for, it will also be integrated into the recipient plasmid as a result of the same double recombination. It might also be carried along when inserted into the homologous fragment at a spot not within or adjacent to the marker, but the greater the distance separating the foreign genetic material from the marker, the more likely will be a recombinational event occurring between the foreign genetic material and marker, preventing transfer of the foreign genetic material.

Shuttle vectors have proved useful in manipulation of Agrobacterium plasmids: see D. J. Garfinkel et al. (1981) Cell 27:143–153, A. J. M. Matzke and M. D. Chilton (1981) J. Molec. Appl. Genet. 1:39–49, and J. Leemans et al. (1981) J. Molec. Appl. Genet. 1:149–164, who referred to shuttle vectors by the term "intermediate vectors".

Agrobacterium—Overview

Included within the gram-negative bacterial family Rhizobiaceae in the genus Agrobacterium are the species *A. tumefaciens* and *A. rhizogenes*. These species are respectively the causal agents of crown gall disease and hairy root disease of plants. Crown gall is characterized by the growth of a gall of dedifferentiated tissue. Hairy root is a teratoma characterized by inappropriate induction of roots in infected tissue. In both diseases, the inappropriately growing plant tissue usually produces one or more amino acid derivatives, known as opines, not normally produced by the plant which are catabolized by the infecting bacteria. Known opines have been classified into three families whose type members are octopine, nopaline, and agropine. The cells of inappropriately growing tissues can be grown in culture, and, under appropriate conditions, be regenerated into whole plants that retain certain transformed phenotypes.

Virulent strains of Agrobacterium harbor large plasmids known as Ti (tumor-inducing) plasmids in *A. tumefaciens* and Ri (root-inducing) plasmids in *A. rhizogenes*. Curing a strain of these plasmids results in a loss of pathogenicity. The Ti plasmid contains a region, referred to as T-DNA (transferred-DNA), which in tumors is found to be integrated into the genome of the host plant. The T-DNA encodes several transcripts. Mutational studies have shown that some of these are involved in induction of tumorous growth. Mutants in the genes for tml, tmr, and tms, respectively, result in large tumors (in tobacco), a propensity to generate roots, and a tendency for shoot induction. The T-DNA also encodes the gene for at least one opine synthase, and the Ti plasmids are often classified by the opine which they caused to be synthesized. Each of the T-DNA genes is under control of a T-DNA promoter. The T-DNA promoters resemble eukaryotic promoters in structure, and they appear to function only in the transformed plant cell. The Ti plasmid also carries genes outside the T-DNA region. These genes are involved in functions which include opine catabolism, oncogenicity, agrocin sensitivity, replication, and autotransfer to plant cells. The Ri plasmid is organized in a fashion analogous to the Ti plasmid. The set of genes and DNA sequences responsible for transforming the plant cell are hereinafter collectively referred to as the transformation-inducing principle (TIP). The designation TIP therefore includes both Ti and Ri plasmids. The integrated segment of a TIP is termed herein "T-DNA", whether derived from a Ti plasmid or an Ri plasmid. Recent general reviews of Agrobacterium-caused disease include those by D. J. Merlo (1982), Adv. Plant Pathol. 1:139–178 L. W. Ream and M. P. Gordon (1982), Science 218:854–859, and M. W. Bevan and M. D. Chilton (1982), Ann. Rev. Genet. 16:357–384; G. Kahl and J. Schell (1982) *Molecular Biology of Plant Tumors*.

Agrobacterium—Infection of Plant Tissues

Plant cells can be transformed by Agrobacterium in a number of methods known in the art which include but are not limited to co-cultivation of plant cells in culture with Agrobacterium, direct infection of a plant, fusion of plant protoplasts with Agrobacterium spheroplasts, direct transformation by uptake of free DNA by plant cell protoplasts, transformation of protoplasts having partly regenerated cell walls with intact bacteria, transformation of protoplasts by liposomes containing T-DNA, use of a virus to carry in the T-DNA, microinjection, and the like. Any method will suffice as long as the gene is reliably expressed, and is stably transmitted through mitosis and meiosis.

The infection of plant tissue by Agrobacterium is a simple technique well known to those skilled in the art (for an example, see D. N. Butcher et al. (1980) in *Tissue Culture Methods for Plant Pathologists*, eds.: D. S. Ingrams and J. P. Helgeson, pp. 203–208). Typically a plant is wounded by any of a number of ways, which include cutting with a razor, puncturing with a needle, or rubbing with abrasive. The wound is then inoculated with a solution containing tumor-inducing bacteria. An alternative to the infection of intact plants is the inoculation of pieces of tissues such as potato tuber disks (D. K. Anand and G. T. Heberlein (1977) Amer. J. Bot. 64:153–158) or segments of tobacco stems (K. A. Barton et al. (1983) Cell 30:589–597). After induction, the tumors can be placed in tissue culture on media lacking phytohormones. Hormone independent growth is typical of transformed plant tissue and is in great contrast to the usual conditions of growth of such tissue in culture (A. C. Braun (1956) Cancer Res. 16:3–56).

Agrobacterium is also capable of infecting isolated cells and cells grown in culture, Marton et al. (1979) Nature 277:129–131, and isolated tobacco mesophyll protoplasts. In the latter technique, after allowing time for partial regeneration of new cell walls, Agrobacterium cells were added to the culture for a time and then killed by the addition of antibiotics. Only those cells exposed to *A. tumefaciens* cells harboring the Ti plasmid were capable of forming calli when plated on media lacking hormone. Most calli were found to contain an enzymatic activity involved in opine anabolism. Other workers (R. B. Horsch and R. T. Fraley (18 Jan. 1983) 15th Miami Winter Symposium) have reported transformations by co-cultivation, leading to a high rate (greater than 10%) of calli displaying hormone-independent growth, with 95% of those calli making opines. M. R. Davey et al. (1980) in Ingram and Helgeson, supra, pp. 209–219, describe the infection of older cells that had been regenerated from protoplasts.

Plant protoplasts can be transformed by the direct uptake of TIP plasmids. M. R. Davey et al. (1980) Plant Sci. Lett. 18:307–313, and M. R. Davey et al. (1980) in Ingram and Helgeson, supra, were able to transform Petunia protoplasts with the Ti plasmid in the presence of poly-L-alpha-ornithine to a phenotype of opine synthesis and hormone-independent growth in culture. It was later shown (J. Draper et al. (1982) Plant and Cell Physiol. 23:451–458, M. R. Davey et al. (1982) in *Plant Tissue Culture* 1982, ed: A. Fujiwara, pp. 515–516) that polyethylene glycol stimulated Ti uptake and that some T-DNA sequences were integrated into the genome. F. A. Krens et al. (1982) Nature 296:72–74, reported similar results using polyethylene glycol following by a calcium shock, though their data suggests that the integrated T-DNA included flanking Ti plasmid sequences.

An alternative method to obtain DNA uptake involves the use of liposomes. The preparation of DNA containing liposomes is taught by Papahadjopoulos in U.S. Pat. Nos. 4,078,052 and 4,235,871. Preparations for the introduction of Ti-DNA via liposomes have been reported (T. Nagata et al. (1982) in Fujiwara, supra, pp. 509–510, and T. Nagata (1981) Mol. Gen. Genet. 184:161–165). An analogous system involves the fusion of plant and bacterial cells after removal of their cell walls. An example of this technique is the transformation of Vinca protoplasts by Agrobacterium spheroplasts reported by S. Hasezawa et al. (1981) Mol. Gen. Genet. 182:206–210. Plant protoplasts can take up cell wall delimited Agrobacterium cells (S. Hasezawa et al. (1982) in Fujiwara, supra pp. 517–518).

T-DNA can be transmitted to tissue regenerated from a fusion of two protoplasts, only one of which had been transformed (G. J. Wullems et al. (1980) Theor. Appl. Genet. 56:203–208). As detailed in the section on Regeneration of Plants, T-DNA can pass through meiosis and be transmitted to progeny as a simple Mendelian trait.

Agrobacterium—Regeneration of Plants

Differentiated plant tissues with normal morphology have been obtained from crown gall tumors. A. C. Braun and H. N. Wood (1976) Proc. Natl. Acad. Sci. USA 73:496–500, grafted tobacco teratomas onto normal plants and were able to obtain normally appearing shoots which could flower. The shoots retained the ability to make opines and to grow independently of phytohormones when placed in culture. In the plants screened, these tumor phenotypes were not observed to be transmitted to progeny, apparently being lost during meiosis (R. Turgeon et al. (1976) Proc. Natl. Acad. Sci. USA 73:3562–3564). Plants which had spontaneously lost tumorous properties, or which were derived from teratoma seed, were initially shown to have lost all their T-DNA (F. M. Yang et al. (1980) In Vitro 16:87–92, F. Yang et al. (1980) Molec. Gen. Genet. 177:707–714, M. Lemmers et al. (1980) J. Mol. Biol. 144:353–376). However, later work with plants that had become revertants after hormone treatment (1 mg/l kinetin) showed that plants which had gone through meiosis, though losing T-DNA genes responsible for the transformed phenotype, could retain sequences homologous to both ends of T-DNA (F. Yang and R. B. Simpson (1981) Proc. Natl. Acad. Sci. USA 78:4151–4155). G. J. Wullems et al. (1981) Cell 24:719–724, further demonstrated that genes involved in opine anabolism were capable of passing through meiosis though the plants were male sterile and that seemingly unaltered T-DNA could be inherited in a Mendelian fashion (G. Wullems et al. (1982) in A. Fujiwara, supra). L. Otten et al. (1981) Molec. Gen. Genet. 183:209–213, used Tn7 transposon-generated Ti plasmid mutants in the tms (shoot-inducing) locus to create tumors which proliferated shoots. When these shoots were regenerated into plants, they were found to form self-fertile flowers. The resultant seeds germinated into plants which contained T-DNA and made opines. Similar experiments with a tmr (root-inducing) mutant showed that full-length T-DNA could be transmitted through meiosis to progeny, that in those progeny nopaline genes could be expressed, though at variable levels, and that cotransformed yeast alcohol dehydrogenase I gene was not expressed (K. A. Barton et al. (1983) supra). It now appears that regenerated tissues which lack T-DNA sequences are probably descended from untransformed cells which "contaminate" the tumor (G. Ooms et al. (1982) Cell 30:589–597).

Roots resulting from transformation from *A. rhizogenes* have proven relatively easy to regenerate into plantlets (M. D. Chilton et al. (1982) Nature 295:432–434.

Agrobacterium—Genes on the TIP Plasmids

A number of genes have been identified within the T-DNA of the TIP plasmids. About half a dozen octopine plasmid T-DNA transcripts have been mapped (S. B. Gelvin et al. (1982) Proc. Natl. Acad. Sci. USA 79:76–80, L. Willmitzer et al. (1982) EMBO J. 1:139–146) and some functions have been assigned (J. Leemans et al. (1982) EMBO J. 1:147–152). The four genes of an octopine type plasmid that have been well defined by transposon mutagenesis include tms, tmr, and tml (D. J. Garfinkel et al. (1981) Cell 27:143–153). Ti plasmids which carry mutations in these genes respectively incite tumorous calli of *Nicotiana tabacum* which generate shoots, proliferate roots, and are larger than normal. In other hosts, mutants of these genes can induce different phenotypes (see Bevan and Chilton, supra). The phenotypes of tms and tmr are correlated with differences in the phytohormone levels present in the tumor. The differences in cytokinin:auxin ratios are similar to those which in culture induce shoot or root formation in untransformed callus tissue (D. E. Akiyoshi et al. (1983) Proc. Natl. Acad. Sci. USA 80:407–411). T-DNA containing a functional gene for either tms or tmr alone, but not functional tml alone, can promote significant tumor growth. Promotion of shoots and roots is respectively stimulated and inhibited by functional tml (L. W. Ream et al. (1983) Proc. Natl. Acad. Sci. USA 80:1660–1664). Mutations in T-DNA genes do not seem to affect the insertion of T-DNA into the plant genome (J. Leemans et al. (1982) supra L. W. Ream et al. (1983) supra). The ocs gene encodes octopine synthase, which has been sequenced by H. De Greve et al. (1982) J. Mol. Appl. Genet. 1:499–511. It does not contain introns (intervening sequences commonly found in eukaryotic genes which are posttranscriptionally spliced out of the messenger precursor during maturation of the mRNA). It does have sequences that resemble a eukaryotic transcriptional signal ("TATA box") and a polyadenylation site. As plant cells containing the enzyme octopine synthase detoxify homo-arginine, the ocs gene may prove to be a useful selectable marker for plant cells that have been transformed by foreign DNA (G. M. S. Van Slogteren et al. (1982) Plant Mol. Biol. 1:133–142).

Nopaline Ti plasmids encode the nopaline synthase gene (nos), which has been sequenced by A. Depicker et al. (1982) J. Mol. Appl. Genet. 1:561–573. As was found with the ocs gene, nos is not interrupted by introns. It has two putative polyadenylation sites and a potential "TATA box". In contrast to ocs, nos is preceded by a sequence which may be a transcriptional signal known as a "CAT box". J. C. McPhersson et al. (1980) Proc. Natl. Acad. Sci. USA 77:2666–2670, reported the in vitro translation of T-DNA encoded mRNAs from crown gall tissues.

Transcription from hairy root T-DNA has also been detected (L. Willmitzer et al. (1982) Nol. Gen. Genet. 186:16–22). Functionally, the hairy root syndrome appears to be equivalent of a crown gall tumor incited by a Ti plasmid mutated in tmr (F. F. White and E. W. Nester (1980) J. Bacteriol. 144:710–720).

In eukaryotes, methylation (especially of cytosine residues) of DNA is correlated with transcriptional inactivation; genes that are relatively undermethylated are transcribed into mRNA. Gelvin et al. (1983) Nucleic Acids Res. 1:159–174, have found that the T-DNA in crown gall tumors is always present in at least one unmethylated copy. That the same genome may contain numerous other copies of T-DNA which are methylated suggests that the copies of T-DNA in excess of one may be biologically inert. (See also G. Ooms et al. (1982) Cell 30:589–597.)

The Ti plasmid encodes other genes which are outside of the T-DNA region and are necessary for the infection process. (See M. Holsters et al. (1980) Plasmid 3:212–230 for nopaline plasmids, and H. De Greve et al. (1981) Plasmid 6:235–248, D. J. Garfinkel and E. W. Nester (1980) J. Bacteriol 144:732–743, and G. Ooms (1980) J. Bacteriol 144:82–91 for octopine plasmids). Most important are the onc genes, which when mutated result in Ti plasmids incapable of oncogenicity. (These loci are also known as vir, for virulence.) The onc genes function in trans, being capable of causing the transformation of plant cells with T-DNA of a different plasmid type and physically located on another plasmid (J. Hille et al. (1982) Plasmid 7:107–118, H. J. Klee et al. (1982) J. Bacteriol 150:327–331, M. D. Chilton (18 Jan. 1983) 15th Miami Winter Symp.). Nopaline Ti DNA has direct repeats of about 25 base pairs immediately adjacent to the left and right borders of the T-DNA which might be involved in either excision from the Ti plasmid or integration into the host genome (N. S. Yadav et al. (1982) Proc. Natl. Acad. Sci. USA 79:6322–6326), and a homologous sequence has been observed adjacent to an octopine T-DNA border (R. B. Simpson et al. (1982) Cell 29:1005–1014). Opine catabolism is specified by the occ and noc genes, respectively of octopine- and nopaline-type plasmids. The Ti plasmid also encodes functions necessary for its own reproduction including an origin of replication. Ti plasmid transcripts have been detected in *A. tumefaciens* cells by S. B. Gelvin et al. (1981) Plasmid 6:17–29, who found that T-DNA regions were weakly transcribed along with non-T-DNA sequences. Ti plasmid-determined characteristics have been reviewed by Merlo, supra (see especially Table II), and Ream and Gordon surpa.

Agrobacterium—TIP Plasmid DNA

Different octopine-type Ti plasmids are nearly 100% homologous to each other when examined by DNA hybridization (T. C. Currier and E. W. Nester (1976) J. Bacteriol. 126:157–165) or restriction enzyme analysis (D. Sciaky et al. (1978) Plasmid 1:238–253). Nopaline-type Ti plasmids have as little as 67% homology to each other (Currier and Nester, supra). A survey revealed that different Ri plasmids are very homologous to each other (P. Costantino et al. (1981) Plasmid 5:170–182). N. H. Drummond and M. D. Chilton (1978) J. Bacteriol. 136:1178–1183, showed that proportionally small sections of octopine and nopaline type Ti plasmids were homologous to each other. These homologies were mapped in detail by G. Engler et al. (1981) J. Mol. Biol. 152:183–208. They found that three of the four homologous regions were subdivided into three (overlapping the T-DNA), four (containing some onc genes), and nine (having onc genes) homologous sequences. The uninterrupted homology contains at least one tra gene (for conjugal transfer of the Ti plasmid to other bacterial cells), and genes involved in replication and incompatibility. This uninterrupted region has homology with a Sym plasmid (involved in symbiotic nitrogen fixation) from a species of Rhizobium, a different genus in the family Rhizobiaceae (R. K. Prakash et al. (1982) Plasmid 7:271–280). The order of the four regions is not conserved, though they are all oriented in the same direction. Part of the T-DNA sequence is very highly conserved between nopaline and octopine plasmids (M. D. Chilton et al. (1978) Nature 275:147–149, A. Depicker et al. (1978) Nature 275:150–153). Ri plasmids have been shown to have extensive homology among themselves, and to both octopine (F. F. White and E. W. Nester (1980) J. Bacteriol. 144:710–720) and nopaline (G. Risuleo et al. (1982) Plasmid 7:45–51) Ti plasmids, primarily in regions encoding onc genes. Ri T-DNA contains extensive though weak homologies to T-DNA from both types of Ti plasmid (L. Willmitzer et al. (1982) Mol. Gen. Genet. 186:3193–3197). Plant DNA from uninfected *Nicotiana glauca* contains sequences, referred to as cT-DNA (cellular T-DNA), that show homology to a portion of the Ri T-DNA (F. F. White et al. (1983) Nature 301:348–350).

It has been shown that a portion of the Ti (M. D. Chilton et al. (1977) Cell 11:263–271) or Ri (M. D. Chilton (1982) Nature 295:432–434, F. F. White et al. (1982) Proc. Natl. Acad. Sci. USA 79.:3193–3197, L. Willmitzer (1982) Mol. Gen. Genet. 186:16–22) plasmid is found in the DNA of tumorous plant cells. The transferred DNA is known as T-DNA. T-DNA is integrated into the host DNA (M. F. Thomashow et al. (1980) Proc. Natl. Acad. Sci. USA 77:6448–6452, N. S. Yadav et al. (1980) Nature 287:458–461) in the nucleus (M. P. Nuti et al. (1980) Plant Sci. Lett. 18:1–6, L. Willmitzer et al. (1980) Nature 287:359–361, M. D. Chilton et al. (1980) Proc. Natl. Acad. Sci. USA 77:4060–4064).

M. F. Thomashow et al. (1980) Proc. Natl. Acad. Sci. USA 77:6448–6452, and M. F. Thomashow et al. (1980) Cell 39:729–739, found the T-DNA from octopine-type Ti plasmids to have been integrated in two separate sections, TL-DNA and TR-DNA, left and right T-DNAs respectively. The copy numbers of TR and TL can vary (D. J. Merlo et al. (1980) Molec. Gen. Genet. 177:637–643). A core of T-DNA is highly homologous to nopaline T-DNA (Chilton et al. (1978) supra and Depicker et al. (1978) supra) is required for tumor maintenance, is found in TL, is generally present in one copy per cell, and codes for the genes tms, tmr, and tml. On the other hand TR can be totally dispensed with (M. De Beuckeleer et al. (1981) Molec. Gen. Genet. 183:283–288, G. Ooms et al. (1982) Cell 30:589–597), though found in a high copy number (D. J. Merlo et al. (1980) supra). G. Ooms et al. (1982) Plasmid 1:15–29, hypothesized that TR is involved in T-DNA integration, though they find that when TR is deleted from the Ti plasmid, *A. tumefaciens* does retain some virulence. G. Ooms et al. (1982) Cell 30:589–597, showed that though T-DNA is occasionally deleted after integration in the plant genome, it is generally stable and that tumors containing a mixture of cells that differ in T-DNA organization are the result of multiple transformation events. The ocs is found in TL but can be deleted from the plant genome without loss of phenotypes related to tumorous growth. The left border of integrated TL has been observed to be composed of repeats of T-DNA sequences which are in either direct or inverted orientations (R. B. Simpson et al. (1982) Cell 29:1005–1014).

In contrast to the situation in octopine-type tumors, nopaline T-DNA is integrated into the host genome in one continuous fragment (M. Lemmers et al. (1980) J. Mol. Biol. 144:353–376, P. Zambryski et al. (1980) Science 209:1385–1391). Direct tandem repeats were observed. T-DNA of plants regenerated from teratomas had minor modifications in the border fragments of the inserted DNA (Lemmers et al. supra). Sequence analysis of the junction between the right and left borders revealed a number of direct repeats and one inverted repeat. The latter spanned the junction (Zambryski et al. (1980) supra). The left junction has been shown to vary by at least 70 base pairs while the right junction varies no more than a single nucleotide (P. Zambryski et al. (1982) J. Molec. Appl. Genet. 1:361–370). Left and right borders in junctions of tandem arrays were separated by spacers which could be over 130 bp. The spacers were of unknown origin and contained some T-DNA sequences. T-DNA was found to be integrated into both repeated and low copy number host sequences.

N. S. Yadav et al. (1982) Proc. Natl. Acad. Sci. USA 79:6322–6326, have found a chi site, which in the bacteriophage lambda augments general recombination in the surrounding DNA as far as 10 kilobases away, in a nopaline Ti plasmid just outside the left end of the T-DNA. R. B. Simpson et al. (1982) Cell 29:1005–1014, have not observed a chi sequence in an octopine Ti plasmid, though the possible range of action does not eliminate the possibility of one being necessary and present but outside of the region sequenced. The significance of the chi in the Ti plasmid is not known. If the chi has a function, it is probably used in Agrobacterium cells and not in the plants, as chi is not found within the T-DNA.

Agrobacterium—Manipulations of the TIP Plasmids

As detailed in the section on Shuttle Vectors, technology has been developed for the introduction of altered DNA sequences into desired locations on a TIP plasmid. Transposons can be easily inserted using this technology (D. J. Garfinkel et al. (1981) Cell 27:143–153). J. P. Hernalsteen et al. (1980) Nature 287:654–656, have shown that a DNA sequence (here a bacterial transposon) inserted into T-DNA in the Ti plasmid is transferred and integrated into the recipient plant's genome. Though insertion of foreign DNA has been done with a number of genes from different sources, to date the genes have not been expressed under control of their own promoters. Sources of these genes include alcohol dehydrogenase (Adh) from yeast (K. A. Barton et al. (1983)), AdhI (J. Bennetzen, unpublished) and zein from corn, interferon and globin from mammals, and the mammalian virus SV40 (J. Schell, unpublished). M. Holsters et al. (1982) Mol. Gen. Genet. 185:283–289, have shown that a bacterial transposon (Tn7) inserted into T-DNA could be recovered in a fully functional and seemingly unchanged form after integration into a plant genome.

Deletions can be generated in a TIP plasmid by several methods. Shuttle vectors can be used to introduce deletions constructed by standard recombinant DNA techniques (Cohen and Boyer U.S. Pat. No. 4,237,224). Deletions with one predetermined end can be created by the improper excision of transposons (B. P. Koekman et al. (1979) Plasmid 2:347–357, G. Ooms et al. (1982) Plasmid 7:15–29). J. Hille and R. Schilperoot (1981) Plasmid 7:151–154, have demonstrated that deletions having both ends at predetermined positions can be generated by use of two transposons. The technique can also be used to construct "recombinant DNA" molecules in vivo.

The nopaline synthase gene has been used for insertion of DNA segments coding for drug resistance that can be used to select for transformed plant cells. M. Bevan (reported by M. D. Chilton et al. (18 Jan. 1983) 15th Miami Winter Symp., see also J. L. Marx (1983) Science 219:830) and R. Horsch et al. (18 Jan. 1983) 15th Miami Winter Symp., see Marx, supra, have inserted the kanamycin resistance gene (neomycin phosphotransferase) from Tn5 behind (under control of) the nopaline promoter. The construction was used to transform plant cells which in culture displayed resistance to kanamycin and its analogs such as G418. J. Schell et al. (18 Jan. 1983) 15th Miami Winter Symp. (see also Marx, supra), reported a similar construction, in which the methotrexate resistance gene (dihydrofolate reductase) from Tn7 was placed behind the nopaline synthase promoter. Transformed cells were resistant to methotrexate. As plant cells containing octopine synthase are resistant to the toxic chemical homo-arginine, G. M. S. Van Slogteren et al. (1982) Plant Mol. Biol. 1:133–142, have proposed using that enzyme as a selectable marker.

M. D. Chilton et al. (1983) supra, reported that A. de Framond has constructed a "mini-Ti plasmid". In the nopaline T-DNA there is normally only one site cut by the restriction enzyme KpnI. A mutant lacking the site was constructed and a KpnI fragment, containing the entire nopaline T-DNA, was isolated. This fragment together with a kanamycin resistance gene was inserted into pRK290, thereby resulting in a plasmid which could be maintained in *A. tumefaciens* and lacked almost all non-T-DNA Ti sequences. By itself, this plasmid was not able to transform plant cells. However, when placed in an *A. tumefaciens* strain containing an octopine Ti plasmid, tumors were induced which synthesized both octopine and nopaline. This indicated that the missing nopaline Ti plasmid functions were complemented by the octopine Ti plasmid, and that the nopaline "mini-Ti" was functional in the transformation of plant cells. Chilton et al. (1983) supra also reported on the construction of a "micro-Ti" plasmid made by resectioning the mini-Ti with SmaI to delete essentially all of T-DNA but the nopaline synthase gene and the left and right borders. The micro-Ti was inserted into a modified pRK290 plasmid that was missing its SmaI site, and employed in a manner similar to mini-Ti, with comparable results.

H. Lorz et al. (1982) in *Plant Tissue Culture* 1982, ed: A. Fujwara, pp. 511–512, reported the construction of a plasmid vector, apparently independent of the TIP system for DNA uptake and maintenance, that used the nopaline synthase gene as a marker.

Phaseolin and Gene Regulation

In general the genes of higher eukaryotes are highly regulated. A multicellular organism, such as a plant, has a number of differentiated tissues, each with its own specialized functions, each of which requires specialized gene products. One such tissue is the cotyledon. In legumes, the cotyledons usually serve as the storage tissue for the seed, holding reserves of lipid, carbohydrate, minerals, and protein until the seed needs them during germination. In *Phaseolus vulgaris* L. (also known as the French bean, kidney bean, navy bean, green bean and other names), the major storage protein is known as phaseolin. This protein comprises a small number of molecular species that are extremely homologous and equivalent to one another. Phaseolin contributes most of the nutrition value of dried beans, often comprising more than 10% of the weight of a dried bean.

Phaseolin is highly regulated during the life cycle of *P. vulgaris*. The protein is made essentially only while seed is developing within the pod. Levels rise from the limit of detection to as much as half the seed's protein content, following genetically determined schedules for synthesis. At its peak, phaseolin synthesis can account for over 80% of a cotyledon cell's protein synthesis. At other times and in other tissues, phaseolin synthesis is undetectable. The extreme nature of phaseolin's regulation, coupled with its worldwide nutritional importance, has lead to much interest in the study of phaseolin, its properties, and its regulation.

SUMMARY OF THE INVENTION

The invention disclosed herein provides a plant comprising a genetically modified plant cell having a plant structural gene introduced and expressed therein under control of a T-DNA promoter. Further, the invention provides plant tissue comprising a plant cell whose genome includes T-DNA comprising a plant structural gene inserted in such orientation and spacing with respect to a T-DNA promoter as to be expressible in the plant cell under control of the T-DNA promoter. Also provided are novel strains of bacteria containing and replicating T-DNA, as defined herein, the T-DNA being modified to contain an inserted plant structural gene in such orientation and spacing with respect to a T-DNA promoter as to be expressible in a plant cell under control of said T-DNA promoter. Further, the invention provides novel plasmids having the ability to replicate in *E. coli* and comprising T-DNA, and further comprising a plant structural gene inserted within T-DNA contained within the plasmid, in such manner as to be expressible in a plant cell under control of a T-DNA promoter.

The experimental work disclosed herein is believed to be the first demonstration that plant structural genes are expressible in plant cells under control of a T-DNA promoter, after introduction via T-DNA, that is to say, by inserting the plant structural genes into T-DNA under control of a T-DNA promoter and introducing the T-DNA containing the insert into a plant cell using known means. The disclosed experiments are also believed to provide the first demonstration that plant structural genes containing introns are expressed in plant cells under control of a T-DNA promoter after introduction via T-DNA. These results are surprising in view of the fact that the genes previously reported to be expressible in T-DNA under control of a T-DNA promoter, either endogenous T-DNA genes or inserted foreign genes, lacked introns. The results are unexpected also in view of the prior art failure to demonstrate that a T-DNA promoter could function to control expression of a plant structural gene when the latter is introduced into T-DNA under the proper conditions. The invention is useful for genetically modifying plant tissues and whole plants by inserting useful plant structural genes from other plant species or strains. Such useful plant structural genes include, but are not limited to, genes coding for storage proteins, lectins, disease resistance factors, herbicide resistance factors, insect resistance factors, environmental stress tolerance factors, specific flavor elements, and the like. The invention is exemplified by introduction and expression of a structural gene for phaseolin, the major seed storage protein of the bean *Phaseolus vulgaris* L., into sunflower and tobacco plant cells. Once plant cells expressing a plant structural gene under control of a T-DNA promoter are obtained, plant tissues and whole plants can be regenerated therefrom using methods and techniques well known in the art. The regenerated plants are then reproduced by conventional means and the introduced genes can be transferred to other strains and cultivars by conventional plant breeding techniques. The introduction and expression of the structural gene for phaseolin, for example, can be used to enhance the protein content and nutritional value of forage crops such as alfalfa. Other uses of the invention, exploiting the properties of other structural genes introduced into other plant species will be readily apparent to those skilled in the art. The invention in principle applies to any introduction of a plant structural gene into any plant species into which T-DNA can be introduced and in which T-DNA can remain stably replicated. In general these species include, but are not limited to, dicotyledenous plants, such as sunflower (family Compositeae), tobacco (family Solanaceae), alfalfa, soybeans and other legumes (family Leguminoseae) and most vegetables.

BRIEF DESCRIPTION OF THE DRAWINGS

FIG. 2A and 2B present the nucleotide sequence of the octopine synthase gene (ocs) of the T-DNA of pTi15955 of *Agrobacterium tumefaciens* strain 15955. The deduced amino acid sequence is written below the coding sequence; the stop codon is indicated by "END" written below.

FIG. 3A–3C present the nucleotide sequences of a *Phaseolus vulgaris* (bean) phaseolin gene and of the corresponding cDNA clone. Intervening sequences (introns) are indicated by IVS 1 through IVS 5, with the intron lengths given in bases. The start of transcription is indicated by "CAP", the translation start site for the phaseolin protein is indicated by "FMet", and the stop codon is indicated by "TER" for termination of translation. The signal for polyadenylation is underlined.

FIG. 4A and 4B present the nucleotide sequence of the nopaline synthase gene (nos) of pTiC58 of *Agrobacterium tumefaciens*. The deduced amino acid sequence is written below the coding sequence, and the stop codon is indicated by "END" written below.

FIG. 6(a) shows SmaI restriction sites in the vicinity of the nos gene of nopaline T-DNA. FIG. 6(b) shows a restriction map of the SmaI fragment comprising the nos gene. That SmaI fragment was modified by the addition of BglII linkers, the XhoI fragment upstream of the nopaline synthase gene was removed, and a deletion was made extending from the ClaI site within the nos gene to a ClaI site just downstream from nos. FIG. 6(c) shows the modified 3.6 kbp T-DNA insert of pKS-nopIV. FIG. 6(d) shows the relevant portion of the inserted DNA of pKS-nopIVKB3.8, in which the vector sequences are pRK290. The kanamycin resistance and the phaseolin genes were excised from pKS4-KB on a 4.8 kb EcoRI fragment.

FIG. 13 illustrates a circular restriction map of p7.2. The cross-hatched portion represents the EcoRI *Phaseolus vulgaris* L. genomic DNA fragment comprising the phaseolin gene. The arrow indicates the position and direction of transcription of the phaseolin gene.

FIG. 14 illustrates a circular restriction map of pKS-proI-KB. To construct pKS-proI-KB, pKS4-KB was digested with ClaI and the 4.9 kbp fragment comprising the nptII and phaseolin genes was purified and ligated with pKS-proI linearized with ClaI. The continuous thin line between the EcoRI sites represents 20 kb of pRK290 vector sequences.

FIG. 35 illustrates the modification of p203 by the conversion of a HpaI site to a BglII site. T-DNA sequences are indicated by cross-hatching.

FIG. 36 illustrates a circular restriction map of pKS-oct.tmr. This plasmid was constructed by ligating BglII-cut, modified p203 (FIG. 37) with the small BclI/BglII fragment of pKS-6, which fragment contains the cam gene. T-DNA is indicated by cross-hatching and the position and orientation of the cam gene is indicated by an open box and an arrow, respectively.

FIG. 38 gives the coding sequence of the Agrobacterium T-DNA gene tml and the deduced amino acid sequence written below. The stop codon is indicated by "END" written below.

DETAILED DESCRIPTION OF THE INVENTION

Figure 1:
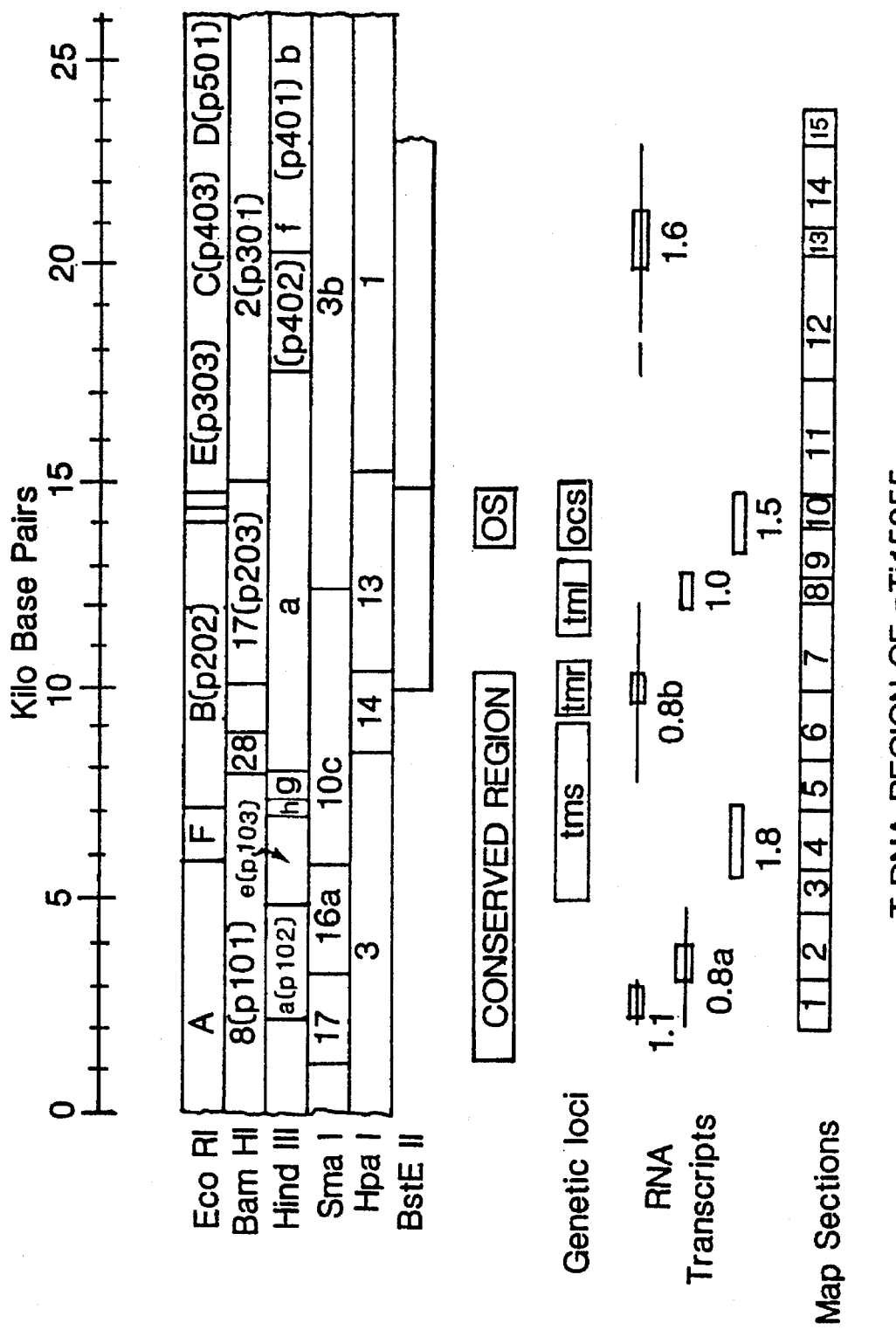
FIG. 1 illustrates various pTi15955 T-DNA sequences cloned into the pBR322, e.g., plasmids p202 and p303 and maps for a number of restriction endonucleases. The conserved T-DNA region, various genetic loci, including the ocs gene (octopine synthase, OS), the positions and relative sizes of several RNA transcripts which have been mapped are indicated.

The following definitions are provided, in order to remove ambiguities to the intent or scope of their usage in the specification and claims.

T-DNA: A segment of DNA derived from the tumor-inducing principle (TIP) which becomes integrated in the plant genome. As used herein, the term includes DNA originally derived from any tumor-inducing strain of Agrobacterium including *A. tumefaciens* and *A. rhizogenes*, the inserted segment of the latter sometimes referred to in the prior art as R-DNA. In addition, as used herein the term T-DNA includes any alterations, modifications, mutation, insertions and deletions either naturally occurring or introduced by laboratory procedures, a principle structural requirement and limitation to such modifications being that sufficient right and left ends of naturally-occurring T-DNAs be present to insure the expected function of stable integration in the transformed plant cell genome which is characteristic of T-DNA. In addition, the T-DNA must contain at least one T-DNA promoter in sufficiently complete form to control initiation of transcription and initiation of translation of an inserted plant structural gene. Preferably, an insertion site will be provided "downstream" in the direction of transcription and translation initiated by the promoter, so located with respect to the promoter to enable a plant structural gene inserted therein to be expressed under control of the promoter, either directly or as a fusion protein.

Plant structural gene: As used herein includes that portion of a plant gene comprising a DNA segment coding for a plant protein, polypeptide or portion thereof but lacking those functional elements of a plant gene that regulate initiation of transcription and initiation of translation, commonly referred to as the promoter region. A plant structural gene may contain one or more introns or it may constitute an uninterrupted coding sequence. A plant structural gene may be derived in whole or in part from plant genomic DNA, cDNA and chemically synthesized DNA. It is further contemplated that a plant structural gene could include modifications in either the coding segments or the introns which could affect the chemical structure of the expression product, the rate of expression or the manner of expression control. Such modifications could include, but are not limited to, mutations, insertions, deletions, and "silent" modifications that do not alter the chemical structure of the expression product but which affect intercellular localization, transport, excretion or stability of the expression product. The structural gene may be a composite of segments derived from a plurality of sources, naturally occurring or synthetic, coding for a composite protein, the composite protein being in part a plant protein.

T-DNA promoter: Refers to any of the naturally occurring promoters commonly associated with integrated T-DNA. These include, but are not limited to, promoters of the octopine synthase gene, nopaline synthase gene, Tms, Tml and Tmr genes, depending in part on the TIP source of the T-DNA. Expression under control of a T-DNA promoter may take the form of direct expression in which the structural gene normally controlled by the promoter is removed and replaced by the inserted plant structural gene, a start codon being provided either as a remnant of the T-DNA structural gene or as part of the inserted plant structural gene, or by fusion protein expression in which part or all of the plant structural gene is inserted in correct reading frame phase within the existing T-DNA structural gene. In the latter case, the expression product is referred to as a fusion protein.

Plant tissue: Includes differentiated and undifferentiated tissues of plants including roots, shoots, pollen, seeds, tumor tissue, such as crown galls, and various forms of aggregations of plant cells in culture, such as embryos and calli.

Plant cell: As used herein includes plant cells in planta and plant cells and protoplasts in culture.

Production of a genetically modified plant expressing a plant structural gene introduced via T-DNA combines the specific teachings of the present disclosure with a variety of techniques and expedients known in the art. In most instances, alternative expedients exist for each stage of the overall process. The choice of expedients depends on variables such as the choice of the basic TIP, the plant species to be modified and the desired regeneration strategy, all of which present alternative process steps which those of ordinary skill are able to select and use to achieve a desired result. The fundamental aspects of the invention are the nature and structure of the plant structural gene and its means of insertion into T-DNA. The remaining steps in obtaining a genetically modified plant include transferring the modified T-DNA to a plant cell wherein the modified T-DNA becomes stably integrated as part of the plant cell genome, techniques for in vitro culture and eventual regeneration into whole plants, which may include steps for selecting and detecting transformed plant cells and steps of transferring the introduced gene from the originally transformed strain into commercially acceptable cultivars.

A principle feature of the present invention is the construction of T-DNA having an inserted plant structural gene under control of a T-DNA promoter, as these terms have been defined, supra. The plant structural gene must be inserted in correct position and orientation with respect to the T-DNA promoter. Position has two aspects. The first relates to which side of the promoter the structural gene is inserted. It is known that the majority of promoters control initiation of transcription and translation in one direction only along the DNA. The region of DNA lying under promoter control is said to lie "downstream" or alternatively "behind" the promoter. Therefore, to be controlled by the promoter, the correct position of plant structural gene insertion must by "downstream" from the promoter. (It is recognized that a few known promoters exert bi-directional control, in which case either side of the promoter could be considered to be "downstream" therefrom.) The second aspect of position refers to the distance, in base pairs, between known functional elements of the promoter, for example the transcription initiation site, and the translational start site of the structural gene. Substantial variation appears to exist with regard to this distance, from promoter to promoter. Therefore, the structural requirements in this regard are best described in functional terms. As a first approximation, reasonable operability can be obtained when the distance between the promoter and the inserted structural gene is similar to the distance between the promoter and the T-DNA gene it normally controls. Orientation refers to the directionality of the structural gene. By convention, that portion of a structural gene which ultimately codes for the amino terminus of the plant protein is termed the 5' end of the structural gene, while that end which codes for amino acids near the carboxyl end of the protein is termed the 3' end of the structural gene. Correct orientation of the plant structural gene is with the 5' end thereof proximal to the T-DNA promoter. An additional requirement in the case of constructions leading to fusion protein expression is that the insertion of the plant structural gene into the T-DNA structural gene sequence must be such that the coding sequences of the two genes are in the same reading frame phase, a structural requirement which is well understood in the art. An exception to this requirement, of relevance to the present invention, exists in the case where an intron separates the T-DNA gene from the first coding segment of the plant structural gene. In that case, the intron splice sites must be so positioned that the correct reading frame for the T-DNA gene and the plant structural gene are restored in phase after the intron is removed by post-transcriptional processing. The source of T-DNA may be any of the TIP plasmids. The plant structural gene is inserted by standard techniques well known to those skilled in the art. Differences in rates of expression may be observed when a given plant structural gene is inserted under control of different T-DNA promoters. Different properties, including such properties as stability, intracellular localization, excretion, antigenicity and other functional properties of the expressed protein itself may be observed in the case of fusion proteins depending upon the insertion site, the length and properties of the segment of T-DNA protein included within the fusion protein and mutual interactions between the components of the fusion protein that effect folded configuration thereof, all of which present numerous opportunities to manipulate and control the functional properties of the expression product, depending upon the desired end use. Expression of the phaseolin structural gene has been observed when that gene was inserted under control of the octopine synthase promoter from an octopine plasmid of *A. tumefaciens*.

A convenient means for inserting a plant structural gene into T-DNA involves the use of a shuttle vector, as described supra, having a segment of T-DNA (that segment into which insertion is desired) incorporated into a plasmid capable of replicating in *E. coli*. The T-DNA segment contains a restriction site, preferably one which is unique to the shuttle vector. The plant structural gene can be inserted at the unique site in the T-DNA segment and the shuttle vector is transferred into cells of the appropriate Agrobacterium strain, preferably one whose T-DNA is homologous with the T-DNA segment of the shuttle vector. The transformed Agrobacterium strain is grown under conditions which permit selection of a double-homologous recombination event which results in replacement of a pre-existing segment of the Ti plasmid with a segment of T-DNA of the shuttle vector.

Following the strategy just described, the modified T-DNA can be transferred to plant cells by any technique known in the art. For example, this transfer is most conveniently accomplished either by direct infection of plants with the novel Agrobacterium strain containing a plant structural gene incorporated within its T-DNA, or by co-cultivation of the Agrobacterium strain with plant cells. The former technique, direct infection, results in due course in the appearance of a tumor mass or crown gall at the site of infection. Crown gall cells can be subsequently grown in culture and, under appropriate circumstances known to those of ordinary skill in the art, regenerated into whole plants that contain the inserted T-DNA segment. Using the method of co-cultivation, a certain proportion of the plant cells are transformed, that is to say have T-DNA transferred therein and inserted in the plant cell genome. In either case, the transformed cells must be selected or screened to distinguish them from untransformed cells. Selection is most readily accomplished by providing a selectable marker incorporated into the T-DNA in addition to the plant structural gene. Examples include either dihydrofolate reductase or neomycin phosphotransferase expressed under control of a nopaline synthase promoter. These markers are selected by growth in medium containing methotrexate or kanamycin, respectively, or their analogs. In addition, the T-DNA provides endogenous markers such as the gene or genes controlling hormone-independent growth of Ti-induced tumors in culture, the gene or genes controlling abnormal morphology of Ri-induced tumor roots, and genes that control resistance to toxic compounds such as amino acid analogs, such resistance being provided by an opine synthase. Screening methods well known to those skilled in the art include assays for opine production, specific hybridization to characteristic RNA or T-DNA sequences, or immunological assays for specific proteins, including ELISA (acronym for "enzyme linked immunosorbant assay"), radioimmune assays and "western" blots.

An alternative to the shuttle vector strategy involves the use of plasmids comprising T-DNA or modified T-DNA, into which a plant structural gene is inserted, said plasmids being capable of independent replication in an Agrobacterium strain. Recent evidence indicates that the T-DNA of such plasmids can be transferred from an Agrobacterium strain to a plant cell provided the Agrobacterium strain contains certain trans-acting genes whose function is to promote the transfer of T-DNA to a plant cell. Plasmids that contain T-DNA and are able to replicate independently in an Agrobacterium strain are herein termed "sub-TIP" plasmids. A spectrum of variations is possible in which the sub-TIP plasmids differ in the amount of T-DNA they contain. One end of the spectrum retains all of the T-DNA from the TIP plasmid, and is sometimes termed a "mini-TIP" plasmid. At the other end of the spectrum, all but the minimum amount of DNA surrounding the T-DNA border is deleted, the remaining portions being the minimum necessary to be transferrable and integratable in the host cell. Such plasmids are termed "micro-TIP". Sub-TIP plasmids are advantageous in that they are small and relatively easy to manipulate directly. After the desired structural gene has been inserted, they can easily be introduced directly into an Agrobacterium cell containing the trans-acting genes that promote T-DNA transfer. Introduction into an Agrobacterium strain is conveniently accomplished either by transformation of the Agrobacterium strain or by conjugal transfer from a donor bacterial cell, the techniques for which are well known to those of ordinary skill.

Regeneration is accomplished by resort to known techniques. An object of the regeneration step is to obtain a whole plant that grows and reproduces normally but which retains integrated T-DNA. The techniques of regeneration vary somewhat according to principles known in the art, depending upon the origin of the T-DNA, the nature of any modifications thereto and the species of the transformed plant. Plant cells transformed by an Ri-type T-DNA are readily regenerated, using techniques well known to those of ordinary skill, without undue experimentation. Plant cells transformed by Ti-type T-DNA can be regenerated, in some instances, by the proper manipulation of hormone levels in culture. Preferably, however, the Ti-transformed tissue is most easily regenerated if the T-DNA has been mutated in one or both of the Tmr and Tms genes. Inactivation of these genes returns the hormone balance in the transformed tissue towards normal and greatly expands the ease and manipulation of the tissue's hormone levels in culture, leading to a plant with a more normal hormone physiology that is readily regenerated. In some instances, tumor cells are able to regenerate shoots which carry integrated T- DNA and express T-DNA genes, such as nopaline synthase, and which also express an inserted plant structural gene. The shoots can be maintained vegetatively by grafting to rooted plants and can develop fertile flowers. The shoots thus serve as parental plant material for normal progeny plants carrying T-DNA and expressing the plant structural gene inserted therein.

EXAMPLES

The following Examples utilize many techniques well known and accessible to those skilled in the arts of molecular biology and manipulation of TIPs and Agrobacterium; such methods are not always described in detail. Enzymes are obtained from commercial sources and are used according to the vendor's recommendations or other variations known to the art. Reagents, buffers and culture conditions are also known to those in the art. Reference works containing such standard techniques include the following: R. Wu, ed. (1979) Meth. Enzymol. 68; J. H. Miller (1972) *Experiments in Molecular Genetics;* R. Davis et al. (1980) *Advanced Bacterial Genetics;* and R. F. Schleif and P. C Wensink (1982) *Practical Methods in Molecular Biology.*

In the Examples, special symbols are used to clarify sequences. Sequences that do or could code for proteins are underlined, and codons are separated with slashes (/). The positions of cuts or gaps in each strand caused by restriction endonucleases or otherwise are indicated by the placement of asterisks (*). (In Example 4, a double-stranded DNA molecule is represented by a single line flanked by asterisks at the sites of restriction enzyme cuts; the approximate position of a gene is there indicated by underlined "X"'s under the single line.) With the exception of the plasmid IIc, plasmids, and only plasmids, are prefaced with a "p", e.g., p3.8 or pKS4. Cells containing plasmids are indicated by identifying the cell and parenthetically indicating the plasmid, e.g., *A. tumefaciens* or K802(pKS4-KB). Table 1 provides an index useful for identifying plasmids and their interrelationships. Table 2 provides an index of deposited strains.

Figure 37:
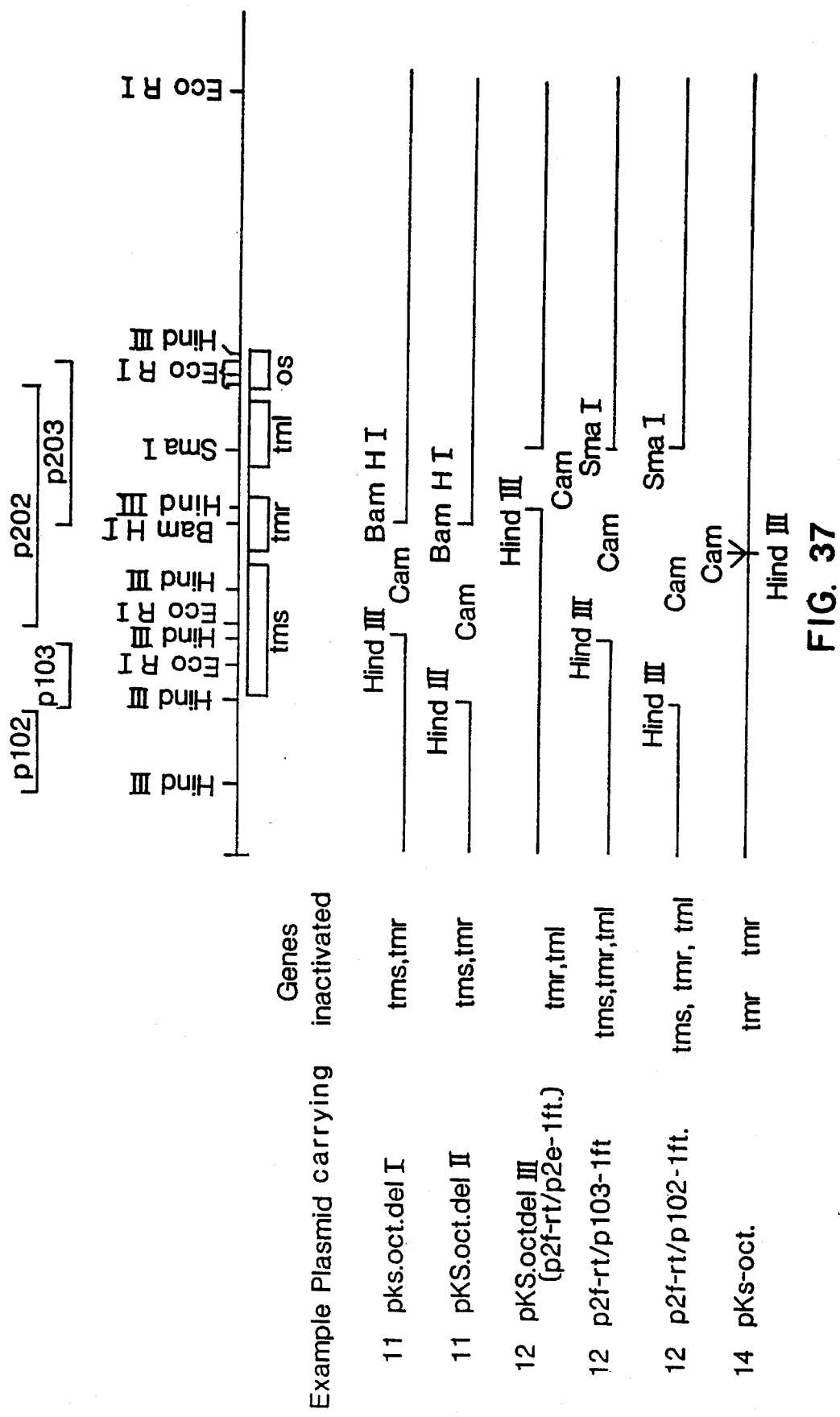
FIG. 37 summarizes relevant features of plasmids whose constructions are described in Examples 11, 12 and 14. The T-DNA restriction fragments and the activities of the tms, tmr and tml genes in the noted plasmids are given.
Figure 38:
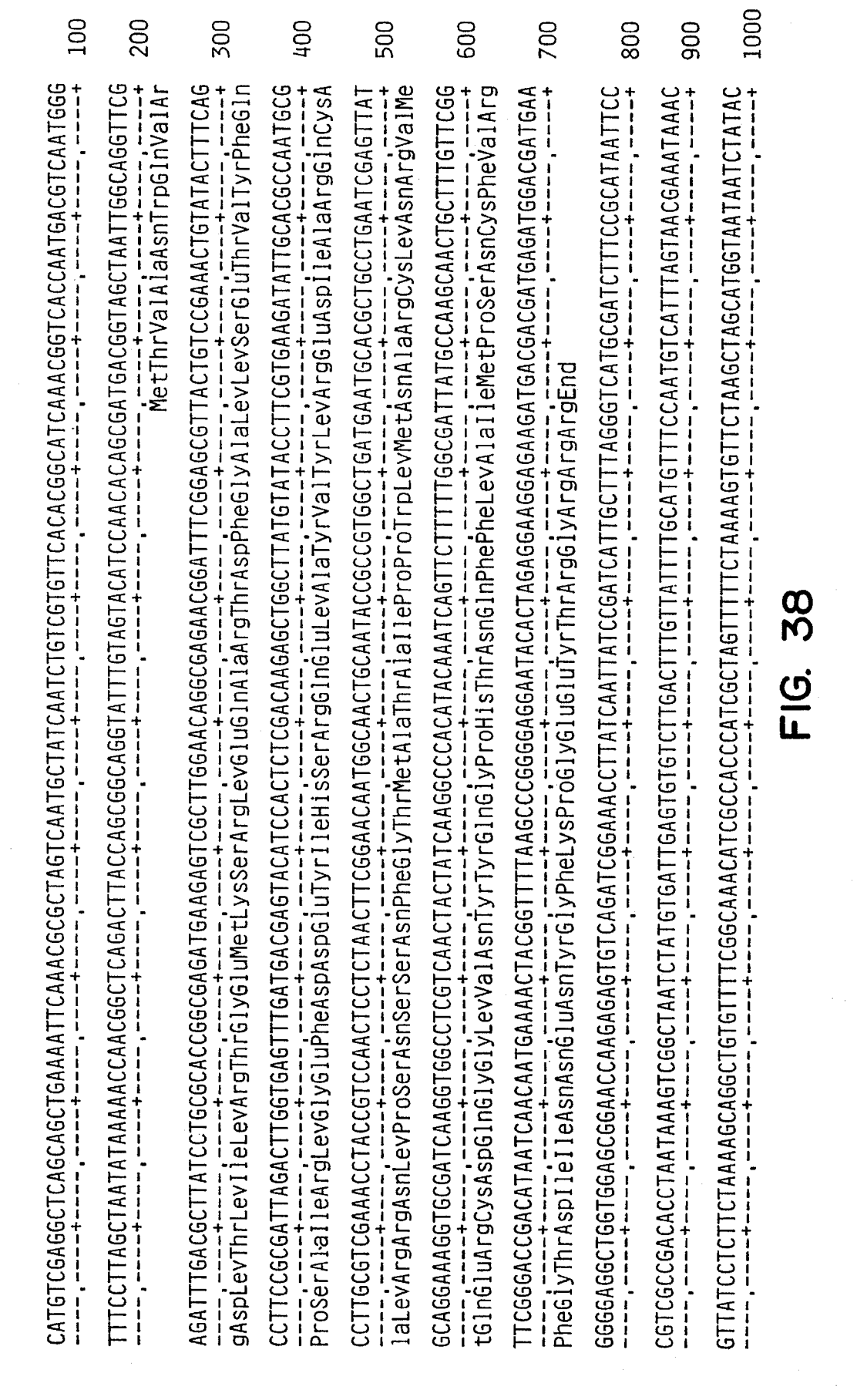

FIG. 37 provides a useful comparison of the constructions described in Examples, 11, 12, and 14. The nucleotide sequence of an important T-DNA gene, tml, though not used in these Examples, is set forth in FIG. 38; it is useful in designing constructions not described herein.

octopine synthase sequence and reading frame were found to be as follows near a site cut by the restriction enzyme EcoRI:

```
              EcoRI
5'... ATG/GGC/CAG/CAA/GG*A/ATT/CTT           ...3'

3'... TAC CCG GTC GTT CC T TAA*GAA           ...5'
  ... Met  Gly  Gln  Gln  Gly  Ile  Leu      ...
      84   85   86   87   88   89   90
```

Cleavage with EcoRI yields a fragment with the following end:

```
      ... ATG/GGC/CAG/CAA/GG              3'
      ... TAC CCG GTC GTT CCTT            5'
```

Figure 3C:
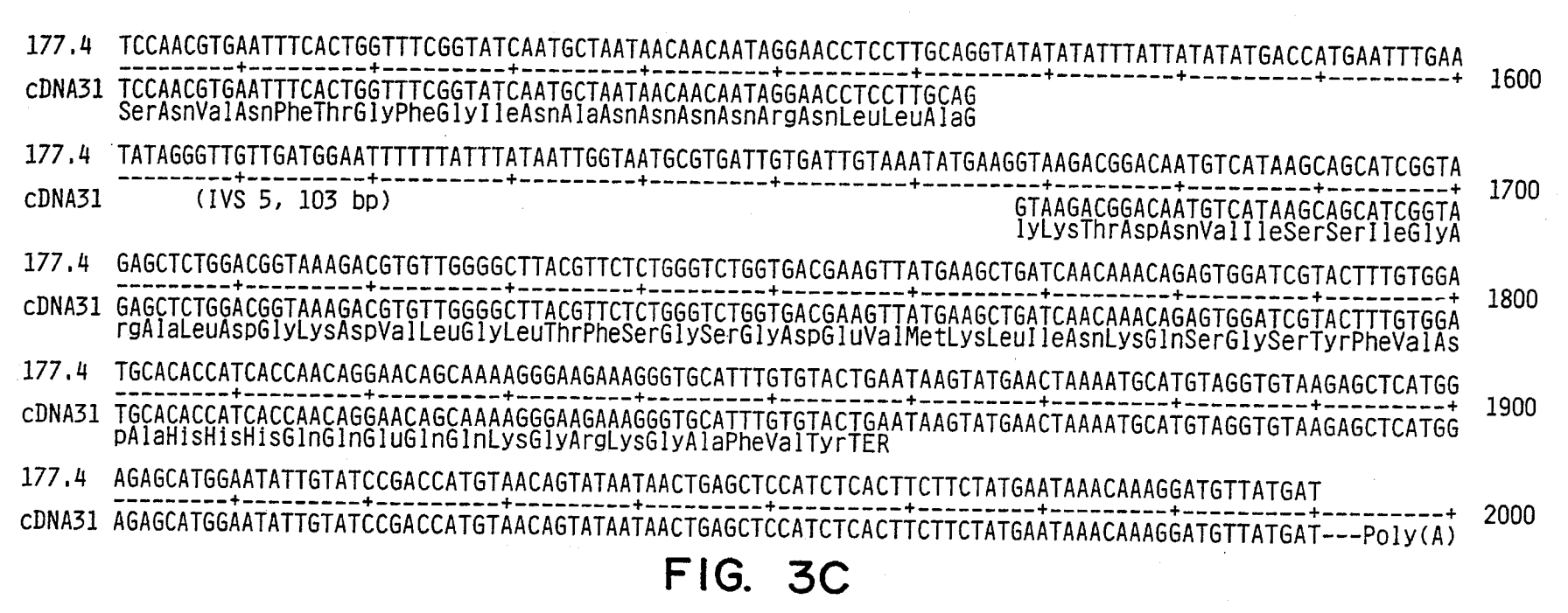

The structural gene for the bean seed storage protein phaseolin (previously sequenced, FIG. 3) contains an EcoRI site near its 5' (amino terminal) end as follows:

```
              EcoRI
... CTG/TTG/CTG/GG*A/ATT/CTT/TTC             ...

... GAC AAC GAC CC T TAA*GAA AAG             ...
... Leu Leu Leu Gly  Ile Leu Phe             ...
    9   10  11  12   13  14  15
```

Cleavage with EcoRI yields a fragment with an end as follows:

```
      5'     A/ATT/CTT/TTC ...
      3'         GAA AAG ...
```

These two fragments, after ligation, form the following structure:

```
                        EcoRI
... ATG/GGC/CAG/CAA/GG*A/AT T/CTT/TTC         ...
... TAC CCG GTC GTT CC T TA*A GAA AAG         ...
... Met Gly Gln Gln Gly Ile  Leu Phe          ...
    84  85  86  87  88  89   90                    octopine synthase
                             12   13  14  15       phaseolin
```

Not only are the same reading frames preserved, but there are no intervening stop signals generated.

So in short, the EcoRI/BamHI restriction endonuclease fragment of the phaseolin gene was ligated at the EcoRI site to the octopine synthase gene of the T-DNA of pTi15955. This fusion gene contains the ocs promoter, the first 90 amino acids of octopine synthase, the phaseolin gene minus its promoter and its first 11 amino acids, and a three amino acid junction identical to sequences present in both parent proteins.

1.1 Removal of the EcoRI Site from pBR322

The EcoRI site in pBR322 was removed by digesting with EcoRI, filling in with T-4 DNA polymerase, blunt end

EXAMPLE 1

Figure 2A:
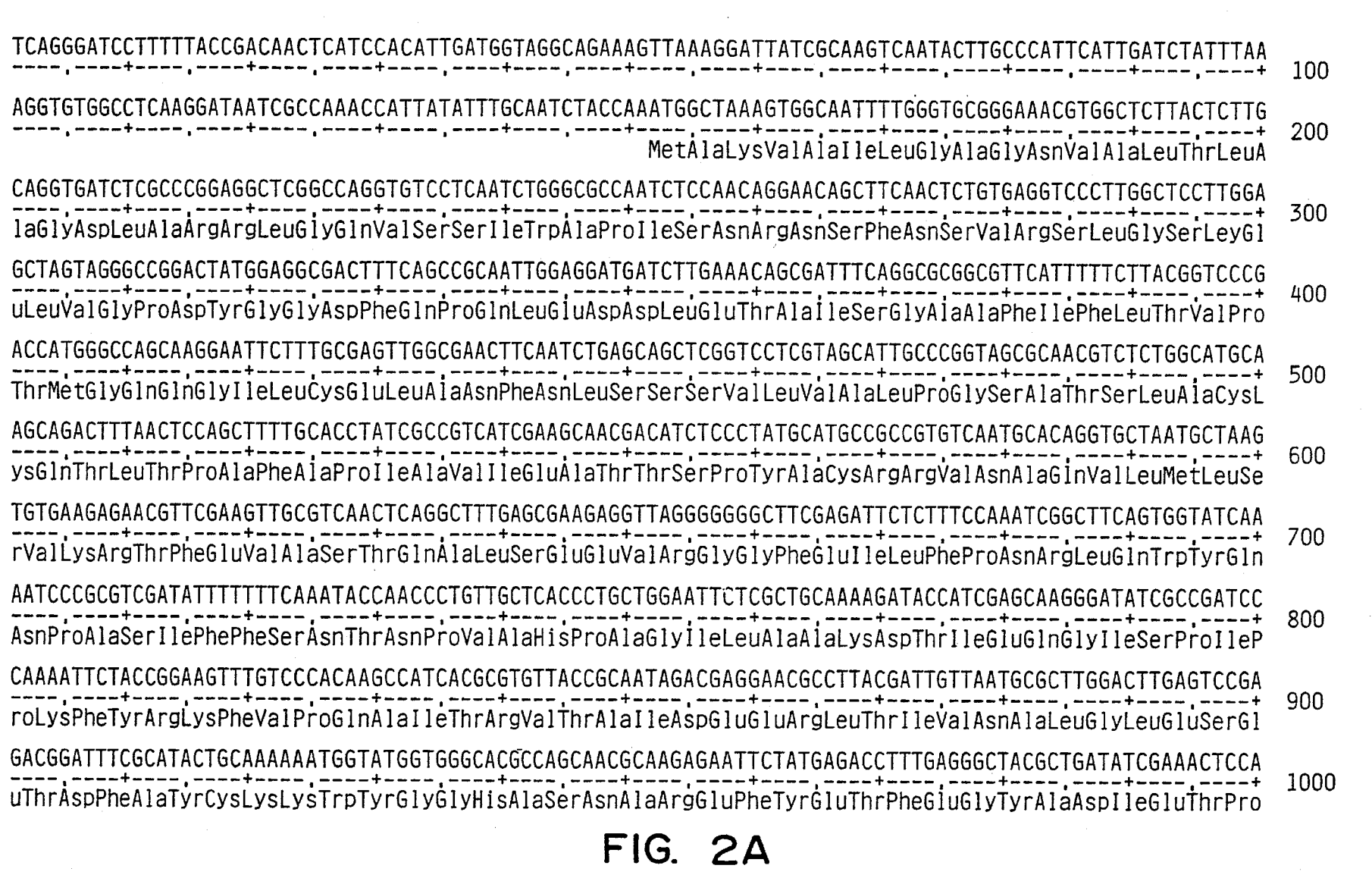

A fusion protein gene was constructed consisting of the octopine synthase promoter, the amino terminal 90 amino acids of the structural gene for octopine synthase, a 3 amino acid overlap between the two genes, and all of phaseolin except for codons encoding its first 11 amino acids. Prior to the start of construction, a clone of pTi15955 T-DNA, p233, (the sequences defined by p203 and p303, in pBR322, see FIG. 1) was sequenced from the BamHI site to the PvuII site. This includes all of the octopine synthase gene (FIG. 2). The ligation and transformation into *E. coli* strain HB101. Selection of transformants was made with ampicillin and colonies were screened by isolating small amounts of plasmid DNA (T. Maniatis et al. (1982) in *Molecular Cloning*, Cold Spring Harbor Laboratory, Cold Spring Harbor, N.Y.) and selecting a clone without an EcoRI site called pBR322-R.

Figure 39:
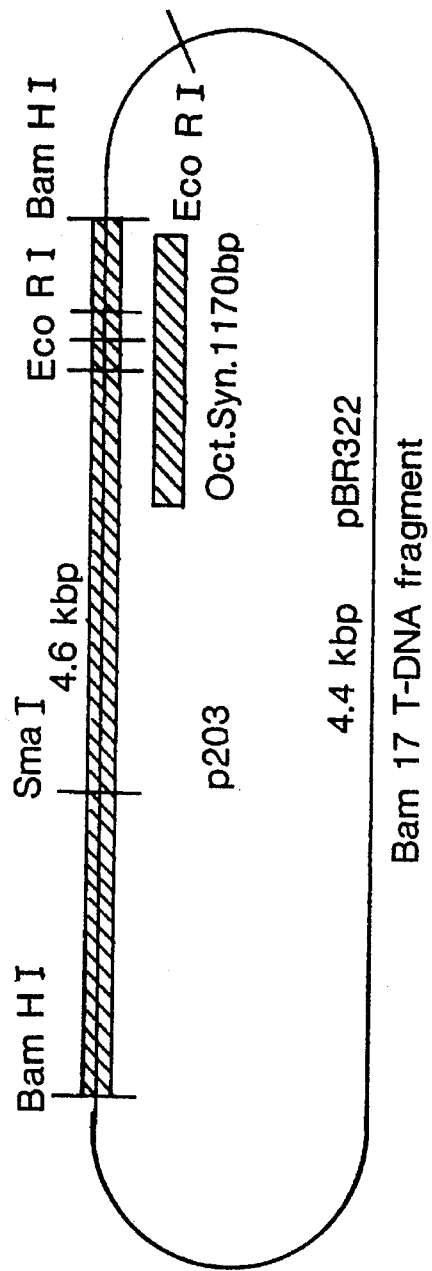
FIG. 39 illustrates the circular restriction map of p203, in which the T-DNA BamHI fragment 17, shaded is cloned into the BamHI site of pBR322. The 1170 bp octopine synthase gene is indicated by a cross-hatched box.

1.2 Cloning of the BamHI T-DNA Fragment into pBR322-R p203 (FIG. 39) was isolated and digested with BamHI. The 4.7 kbp fragment of T-DNA was isolated by agarose gel electrophoresis and ligated into the BamHI site of pBR322-R. This plasmid was transformed into *E. coli* strain HB101 and selected for using ampicillin resistance and tetracycline sensitivity. A positive clone was selected and called pKS169.

1.3 Removal of the EcoRI Sites and Fragments from the Octopine Synthase Gene pKS169 was isolated and digested with EcoRI. An 8.6 kbp fragment was isolated by agarose gel electrophoresis and purified. This fragment had the 2 small (0.36 kbp and 0.2 kbp) fragments in the ocs gene removed.

Figure 7:
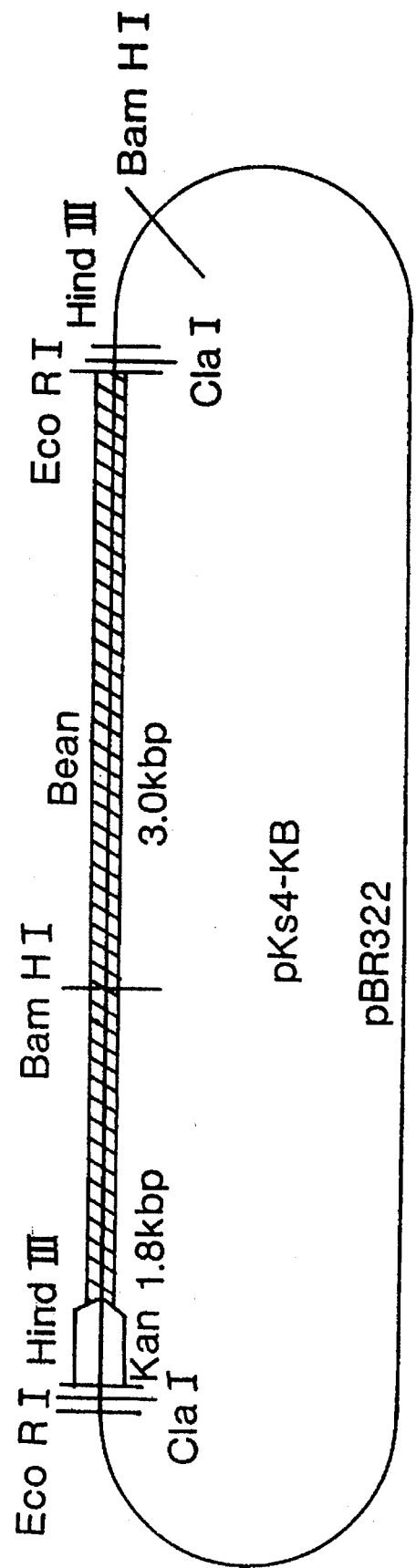
FIG. 7 illustrates the restriction map of pKS4-KB. This plasmid was constructed by ligating HindIII-cut pBR322, the 3.0 kbp HindIII/BamHI fragment of pKS-4 comprising the nptII gene of Tn5 and the 3.0 kbp HindIII/BamHI fragment of p7.2 comprising the bean phaseolin gene.

1.4 Isolation of the EcoRI Fragment Containing the Phaseolin Gene DNA Fragment and the Kanamycin Resistance Gene pKS4-KB (FIG. 7) was purified and digested with EcoRI. A 4.8 kbp fragment was isolated using 3.0 kbp EcoRI/BamHI phaseolin gene fragment ligated at the BamHI site to a 1.85 kbp DNA fragment containing the kanamycin resistance gene encoding neomycin phosphotransferase II (NPTII).

1.5 Ligation of the Phaseolin Gene to the Octopine Synthase

Figure 40:
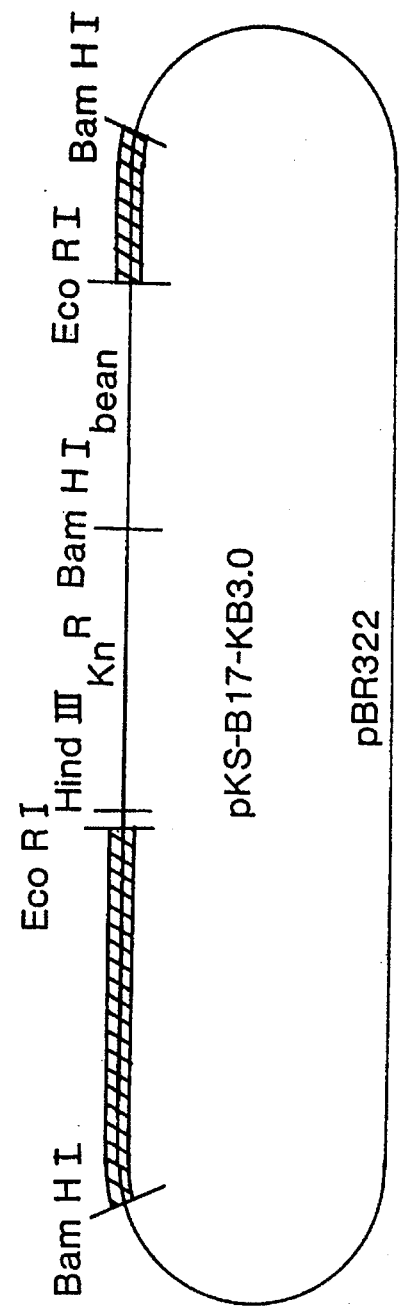
FIG. 40 illustrates a circular restriction map of pKS-B17-KB3.0. This plasmid contains the nptII and phaseolin genes on an EcoRI fragment ligated to the large EcoRI fragment of pKS169 resulting in insertion at an EcoRI site within the octopine synthase gene. Expression of an octopine synthase-phaseolin fusion protein is directed by the octopine synthase gene promoter. pBR322 is the plasmid vector.

The phaseolin/NPTII fragment was then ligated at the EcoRI sites to the EcoRI fragment described in Example 1.3. The ligated DNA was transformed into HB101 and colonies were selected on ampicillin and kanamycin. A colony named pKS-B17-KB3.0 (FIG. 40) was selected that contained a plasmid that had the correct orientation (i.e., the phaseolin gene ligated to the ocs gene in the correct direction and reading frame). This was ascertained by the restriction mapping of plasmids from a small number of colonies. DNA sequence of the appropriate region was determined to verify the construction.

1.6 Transfer of the T-DNA Fragment Containing the NPTII, Phaseolin and ocs DNA into pRK290 pRK290, a broad host range plasmid, was digested with BglII and ligated to a 9.1 kbp BamHI fragment containing the T-DNA, the NPTII gene, and the phaseolin DNA from pKS-B17-KB3.0. This was accomplished by partially digesting pKS-B17-KB3.0 with BamHI and isolating a 9.1 kbp fragment from 6 other bands from an agarose gel electrophoresis. After ligation and transformation into *E. coli* strain K802, colonies were selected on kanamycin and tetracycline. A colony was selected that had the desired restriction pattern and was labeled pKS-OS-KB3.0.

1.7 Replacement of Octopine Synthase on pTi15955 with the Octopine Synthase Phaseolin Fusion Protein Gene Using triparental mating of *A. tumefaciens* (streptomycin resistant), *E. coli* (pKS-OSI-KB3.0), and *E. coli* (pRK2013), we selected for colonies resistant to streptomycin, kanamycin, and tetracycline. One colony was mated with *E. coli* (pPH1J1). A colony was selected that is resistant to kanamycin and gentamycin. This was shown to be *A. tumefaciens* with p15955-12A, a pTi15955 that has the phaseolin gene and kanamycin resistance gene engineered into the EcoRI site of the ocs gene by restriction enzyme mapping, and filter hybridization of electrophoretically separated restriction fragments (Example 19). An analogous triparental mating is done with *A. tumefaciens* (pTiA66). Shoots transformed by the resulting plasmid, pA66-12A, are shown to contain phaseolin as described above.

1.8 Crown Gall Formation and Expression

Sunflower plants were inoculated with the engineered Ti plasmid. Crown galls were established in tissue culture. Expression was tested by running ELISAs and by filter hybridization to electrophoretically separated mRNA ("Northern blots", Example 19) RNA of the expected size was detected with hybridization probes to both the phaseolin and octopine synthase genes, and comprised about 0.5% of total poly(A) 5+4 RNA. Poly (A) 5+4 RNA isolated from galls directed the in vitro synthesis of a protein of the expected size which was precipitatable by antibodies raised against phaseolin.

EXAMPLE 2

Figure 6:
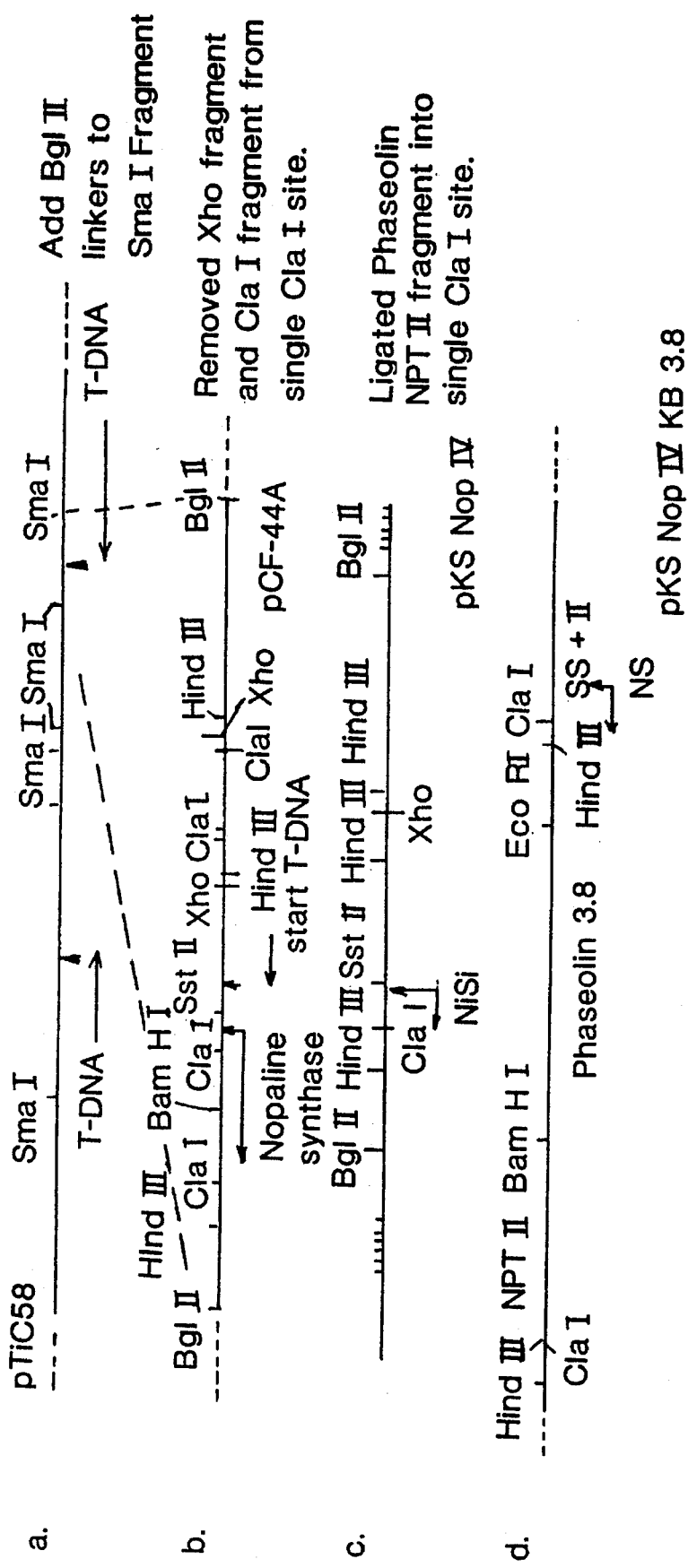
FIG. 6 illustrates the steps in the construction of pKS-NopIV-KB3.8.

A fusion protein gene similar to that taught in Example 1 is constructed from phaseolin and nopaline synthase, under control of the latter gene's promoter. It contains the nopaline synthase promoter, and encodes the first 59 amino acids of nopaline synthase (of which the last residue was synthetically added), a one amino acid junction, and all of the phaseolin structural gene except for its first 12 amino acids. Prior to the start of construction, a clone of pTiC58 T-DNA (pCF44A, FIG. 6) was sequenced from the BglII site on the extreme left through the middle HindIII site, which is outside of the T-DNA region. This included all of the nos gene (FIG. 4). The nopaline synthase sequence and reading frame were found to be as follows near a site cut by the restriction enzyme ClaI:

```
              ClaI
5'... CCA/GGA/T*CG/ATC/TCA        ...3'
3'... GGT CCT A GC*TAG ACT        ...5'
    ... Pro Gly Ser  Ile Ser      ...
         56  57  58   59  60
```

Cleavage with ClaI yields a fragment with the following end:

```
    ... CCA/GGA/T        3'
    ... GGT CCT AGC      5'
```

As stated in Example 1, the following phaseolin EcoRI site:

```
              EcoRI
    ... CTG/GG*A/ATT/CTT/TTC        ...
```

```
    ... GAC CC T TAA*GAA AAG           ...
    ... Leu Gly Ile Leu Phe            ...
        11  12  13  14  15
``` can be cleaved to yield the following structure:

```
         5'    A/ATT/CTT/TTC ... 3'
                   GAA AAG ...
```

The following two linkers

```
         a)  5' CGATCCC     3'
         b)  5' AATTGGGAT   3'
``` can be annealed to form the following structure

```
         5' CGATCCC          3'   (a
         3'     TAGGGTTAA    5'   (b
``` which can link together the DNA fragments to form the following structure:

```
              New Linker
... CCA/GGA/T*CG/ATC/CC*A/ATT/CTT/TTC           ...
... GGT CCT A GC*TAG GG T TAA*GAA AAG           ...
... Pro Gly Ser  Ile Pro Ile Leu Phe            ...
    56  57  58   59
                     13  14  15      nopaline synthase
                                     phaseolin
```

Note that the linker serves several functions: a new amino acid is introduced; part of the deleted sequence of nopaline synthase is reconstructed; two incompatible restriction sites are made compatible, and an open reading frame is preserved.

So in short, the EcoRI/BamHI restriction fragment of the phaseolin gene is ligated to the ClaI site of the nopaline synthase gene after a linker converts the EcoRI site to a ClaI site. The fusion gene contains the nopaline synthase promoter, the first 58 amino acids of nopaline synthase, a linker which reconstructs some of the nopaline synthase sequence and inserts a novel amino acid, and all of phaseolin except for the first twelve amino acid residues.

2.1 Synthesis of Linkers

The following two linkers are synthesized:

```
         a)  5' CGATCCC     3'
         b)  5' AATTGGGAT   3'
```

These are synthesized by the methods of Example 17. The oligonucleotides a) and b) are annealed together to form the structure:

```
         5' CGATCCC          3'   (a
         3'     TAGGGTTAA    5'   (b
```

Figure 5:
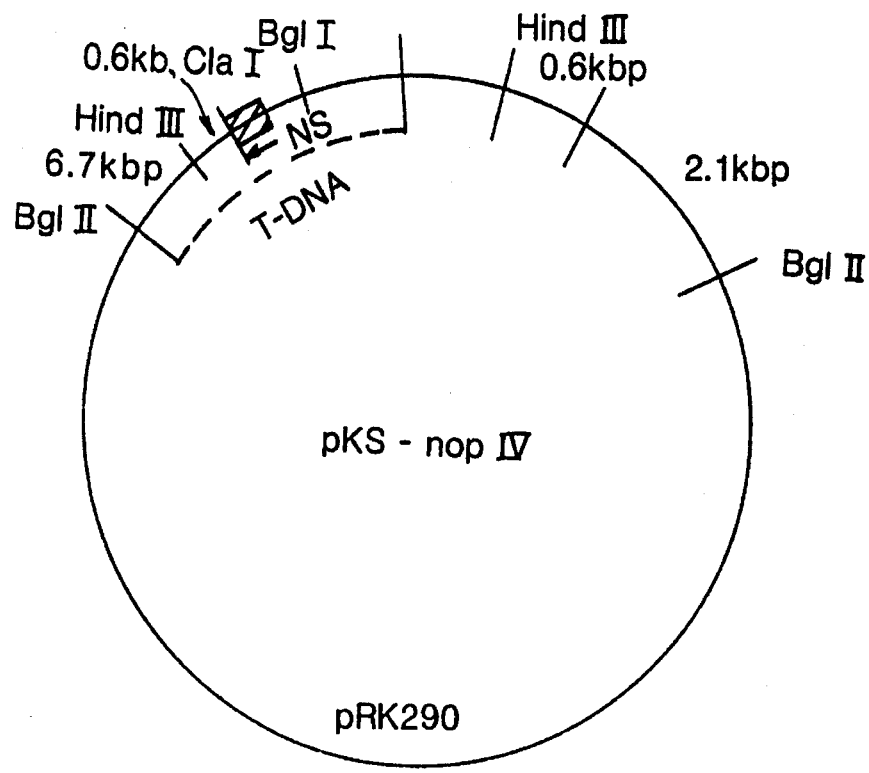
FIG. 5 illustrates pKS-nopIV. The pRK290 vector contains nopaline T-DNA-derived sequences cloned at the vector BglII site (See also FIG. 6(c)). pKS-nopIV contains a single ClaI site within the nopaline synthase gene and a single XhoI site upstream of the nopaline synthase gene. nos gene sequences (NS) are indicated by a cross-hatched box, and the direction of transcription is indicated by the arrow.

2.1 Preparation of the Shuttle Vector pKS-nopIV is pRK290 with nopaline T-DNA cloned into its BglII site. Its nopaline T-DNA contains a single ClaI site resulting from deletion between the ClaI site in nos and the ClaI site downstream outside the nos gene (FIGS. 5 and 6). pKS4-KB (FIG. 7) is purified and digested with EcoRI. The 4.8 kbp kan/bean fragment is purified by gel electrophoresis. This fragment contains the EcoRI/BamHI phaseolin DNA fragment (referred to as bean in the label kan/bean) ligated at the BamHI site to the BamHI/EcoRI fragment of the kanamycin resistance gene (kan) of Tn5.

Figure 8:
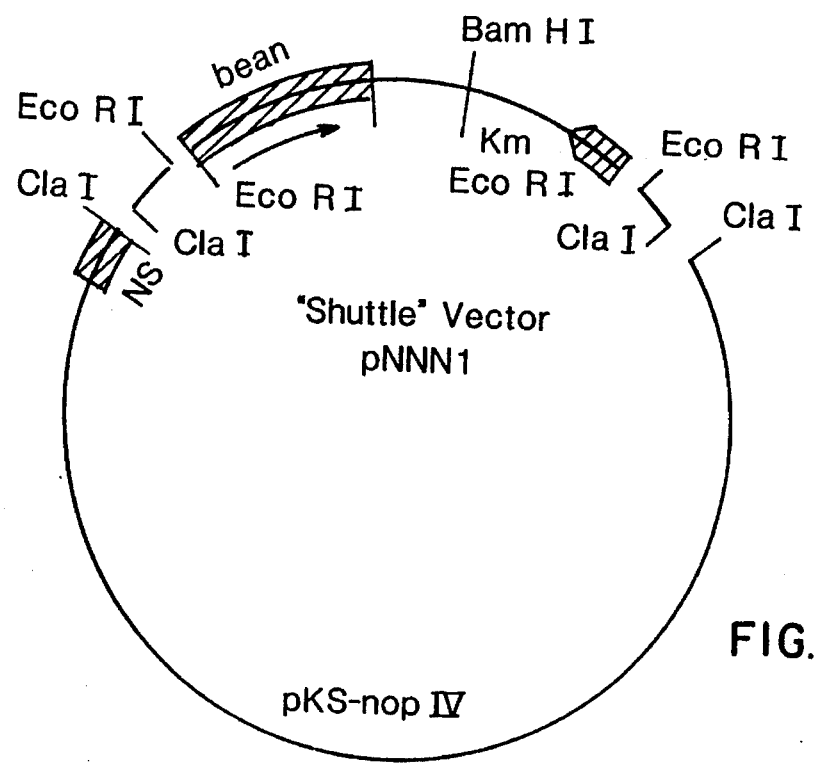
FIG. 8 illustrates the shuttle vector pNNN1. The kanamycin resistance (Km) and phaseolin genes (bean) are excised from pKS4-KB using EcoRI, linkers described in Example 2.1 are added, and the modified fragment is then ligated into ClaI-linearized pKS-nopIV to yield pNNN1.

ClaI linearized pKS-nopIV is ligated with the purifed kan/bean fragment and the linkers from Example 2.1. *E. coli* K802 is transformed and selected for kanamycin and tetracycline resistant colonies. Two orientations are present, one with phaseolin DNA ligated to the nopaline synthase gene and the other with the kanamycin resistance gene ligated next to the nopaline synthase gene. Restriction site mapping is used to determine which cells contain a plasmid, pNNN1, having the desired orientation as shown in FIG. 8.

2.3 Replacement of the Nopaline Synthase Gene on pTiC58 with the Modified Phaseolin A triparental mating (see Background-Shuttle Vectors) with *A. tumefaciens*-strR C58, *E. coli* (pRK2013), and *E. coli* (pNNN1) is used to insert the construction into a Ti plasmid. *A. tumefaciens* cells resistant to streptomycin, kanamycin and tetracycline are selected. The selected transformants are mated with *E. coli* (pPH1J1) and colonies resistant to kanamycin and gentamycin are selected.

2.4 Crown Gall Formation and Expression

Sunflowers are inoculated and crown galls are established in tissue culture. Expression is tested by ELISA and hybridization to mRNA as described in Examples 17 and 20.

EXAMPLE 3

The aim of this example is to reconstruct the complete phaseolin gene coding sequence from the ATG translational start signal to the EcoRI site which can then be ligated to the remainder of the structural gene. A ClaI site will be constructed at the 5' end so the gene can be easily recovered. The following two oligonucleotide sequences will be synthesized:

```
  a)  5' AATTCCCAGCAACAGGAGTGGAACCCTTGCTCTCATCAT           3'
  b)  5' CGATGATGAGAGCAAGGGTTCCACTCCTGTTGCTGGG             3'
```

These can be reannealed to form the following structure:

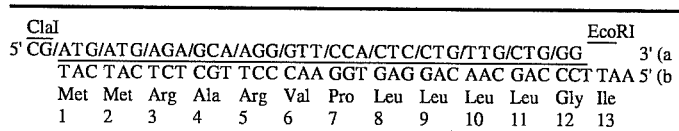

As stated in Example 1, the following phaseolin EcoRI site:

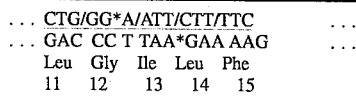

can be cleaved to following structure:

Ligation of this end to the synthetic double-stranded oligonucleotide described above results in a structural gene encoding a complete phaseolin polypeptide, with ClaI sticky-ends immediately ahead of the start of the coding sequence.

3.1 Synthesis of Linkers

The following two linkers are synthesized by the method of Example 17:

| | | |
|---|---|---|
| a) | 5' AATTCCCAGCAACAGGAGTGGAACCCTTGCTCTCATCAT | 3' |
| b) | 5' CGATGATGAGAGCAAGGGTTCCACTCCTGTTGCTGGG | 3' |

They were annealed to form the following structure:

| | | |
|---|---|---|
| 5' CGATGATGAGAGCAAGGGTTCCACTCCTGTTGCTGGG | 3' | (b |
| 3' TACTACTCTCGTTCCCAAGGTGAGGACAACGACCCTTAA | 5' | (a |

3.2 Construction of Complete Phaseolin Gene and Kanamycin Resistance Gene Cloned in pKS-nopIV ClaI linearized pKS-nopIV is ligated with reannealed linker from Example 3.1 and purified kan/bean EcoRI fragment from KS4-KB (see Example 2.2). E. coli K802 is transformed and selected for tetracycline and kanamycin resistant colonies. Again, though two orientations are possible, only one is the phaseolin gene ligated next to the nopaline synthase gene. The correct orientation is selected after restriction endonuclease mapping the clones.

3.3 Crown Gall Formation and Expression

The homologous recombination and crown gall tissue culture isolation is performed as outlined in Example 21, and the testing of crown gall tissues for phaseolin gene expression is as in Examples 19 and 20.

EXAMPLE 4

The purpose of this construction is to teach how to construct a Shuttle Vector to be used in pTi system for expressing foreign genes in crown gall cells, the foreign gene being under control of the nos promoter, part of which is chemically synthesized, and is missing codons for the nopaline synthase gene. Prior to the start of construction, a clone of pTiC58 T-DNA (pCF44A) was sequenced to discover the nos promoter (FIG. 4).

4.1 Isolation of the 5' Portion of the nos Promoter pCF44A was cut with XhoI, religated, and labeled pCF44B, which has the following structure:

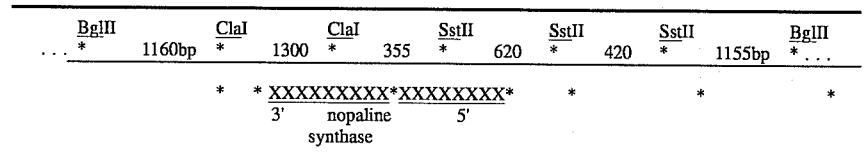

This new plasmid was then deleted for the SstII fragments. The resulting plasmid, pCF44C

| BglII | | ClaI | | | ClaI | | SstII | | BglII | |
|---|---|---|---|---|---|---|---|---|---|---|
| ... * | 1160 | * | | 1300 | * | 355 | * | 1155 | * ... | |
| * | | * | | | XXXXXXXXXXXXXXXX*XXXXXXXXX* | | | | * | |
| | | | | | 3' | nopaline | | 5' | | |
| | | | | | | synthase | | | | | was digested with BglII, and a 3.6 kbp fragment was inserted into the BglII site of pRK290. A colony selected for hybridization to T-DNA in a Grunstein-Hogness assay was labeled pKS-nopV, digested with ClaI, and religated, forming pKS-nopVI.

| BglII | | ClaI | | SstII | | BglII | |
|---|---|---|---|---|---|---|---|
| ... * | 1160bp | * | 355 | * | 1155bp | * ... | |
| * | | | *XXXXXXXXX* | | | * | |
| | | | 5' | | | | |

This was digested with ClaI and SstII, giving a 22 kbp linearized vehicle and a 355 bp fragment. These were easily separated by centrifugation through a salt gradient. After the small fragment was digested with HinfI, the 149 bp SstII/HinfI and the 208 bp ClaI/HinfI fragments were isolated by gel electrophoresis.

4.2 Synthesis of Linkers

The following two linkers were synthesized by the method of Example 17:

| a) | 5' AGTCTCATACTCACTCTCAATCCAAATAATCTGC<u>C</u>ATGGAT | 3' |
| b) | 5' CGATCCATGGCAGATTATTTGGATTGAGAGTGAGTATGAG | 3' |

They are annealed together to form the following structure:

| 5' AGTCTCATACTCACTCTCAATCCAAATAATCTGC<u>C</u>ATGGAT | 3' (a) |
| 3'     GAGTATGAGTGAGAGTTAGGTTTATTAGAC<u>G</u>GTACCTAGC | 5' (b) |

This sequence has a HinfI site on the left, and NcoI and ClaI sites on the right. An alternate sequence will have a BclI site between the NcoI and ClaI sites. The sequence is identical to that found in T-DNA except for the underlined bases, which replace an A-T base pair with a C-G base pair.

4.3 Assembly of pNNN2

Figure 9:
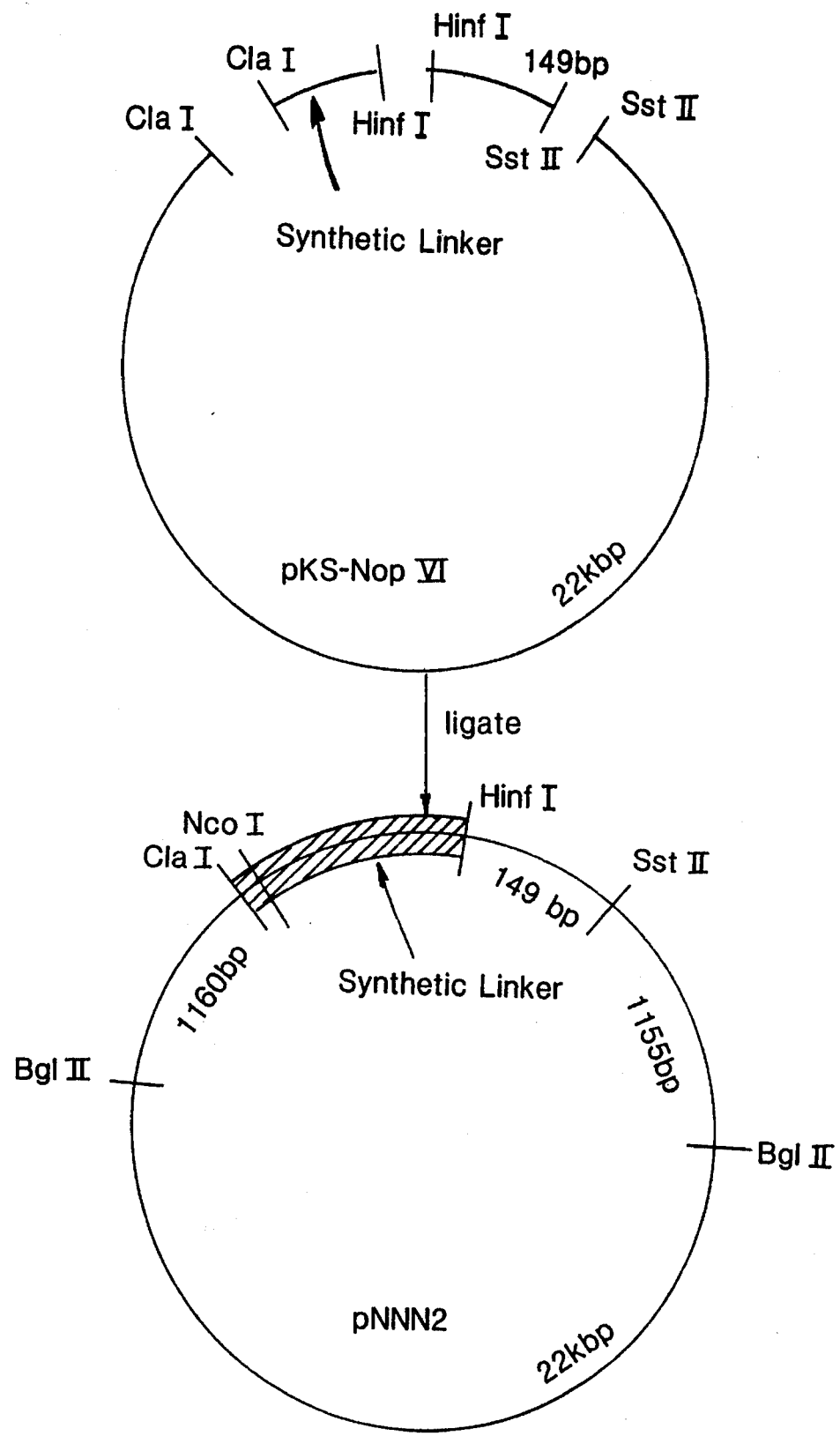
FIG. 9 illustrates the modification of T-DNA sequences comprising the nos promoter to give pNNN2. nos promoter sequences are excised from pKS5-nopVI (see Example 4.1) on a 355 bp ClaI/SstII fragment. This fragment was then digested with HinfI to yield 149 bp SstII/HinfI and 208 bp ClaI/HinfI fragments. The 22 kbp portion of pKS-nopVI is then ligated with the 149 bp SstII/HinfI fragment and the synthetic linker which replaces the natural 208 bp ClaI/HinfI fragment, to yield pNNN2. The cross-hatched portion of pNNN2 represents the synthetic linker which replaces the natural ClaI/HinfI portion of the nos promoter.

The 22 kbp ClaI/SstII vehicle is ligated as shown in FIG. 9 with the 149 bp SstII/HinfI fragment and the synthetic linker, forming the following structure:

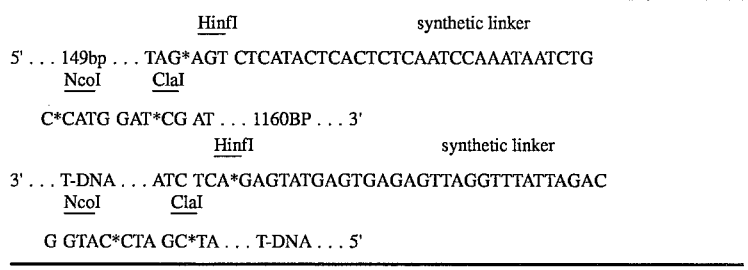

4.4 Insertion and Expression of a Phaseolin Gene pNNN2, the plasmid constructed in Example 4.3 (FIG. 9) is cut with ClaI, mixed with the ClaI/EcoRI linker synthesized in Example 3.1 and electrophoretically purified EcoRI/ClaI kan/bean fragment from pKS4-KB, ligated, transformed, isolated, and restriction mapped. The appropriate plasmid, pNNN4, is transferred and tested for expression as described in Examples 19, 20 and 21.

4.5 Insertion and Expression of a Phaseolin Gene Lacking Expressions

The procedure outlined in Example 4.4 is repeated with the substitution for pKS4-KB of a pcDNA31 or pMC6-cDNA-derived analog of pKS4-KB. (See Example 9).

4.6 Insertion and Expression of a Phaseolin cDNA

This construction is analogous to Example 10 in its use of cDNA, a single stranded PstI linker, and the PstI kan fragment, and is analogous to Examples 4.1, 4.2 and 4.3 in the use of the semisynthetic nos promoter. Characterization, transfer and testing of expression is as described in Example 4.4.

pNNN2, the plasmid constructed in Example 4.3 (FIG. 9) is cut with ClaI, mixed with and ligated to the ClaI/EcoRI linker synthesized in Example 3.1, the electrophoretically purified 1.7 kbp EcoRI/PstI bean fragment isolated from pKS4-KB, the electrophoretically purified PstI Tn5 kan fragment, and the single-stranded ClaI/PstI linker 5'CGAATT3', previously synthesized by the method of Example 17.

EXAMPLE 5

Figure 10A:
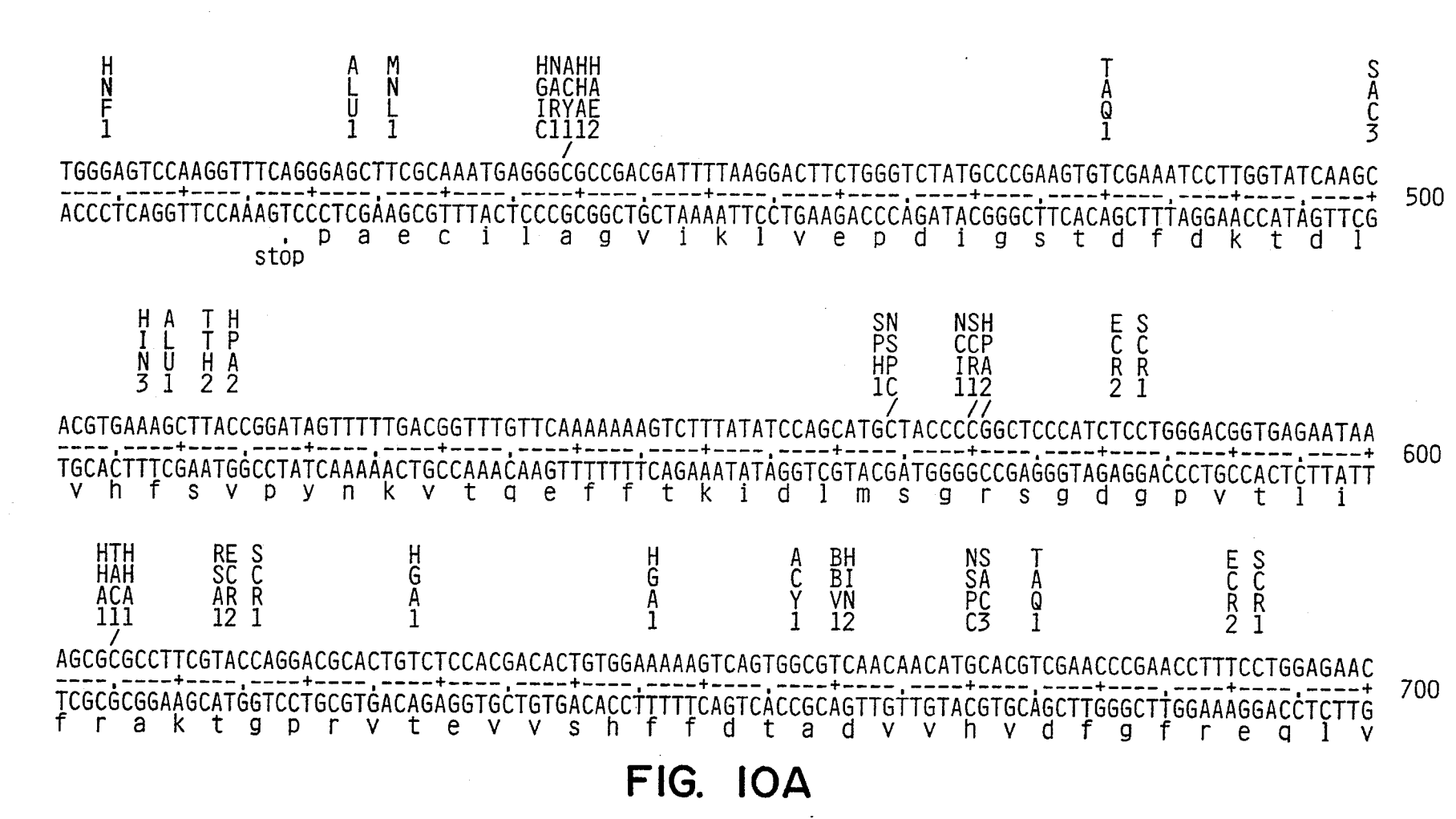
Figure 10B:
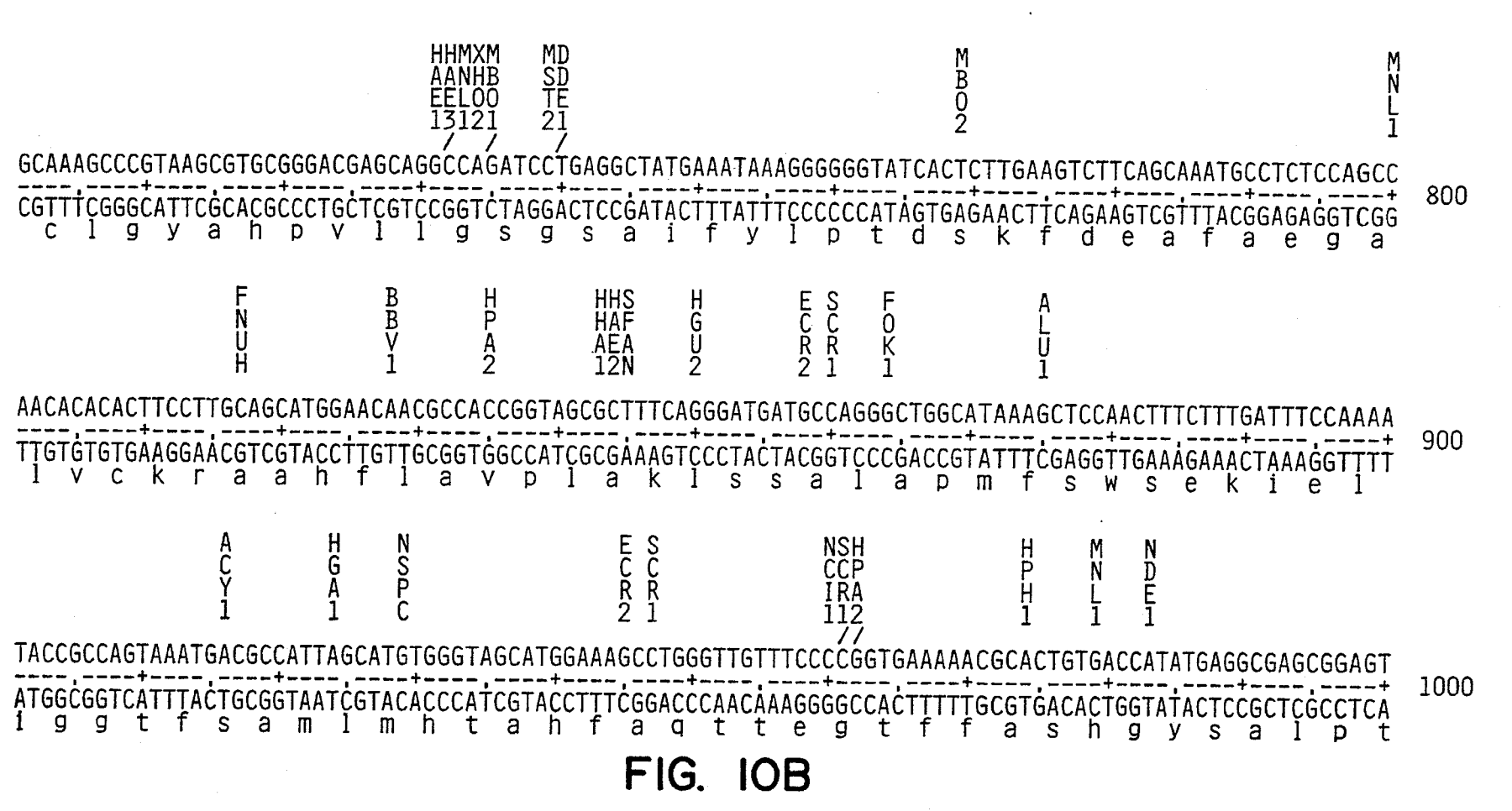
Figure 10C:
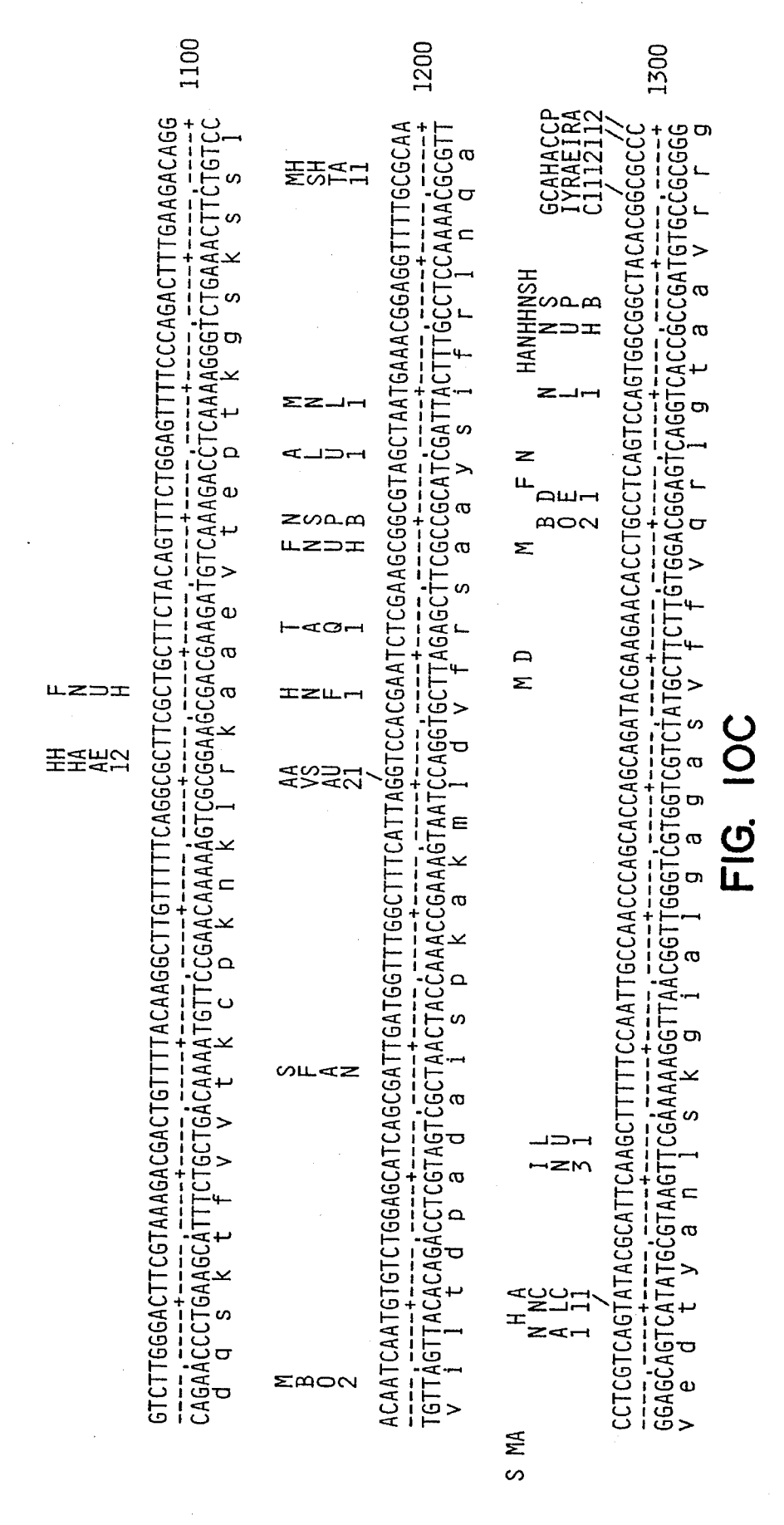
Figure 10D:
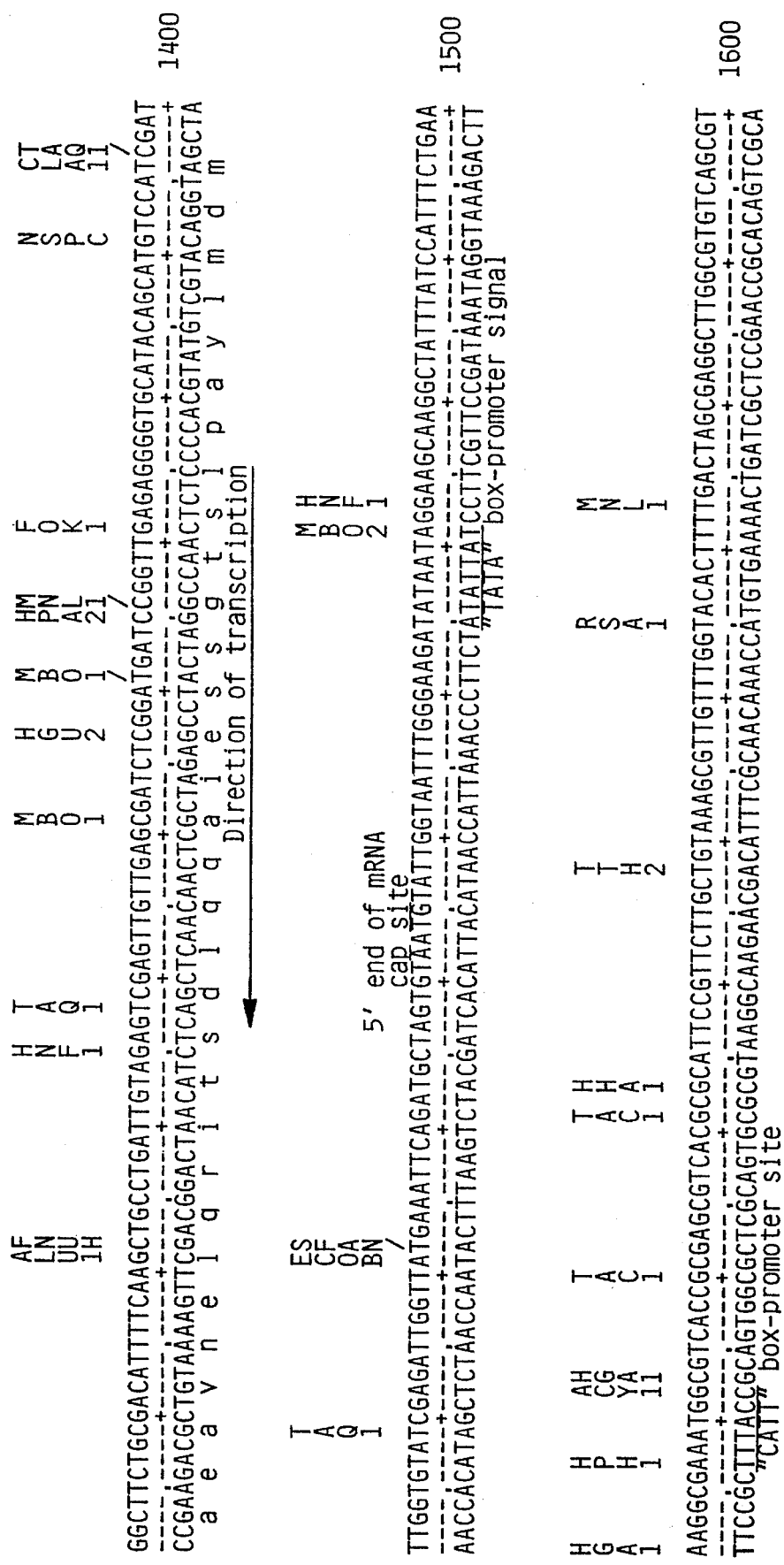
FIG. 10A–10B present the nucleotide sequence of the pTi15955 T-DNA "1.6 transcript gene," which directs the synthesis of the mRNA which is labeled "1.6" in FIG. 1. Restriction sites are written vertically over the DNA sequence. The "TATA box" promoter signal is underlined.
Figure 11:
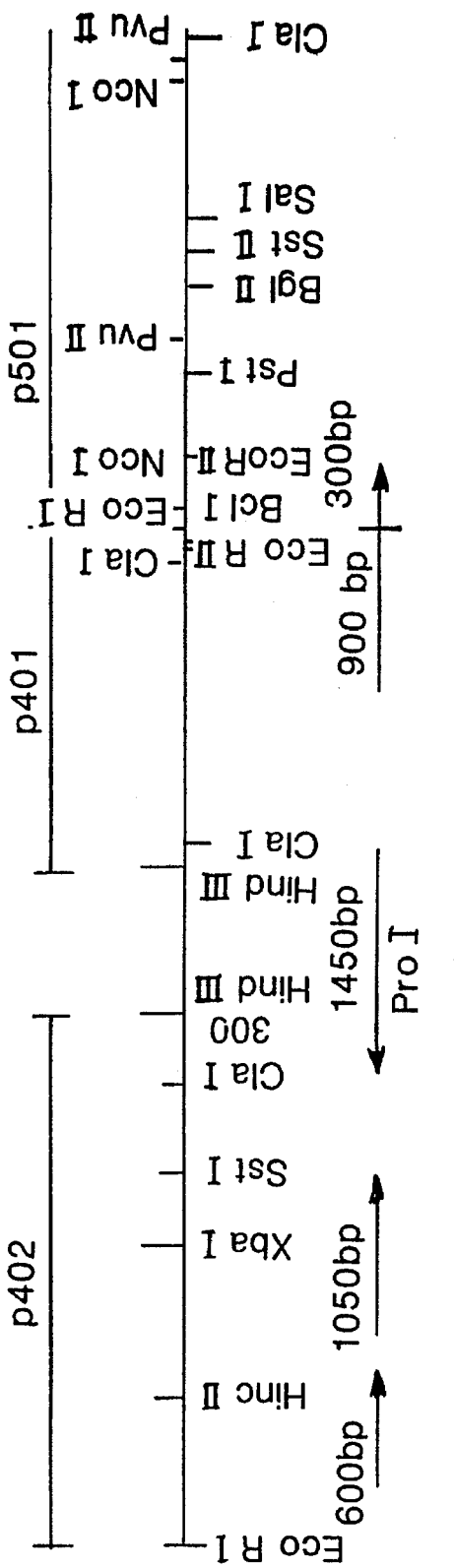
FIG. 11 illustrates a partial restriction map of pTi15955, including the regions covered by subclones p401, p402 and p501, and the region which directs the synthesis of the "1.6 transcript", which is actually 1450 bases in length. Sequencing allowed the determination that the transcript is actually 1450 bases long, and the region of the T-DNA from which this transcript is derived is located in the figure.

The purpose of this construction is to ligate the phaseolin gene from the EcoRI site to BamHI site, into the active T-DNA gene that lies across the HindIII sites on p403. The mRNA of this T-DNA gene is labeled 1.6 on the map, shown in FIG. 1, and 1450 bp and ProI in the map shown in FIG. 11. This T-DNA gene is referred to herein as the "1.6 transcript" gene. The sequence (see FIG. 10) was determined from the HindIII site of p401 past the ClaI site to its right (see FIG. 11). There is an open reading frame that starts between the HindIII and ClaI site going toward the HindIII site (see the 1450 base mRNA mapped in FIG. 11). The ClaI site is in the untranslated leader of the mRNA of the gene spanning the HindIII sites. We created a promoter vehicle by cutting out the ClaI fragment in the middle of p403. This is possible because the internal ClaI sites are not methylated in some E. coli strains, whereas the ClaI site next to the EcoRI site is methylated.

The phaseolin gene is then ligated into the ClaI site, bringing with it an ATG. This can be accomplished by using pKS4-KB. The base sequence from the ClaI site of pBR322 through the EcoRI site of phaseolin is as follows:

| ClaI | EcoRI |
|---|---|

5'... AT*C/G AT/GAT/AAG/CTG/CTG/TCA/AAC/ATG/AG*A/ATT/CTT/TTC ... 3'

3'... TA G C*TA CTA TTC GAC GAC AGT TTG TAC TC T TAA*GAA AAC ... 5'
                               Met Arg/Ile Leu Phe ...
                               13 14 15
                  ... derived from pBR322/phaseolin ...

Note the open reading frame and the ATG. There are 18 bp between the ClaI site and the translational start signal (ATG). This compares to 12 bp from the ClaI site to the start of the T-DNA gene:

| ClaI |
|---|

5'... AT*CG A/TGG/ACA/TGC/TGT/ATG ... 3'
3'... TA GC*T ACC TGT ACG ACA TAC ... 5'
              Met ...

Again, note the open reading frame and the ATG. Thus, ligation into the ClaI site of the promoter clone should create an active phaseolin gene in the T-DNA. The phaseolin gene has a substitution of 2 amino acids for the naturally occuring amino terminal 12 residues.

5.1 Construction of a Promoter Vehicle pKS111, which is a pRK290 clone corresponding to the T-DNA clone p403 (see FIGS. 1, 12), was digested with ClaI and then religated. The ligation mix was transformed into K802 and transformants were selected for tetracycline resistance. Plasmids were isolated by doing "minipreps" (plasmid preparations from small volume cell cultures) and restriction maps were obtained to prove the structure. The new vehicle, pKS-proI, cannot be digested by HindIII, but can be linearized by ClaI (FIG. 12). pKS-proI was purified and linear molecules were produced by digestion with ClaI.

5.2 Ligation of a Partial Phaseolin Gene to a Kanamycin Resistance

Figure 17:
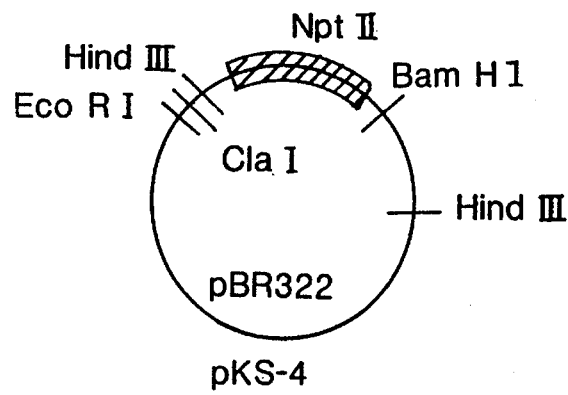
FIG. 17 illustrates a circular restriction map of pKS-4. The HindIII/BamHI fragment of Tn5 (from pRZ102) comprising the kanamycin resistance gene (nptII), which is indicated by cross-hatching.

A 3.0 kbp fragment containing extensive 3' flanking sequences and all but the extreme 5' coding sequences of the phaseolin gene was obtained by elution from an agarose gel after electrophoresis of an HindIII and BamHI digest of p7.2 (FIG. 13), a pBR322 subclone of the phaseolin genomic clone 177.4 whose construction is described in Example 6.1. This was mixed with and ligated to a 3.0 kbp kanamycin resistance HindIII/BamHI fragment similarly isolated from pKS4 (FIG. 17), and HindIII-linearized pBR322. After restriction mapping of plasmids isolated from ampicillin resistant transformants, a plasmid having the structure shown in FIG. 7 was labeled pKS4-KB.

5.3 Purification of the kan/bean Fragment from pKS4-KB pKS4-KB (FIG. 7) was digested with ClaI and the 4.9 kbp fragment purified by agarose gel electrophoresis.

5.4 Ligation of ClaI kan/bean Resistance Gene into ClaI Digested pKS-ProI pKS-proI is linearized by digestion with ClaI and the kanamycin resistance gene/bean fragment from Example 5.3 are ligated together and transformed into K802. Kanamycin resistant transformants are selected and plasmids isolated by "minipreps" are restriction mapped to detect one having the proper orientation. The plasmid is labeled pKS-ProI-KB (FIG. 14).

5.5 Transformation and Expression

Cells containing pKS-proI-KB are mated with Agrobacterium cells containing pTi15955 or pTiA66 or other appropriate TIP plasmids. After selection of recombinants with kanamycin, plants are inoculated and crown galls are established in tissue culture. Testing for the synthesis of phaseolin is as described in Examples 19 and 20.

EXAMPLE 6

This example teaches manipulations of a gene for phaseolin, the major seed storage protein of the bean *Phaseolus vulgaris* L., preparatory to further manipulations which insert the phaseolin gene into vectors described in various other examples.

6.1 Subcloning of a Phaseolin Gene

Figure 15:
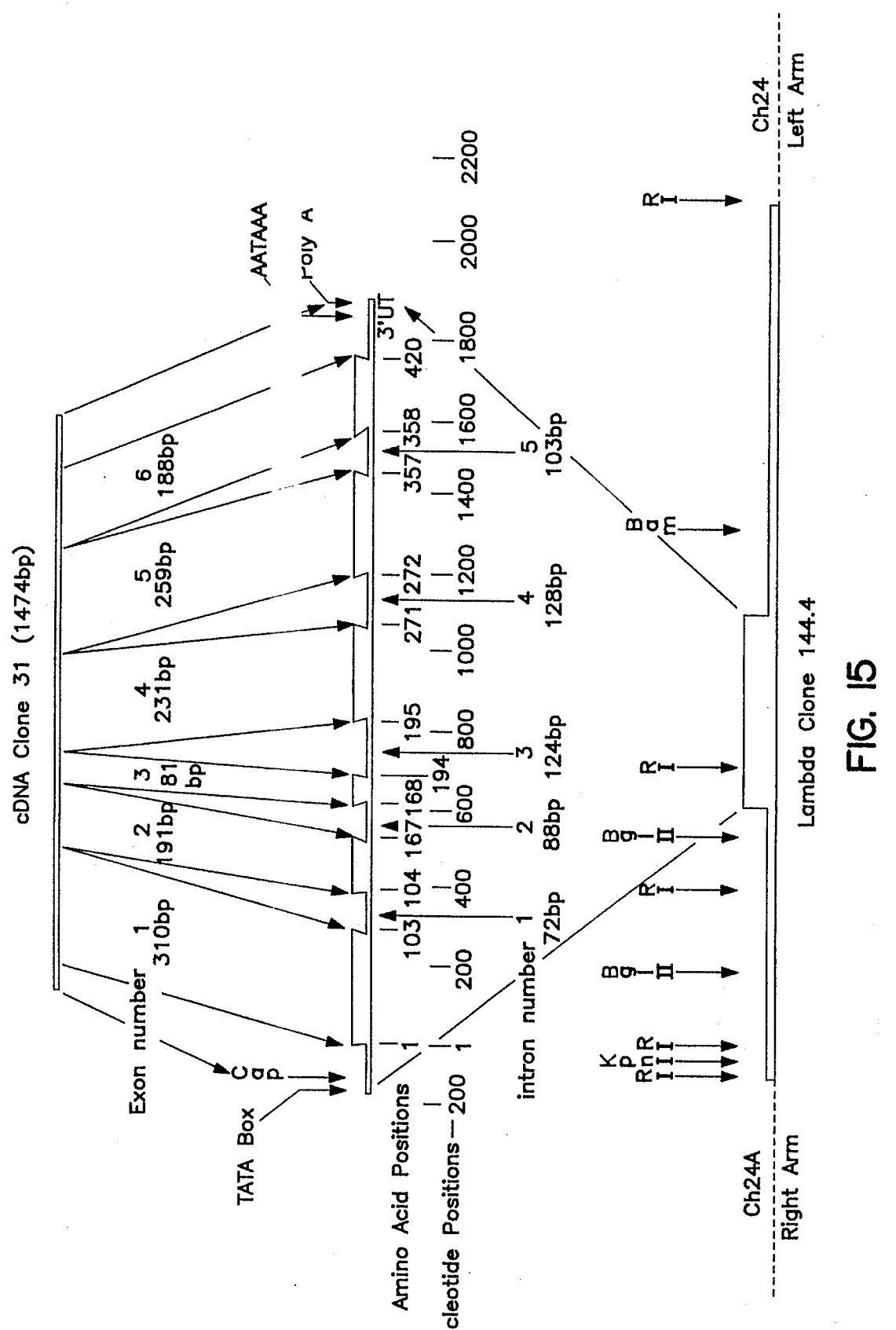
FIG. 15 illustrates the structures of the cDNA and genomic clones comprising the phaseolin gene.
Figure 16:
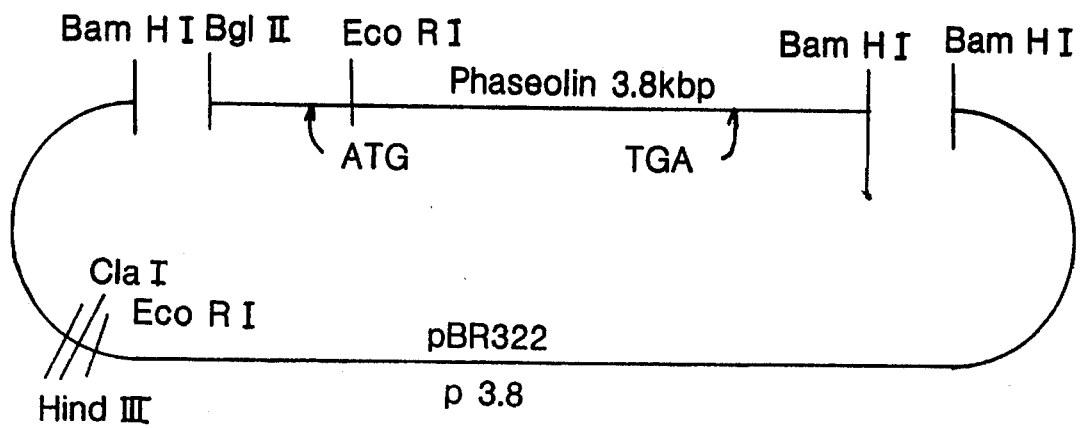
FIG. 16 illustrates a circular restriction map of p3.8. p3.8 consists of a 3.8 kbp BamHI/BglII fragment of bean DNA from Charon clone 177.4 inserted at the BamHI site of pBR322. The start and stop codons of the phaseolin gene are indicated by ATG and TGA, respectively. For convenience, the junctions of vector and insert DNAs are not closed.

A genomic clone of phaseolin in a Charon 24A AG-PVPh177.4 (or 177.4; S. M. Sun et al. (1981) Nature 289:37–41, J. L. Slightom et al. (1983) Proc. Natl. Acad. Sci. USA 80; FIG. 15) was digested with BglII and BamHI. The 3.8 kbp fragment carrying the phaseolin gene and its flanking sequences, isolated by agarose gel electrophoresis, was mixed with and ligated to BamHI-linearized pBR322. The mixture was transformed into HB101, and colonies resistant to ampicillin and sensitive to tetracycline were selected. Plasmid isolated from these clones was restriction mapped. A plasmid having the structure shown in FIG. 16 was selected and labeled AG-pPVPh3.8 (or alternatively, p3.8). The ligation of BglII and BamHI sites with each other inactivates both sites.

Another subclone of 177.4 was constructed by digestion with EcoRI, isolation of a 7.2 kbp fragment containing extensive 3' flanking sequences and all but the extreme 5' end of the phaseolin gene, and isolated after ampicillin selection of HB101 transformants were restriction mapped. A plasmid having the insert oriented so that the HindIII site of pBR322 was adjacent to the 5' end of the phaseolin gene and distal to the 3' untranslated region was labeled AG-pPVPh7.2 (or p7.2; FIG. 13; Sun et al. and Slightom et al., supra).

Figure 18:
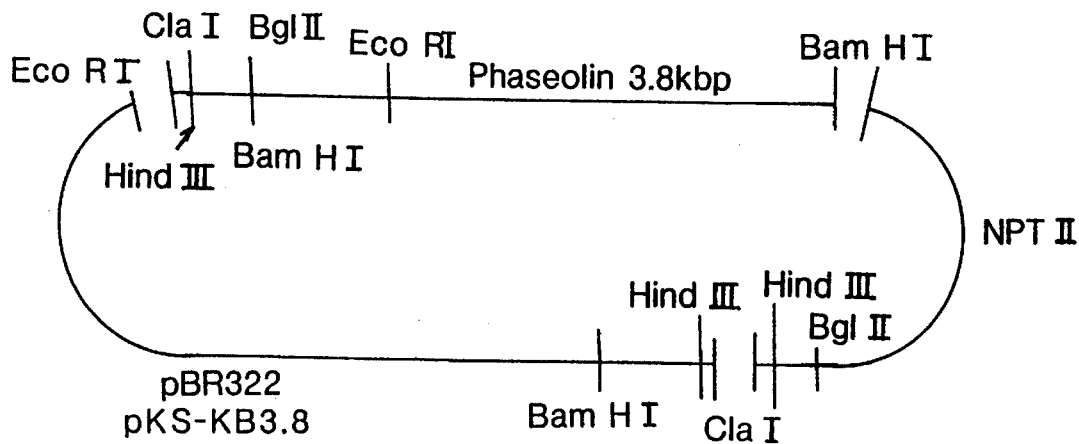
FIG. 18 illustrates a restriction map of the components pKS-KB3.8. Construction was done by ligating ClaI-linearized pBR322 with the 4.2 kbp ClaI/BamHI fragment of p3.8 comprising the phaseolin gene and a ClaI/BamHI fragment of pKS4 comprising the nptII gene. For the convenience of the reader, the components of pKS-KB3.8 are not shown ligated together.

6.2 Cloning and Isolation of a Kanamycin Resistance Gene pRZ102 (R. A. Jorgenson et al. (1979) Molec. Gen. Genet. 177:65–72), a ColE1 plasmid carrying a copy of the transposon Tn5, was digested with BamHI and HindIII, mixed with pBR322 previously linearized with the same two enzymes, ligated, and transformed into K802. Plasmids, isolated from transformants selected for resistance to both ampicillin and kanamycin, were restriction mapped and one having the structure shown in FIG. 18 was labeled pKS-4.

6.3 Linkage of the Phaseolin Gene with a Kanamycin Resistance p3.8 was digested with ClaI and BamHI, and a 4.2 kbp fragment containing the phaseolin gene and some pBR322 sequences was isolated by agarose gel electrophoresis. This was mixed with a ClaI/BamHI fragment of Tn5 carrying a kanamycin resistance (neomycin phosphotransferase II) gene from pKS4 (FIG. 17) and pBR322 which had been linearized with ClaI. The mixture was ligated and transformed into K802. After selection of colonies resistant to ampicillin and kanamycin, plasmids were isolated and restriction mapped. A colony having the structure shown in FIG. 18 was labeled pKS-KB3.8.

The construction of another useful plasmid, pKS4-KB, is described in Example 5.2.

EXAMPLE 7

This example is analogous to the construction described in Example 5, except for the substitution of a cDNA clone for the genomic clone of phaseolin. This construction will result in a gene lacking introns.

7.1 Construction of PKS4-KB2.4 (Analogous to pKS4-KB)

Figure 20:
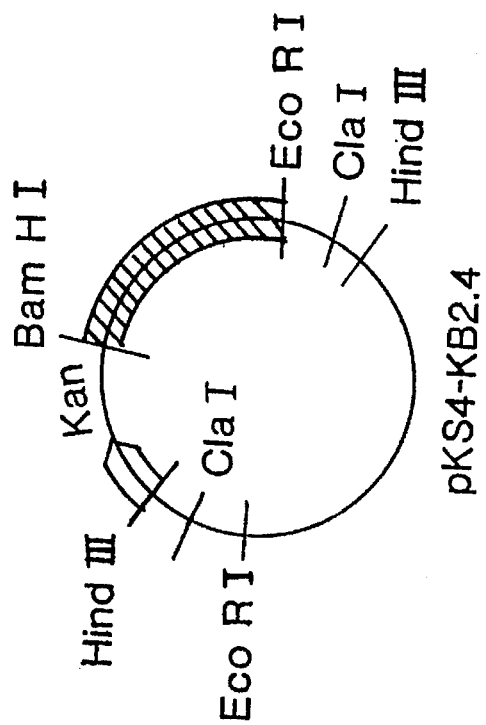
FIG. 20 illustrates a circular map of pKS4-KB2.4. To construct pKS4-KB2.4, EcoRI-linearized pBR322 was ligated with the 2.4 kbp EcoRI/BamHI fragment of pMC6 comprising the phaseolin gene, indicated by cross-hatching, and the 1.9 EcoRI/BamHI fragment of pKS4 comprising the nptII gene.
Figure 19:
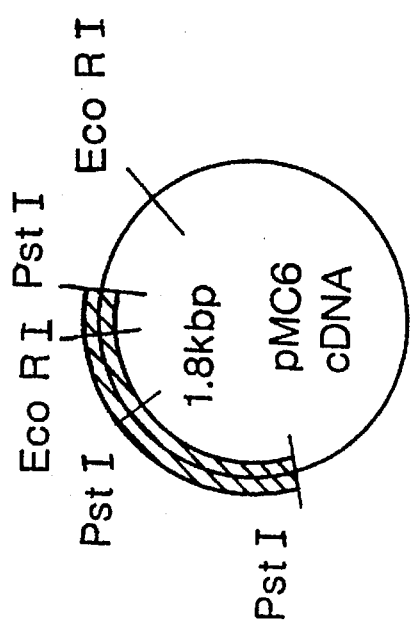
FIG. 19 illustrates a circular map of pMC6. The cross-hatched region indicates the phaseolin cDNA sequence cloned as a PstI fragment.

After pMC6 (FIG. 19) is digested with EcoRI and BamHI, a 2.4 kbp phaseolin cDNA fragment is isolated by centrifugation through a salt gradient or gel electrophoresis. A 1.9 kbp fragment containing a gene for kanamycin resistance is purified from a EcoRI and BamHI digest of pKS4 (FIG. 17), mixed with the cDNA fragment and EcoRI-linearized pBR322, ligated, and transformed into K802. Colonies are selected for kanamycin resistance, and after plasmid isolation and restriction mapping, a plasmid as shown in FIG. 20 is labeled pKS4-KB2.4.

Figure 12:
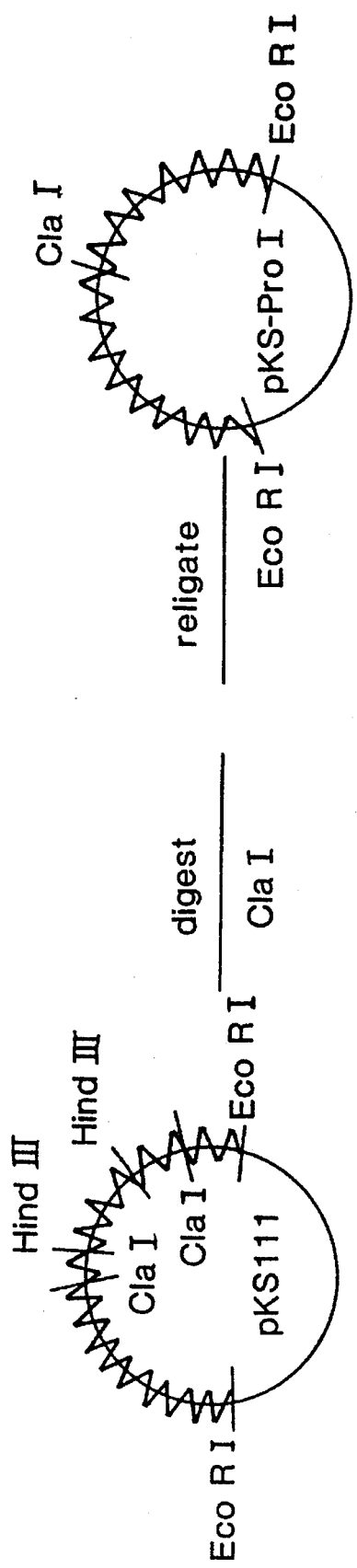
FIG. 12 illustrates the modification of pKS111 to give pKS-ProI. The jagged portion represents the EcoRI T-DNA insert and the single thin line represents the pRK290 vector sequences in both plasmids. pKS111 was digested with ClaI to remove the ClaI fragment internal to the T-DNA, and religated to yield pKS-ProI, which has a single ClaI site.

7.1 Ligation of the ClaI kan/bean DNA into ClaI Digested pKS-ProI pKS4-KB2.4 is digested with ClaI and ligated with ClaI-linearized pKS-ProI (FIG. 12). After transformation, selection, plasmid isolation and characterization, the desired construction, having the phaseolin sequences adjacent to the T-DNA promoter, is transferred to a Ti plasmid. Inoculation and testing is as described in Examples 19, 20 and 21.

EXAMPLE 8

This example teaches a method of removing the introns from a gene. This is the same as placing a cDNA in a genomic environment. Restriction enzyme sites are found, or created by site specific mutagenesis, in exons on both the 5' and 3' extremities of the unprocessed transcript. These sites exist in both the genomic clones and cDNA. The intervening intron-containing DNA can be removed from the genomic clone and be replaced with the corresponding intronless cDNA clone fragment spanning the two sites. The reverse operation is also possible: intron-containing genomic sequences can be placed in a cDNA environment. One inserts an internal fragment of the genomic clone into a corresponding gap cut out of a cDNA clone. This latter strategy is analogous, though often technically more difficult as the introns may contain sites susceptible to the enzymes chosen to create the exchanged fragment. This difficulty can be overcome by careful selection of conditions of partial digestion and by purification of the desired fragment by agarose gel electrophoresis. Further elaborations of this strategy include the manipulation of individual introns within a gene while leaving other introns and exons unaffected, and the stepwise exchange of sequences when inconvenient intervening restriction sites are present within introns as discussed above.

Figure 21:
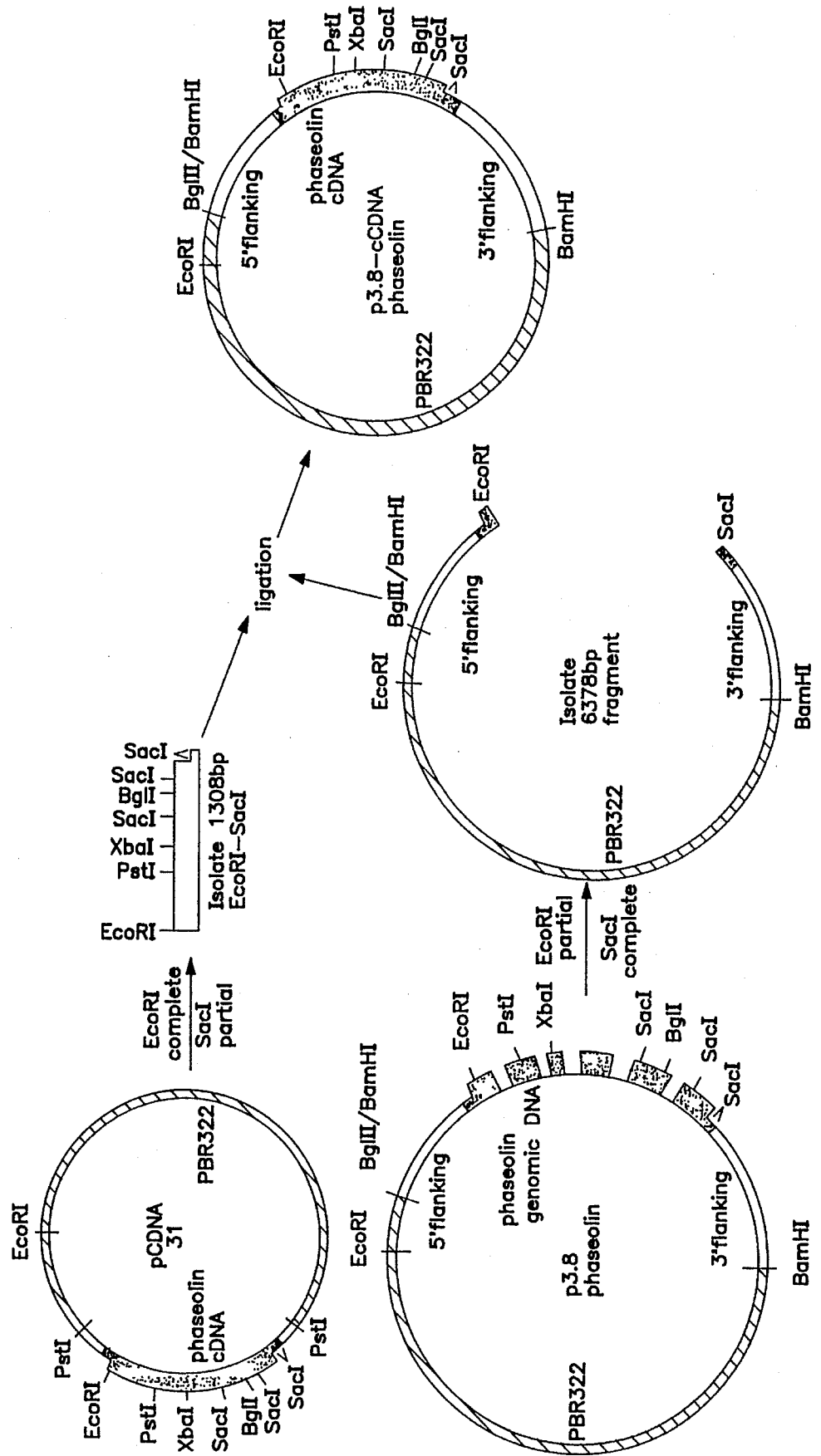
FIG. 21 illustrates the starting plasmids and steps used in making p3.8-cDNA. A 6.4 kbp SacI/EcoRI fragment containing vector sequences and the phaseolin gene 5'- and 3'-ends of the coding sequence and associated flanking sequences prepared from pcDNA31 was ligated with an approximately 1.3 kbp SacI/EcoRI fragment from p3.8 containing internal coding sequences of the phaseolin gene. pBR322 sequences are indicated by cross-hatching, phaseolin coding sequences are solid and the phaseolin noncoding sequences are open.

8.1 Replacement of a Fragment Containing Phaseolin's Introns with cDNA p3.8, a plasmid clone of the phaseolin gene and its flanking sequences, was digested respectively partially and to completion with EcoRI and SacI, and a 6.4 kbp fragment, containing the pBR322 vector and both the 5' and 3' ends of the gene, was isolated by agarose gel electrophoresis. pcDNA31, a pBR322 plasmid clone of cDNA made from phaseolin mRNA, was digested respectively partially and to completion with SacI and EcoRI, and a 1.33 kbp fragment, containing the entire phaseolin cDNA except for sequences at the extreme 5' and 3' ends, was isolated by agarose gel electrophoresis. These two fragments were ligated together and transformed into HB101. After selection of colonies, growth of cells, and plasmid isolation, restriction mapping identified a plasmid having the desired structure. This plasmid was labeled p3.8-cDNA (FIG. 21).

8.3 Use of p3.8-cDNA

Note that p3.8-cDNA can substitute for the genomic DNA source, e.g., p3.8, used in other Examples and that when so used will result in analogous constructions differing in that they are lacking introns. Alternatively, this strategy can be used to remove introns from constructions already made.

EXAMPLE 9

This example teaches the expression of an intronless gene. The phaseolin cDNA is prepared as described in Example 8, but a gene that naturally lacks introns could also be used.

An analogous construction to those taught in Examples 7 and 8 are used. pKS4-KB and pMC6 are digested with EcoRI and SacI as taught in Example 7 and as described there, the cDNA insert is ligated into the pKS4-KB fragment containing the vector and the 5' and 3' extremities of the phaseolin gene. The new plasmid, pKS4-KBc, is used in constructions in an analogous manner to pKS4-KB.

EXAMPLE 10

The purpose of this example is to teach the placement within T-DNA of the cDNA for a *Phaseolus vulgaris* lectin under the control of a T-DNA gene promoter, the transfer of this construction to a plant cell, and the detection of this construction's expression within plant tissue.

This construction utilizes a single-stranded linker to connect the sticky-ends resulting from digestion with the restriction enzymes PstI and HindIII. When PstIII and HindIII sites

| PstI | HindIII |
|---|---|
| 5'... C TCCA G ... 3' | 5'... A*AGCT T ... 3' |
| 3'... G*ACGT C ... 5' | 3'... T TCGA*A ... 5' | are cleaved to form the following ends:

| PstI | HindIII | |
|---|---|---|
| 5'... CTGCA | AGCTT ... | 3' |
| 3'... G | A ... | 5' | and are mixed together in the presence of a linker of appropriate sequence

| | | |
|---|---|---|
| 5'... CTGCA | AGCTT ... 3' | |
| 3'... G | A ... 5' | + 3'ACGTTCGA5' | they can be ligated together to form the following suture:

| HindIII |
|---|
| 5'... C TGCA*AGCT T ... 3' |
| 3'... G*ACGT TCGA*A ... 5' |

Note that a HindIII site is reconstructed.

The lectin cDNA is obtained from a plasmid clone, pPVL134, ATCC39181, that was constructed by poly C-tailing double-stranded cDNA followed by insertion into PstI cut, G-tailed pBR322. This clone as described by L. Hoffman et al. (1982) Nucleic Acids Res. 10:7819–7828.

10.1 Synthesis of the Linker

The linker 5'AGCTTGCA3' is synthesized by the method of Example 17.

Figure 22:
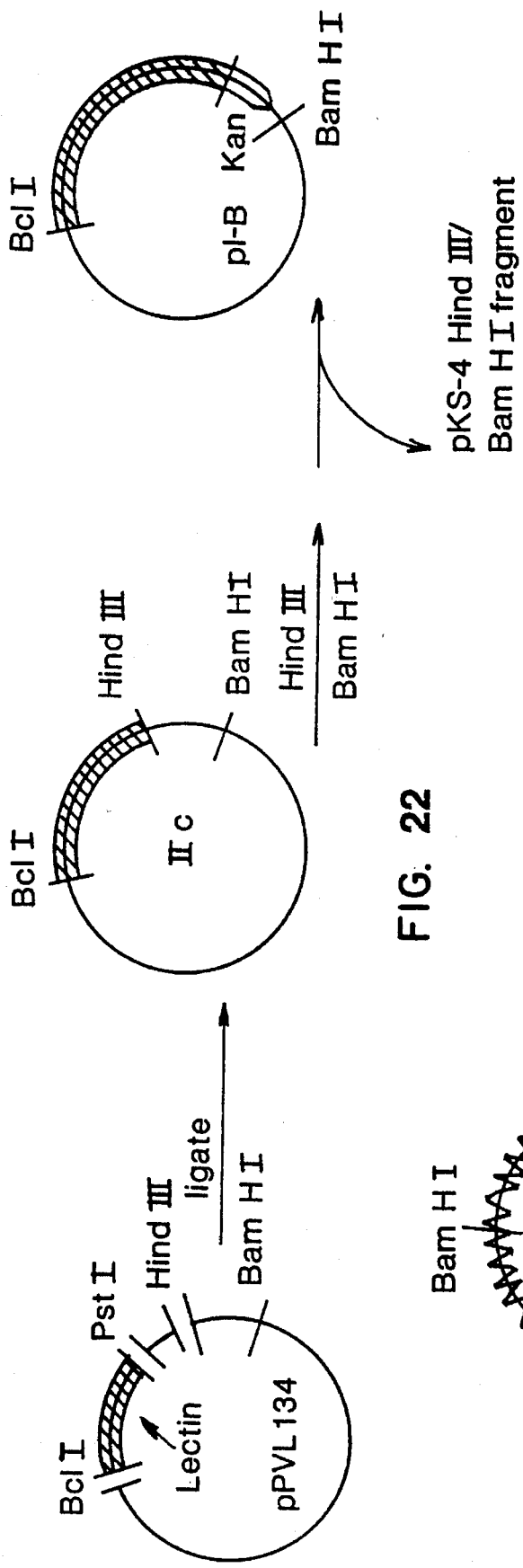
FIG. 22 illustrates the starting plasmids and steps in the construction of pL-B, which comprises the cDNA for a plant lectin. The BclI/PstI fragment of pPVL134 is ligated with BclI/PstI-cut pBR325 vector and linker (see Example 10.1) to yield the plasmid IIc. Then the large replicon- and lectin cDNA-containing HindIII/BamHI fragment of IIc is ligated to the HindIII/BamHI fragment of pKS-4, which fragment comprises the nptII gene.4 and confers kanamycin resistance. Lectin cDNA sequences are indicated by cross-hatching.

10.2 Construction of a Clone Containing Lectin cDNA and a Kanamycin Resistance Gene pPVL134 is digested with BclI and PstI, and the intermediate-sized fragment containing the lectin coding sequence, 3' untranslated region, and a C/G tail is isolated by elution from an agarose gel after separation by electrophoresis. pBR325 is digested with BclI and HindIII and the largest fragment is isolated after sedimentation through a salt gradient. The BclI/HindIII pBR325 vector is mixed with and ligated to the BclI/PstI lectin fragment and the PstI/HindIII linker prepared in Example 10.1. *E. coli* K802 is transformed, selected for drug resistance and presence of lectin sequences, and the plasmid isolated from such cells is labeled IIc. The largest fragment resulting from HindIII and BamHI digestion of IIc is mixed with and ligated to the kanamycin resistance gene-carrying HindIII/BamHI fragment of pKS-4 which is previously isolated by agarose gel electrophoresis (FIG. 22). K802 is transformed, colonies are selected for kanamycin resistance, plasmids are isolated and characterized by restriction mapping. The desired plasmid is labeled pL-B.

Figure 23:
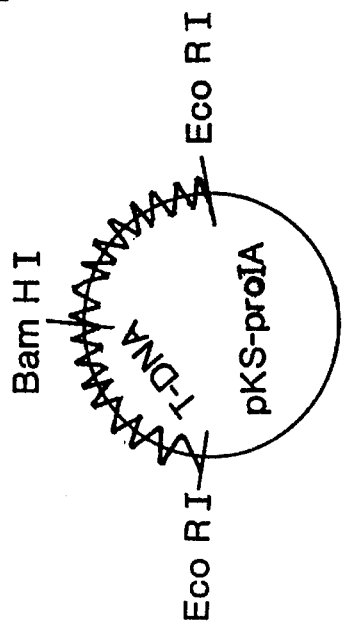
FIG. 23 illustrates a circular restriction map of pKS-proIA. pKS-proI was modified by converting a ClaI site between the promoter of the "1.6 transcript" and the ATG start site of the coding region to a BamHI site. After ClaI digestion, the single-stranded ends were filled in and BamhI linkers were added. The T-DNA insert of the plasmid is indicated by a jagged line.

10.3 Change of a ClaI site to BamHI Site in pKS-proI pKS-proI, whose construction was described in Example 5.1 (see FIG. 12) is digested with ClaI. This cut is located between the promoter and ATG translation start signal of the 1.6 kbp transcript (see FIG. 1). The sticky-ends are converted to blunt-ends by filling in by DNA polymerase I. BamHI linkers are ligated into the gap, trimmed to expose BamHI sticky-ends, ligated, and transformed into K802. Colonies harboring the desired plasmid, pKS-proIA (FIG. 23), are selected after "miniprep" plasmid isolations and a characterization by restriction enzyme mapping.

Figure 24:
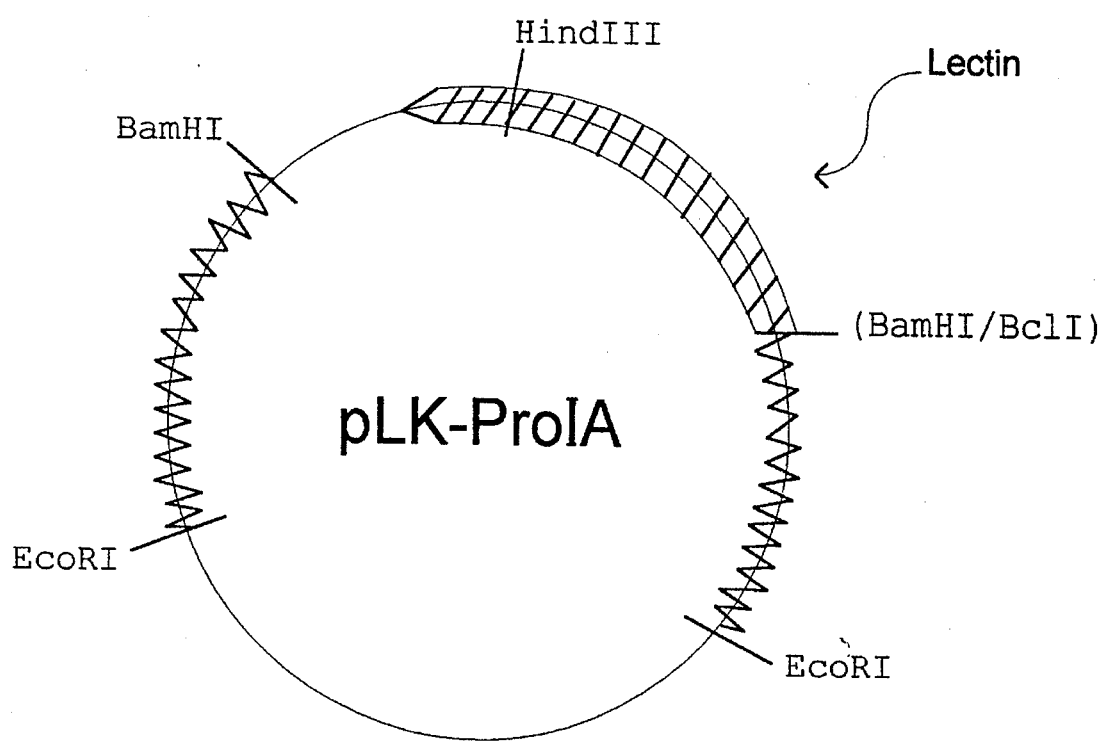
FIG. 24 illustrates a circular restriction map of pLK-proIA. This plasmid was consists of BamHI-linearized pKS-proI ligated with the BclI/BamHI fragment of pL-B carrying the nptII gene and the lectin gene cDNA, which is indicated by cross-hatching.

10.4 Insertion of Lectin and Kanamycin Resistance Genes into pKS-proIA pL-B (Example 10.2) is digested with BclI and BamHI, and the fragment carrying the kanamycin resistance gene and lectin sequences is eluted from an agarose gel after electrophoretic separation. This fragment is mixed with and ligated to BamHI linearized pKS-proIA. The ligation mixture is transformed into K802. Plasmids are isolated from kanamycin resistant colonies, characterized by restriction mapping, and the desired construction labeled pLK-proIA (FIG. 24).

10.5 Expression in Plants pLK-proIA is transferred to a Ti plasmid by a triparental mating (Example 21) of K802(pLK-proIA), *E. coli* (2013), and *A. tumefaciens* (pTi15955) (streptomycin resistant). After additional conjugational transfer of pPH1J1 into the Agrobacterium, double-homologous recombinants are selected by growing cells on kanamycin, streptomycin, and gentamycin. Lectin is detected by ELISA with the appropriate antibodies.

EXAMPLE 11

The purpose of this example is to generate a Ti plasmid with a deletion from the tms ("shooting" locus) through the tmr ("rooting" locus) of pTi15955 and other octopine Ti plasmids. This derivative is useful because cells transformed by it are easier to regenerate to whole plants than cells transformed by pTi15955 with intact tms and tmr genes.

The tms-tmr deleted pTi15955 is ultimately changed in two ways: the inactivation of tms-tmr and the insertion of a foreign gene. Should these two changes be located at different points of the T-DNA, each change is inserted independently by different shuttle vectors. Each shuttle vector dependent change is selected independently which will necessitate use of at least two markers selectable in Agrobacterium. In addition to the usual kanamycin resistance, this example utilized a chloramphenicol resistance gene derived from pBR325.

Figure 25:
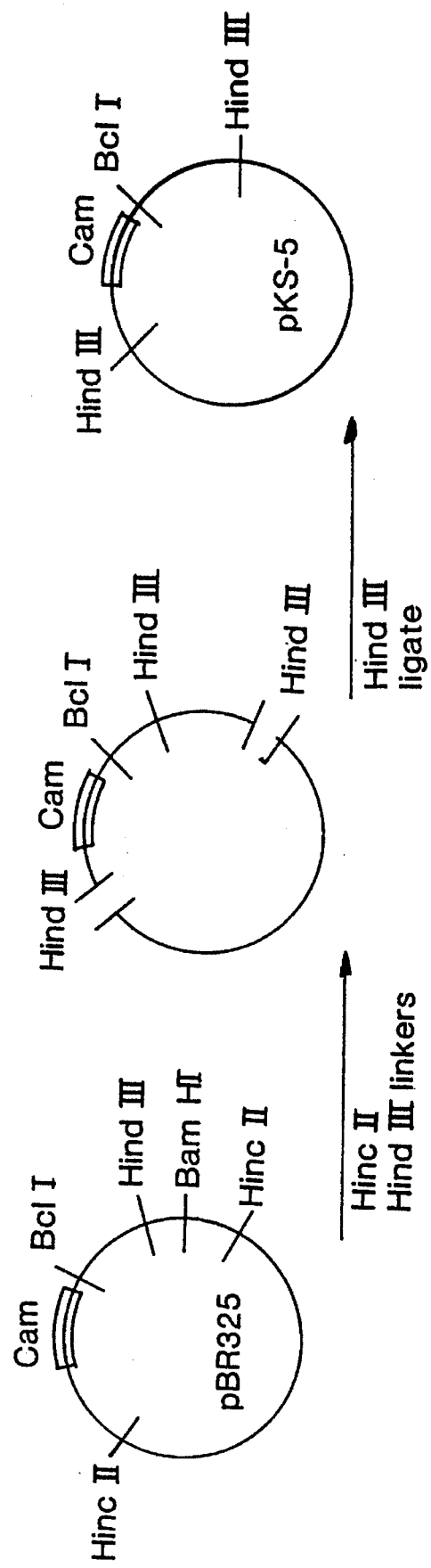
FIG. 25 illustrates the modification of pBR325 by the conversion of a HincII site to a HindIII site by the addition of linkers at the HincII site. The modified plasmid is called pKS-5. The chloramphenicol resistance gene is indicated by an open box and is labeled "cam", and the direction of transcription is indicated by an arrow.

11.1 Construction of a Chloramphenicol Resistance Gene Clone pBR325 is digested with HincII and blunt end ligated with HindIII linkers. The resultant preparation is digested with HindIII, religated, selected for chloramphenicol resistance (cam), and labeled pKS-5 which will serve as a source of the HindIII/BclI fragment which contains the cam gene (FIG. 25).

11.2 Construction of a pBR322 Clone of T-DNA with a Deletion and a Cam Gene

Figure 26:
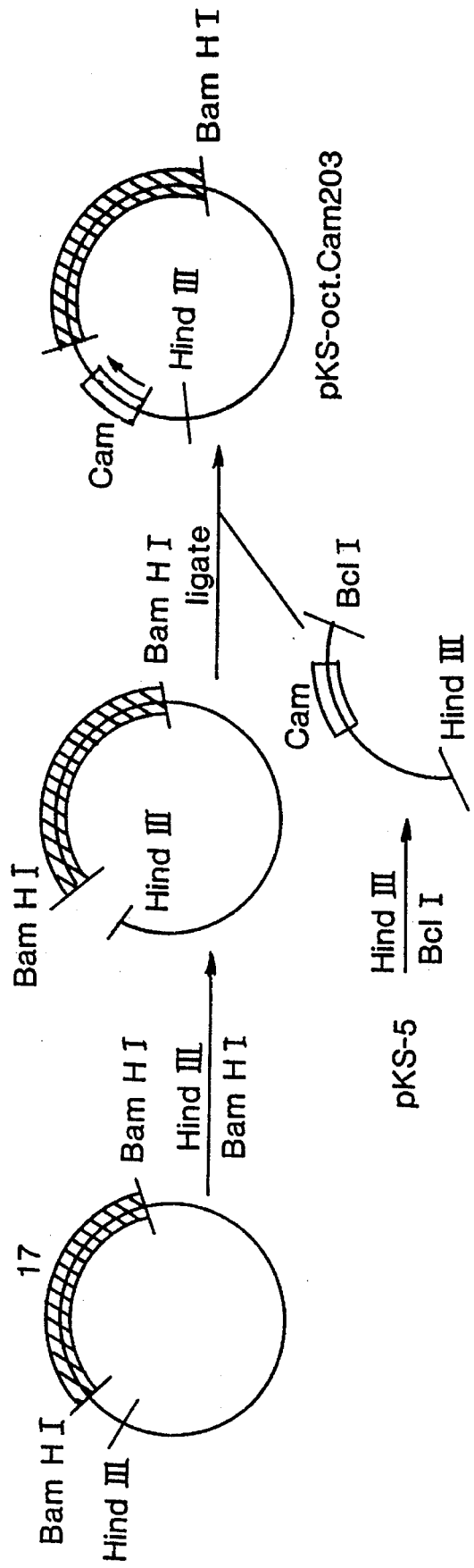
FIG. 26 illustrates the starting material and construction of pKS-oct.Cam203. p203 is completely and partially digested with HindIII and BamHI, respectively, and ligated with the small HindIII/BclI fragment of pKS-5 which carries the chloramphenicol resistance gene. T-DNA sequences are indicated by cross-hatching and the chloramphenicol resistance gene is shown as an open box. The direction of transcription of cam is shown by an arrow.
Figure 27:
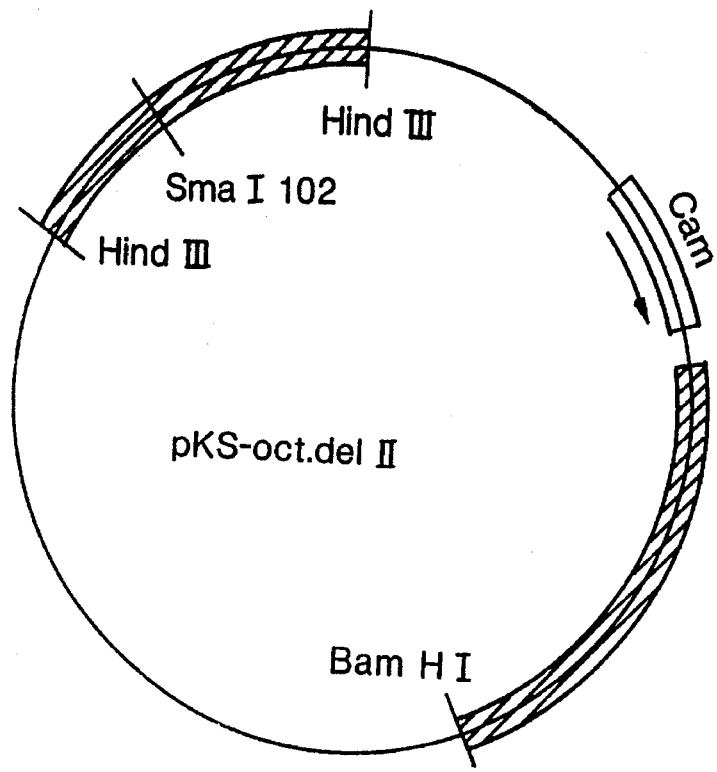
FIG. 27 illustrates a circular restriction map of pKS-oct.delII. pKS-oct.Cam203 was linearized with HindIII and ligated with the 2.2 kbp HindIII fragment from p102. T-DNA sequences are indicated by cross-hatching and the cam gene is indicated by an open box, with an arrow indicating the direction of cam transcription.
Figure 28:
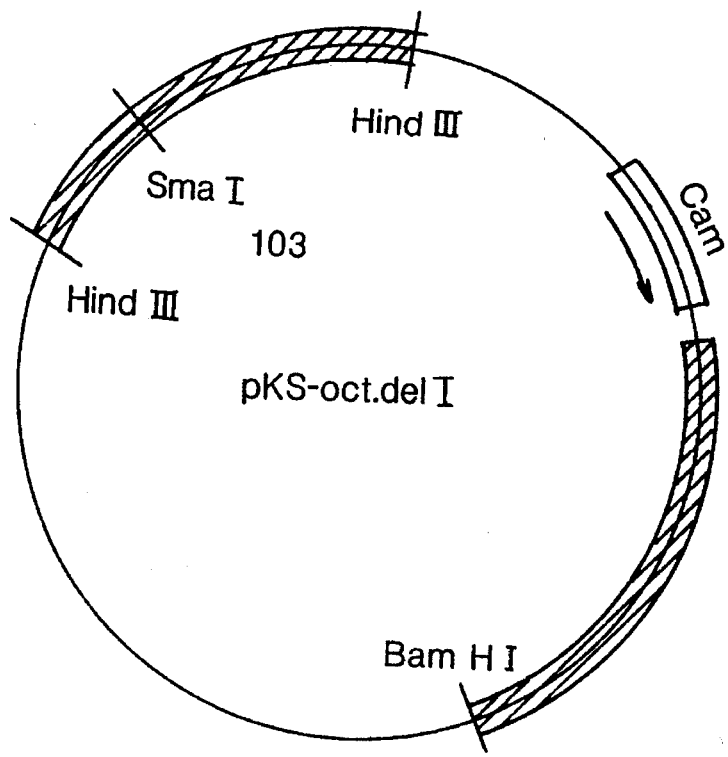
FIG. 28 illustrates a circular restriction map of pKS-oct.delI. pKS-oct.Cam203 was linearized with HindIII and ligated with the 2.0 kbp HindIII fragment from p103. T-DNA sequences are indicated by cross-hatching, and the cam gene is indicated by an open box, with an arrow showing the direction of cam transcription.

A 9.2 kbp linear DNA fragment is isolated from a complete HindIII and partial BamHI digest of p203. The fragment carrying the cam gene is isolated from pKS-5, mixed with the 9.2 kbp linear fragment, ligated, transformed into *E. coli*, selected for chloramphenicol resistance, and labeled pKS-oct Cam203 (FIG. 26).

pKS-oct.Cam203 is a plasmid clone that can now be used to construct a number of TL deletion mutants of pTi15955. It contains the right hand arm of TL and a resistance gene to the left of the right arm. We can attach various left-hand arms of TL to the left of the cam gene (HindIII site). For instance, if p102 is attached the deletion is 5.2 kbp long and includes all of tms and tmr. If p103 is attached the deletion is 3.2 kbp long and includes part of tms and all of tmr. (See FIG. 1.)

pKS-oct.Cam203 is digested with HindIII. p102 or p103 is digested with HindIII and a 2.2 kbp or 2.0 kbp T-DNA fragment, respectively, is isolated and ligated with linearized pKS-oct.Cam203, transformed, and isolated, yielding pKS-oct.delII (FIG. 27) or pKS-oct.delI (FIG. 28), respectively. These constructions are moved into *A. tumefaciens* by mating, homologous recombinations, and selection for chloramphenicol resistance. Alternatively, one moves the constructions into pRK290 by use of established methods by linearizing the construction carrying plasmids with BamHI and ligating into the BglII site of pRK290.

EXAMPLE 12

The Ti plasmid is mutated in this example by deleting the T-DNA between the HpaI site in tmr to the SmaI site in tml. The Ti plasmids that can be modified include pTi15955, pTiB6, pTiA66 and others. This construction is diagrammed in FIG. 29.

12.1 Isolation of the Cam Gene pKS-5 (FIG. 25) is digested with HindIII and BclI. The smallest fragment is isolated after separation on an agarose gel, as taught in Example 11.

12.2 Construction of a pBR322 Clone of T-DNA with a Deletion

Figure 29:
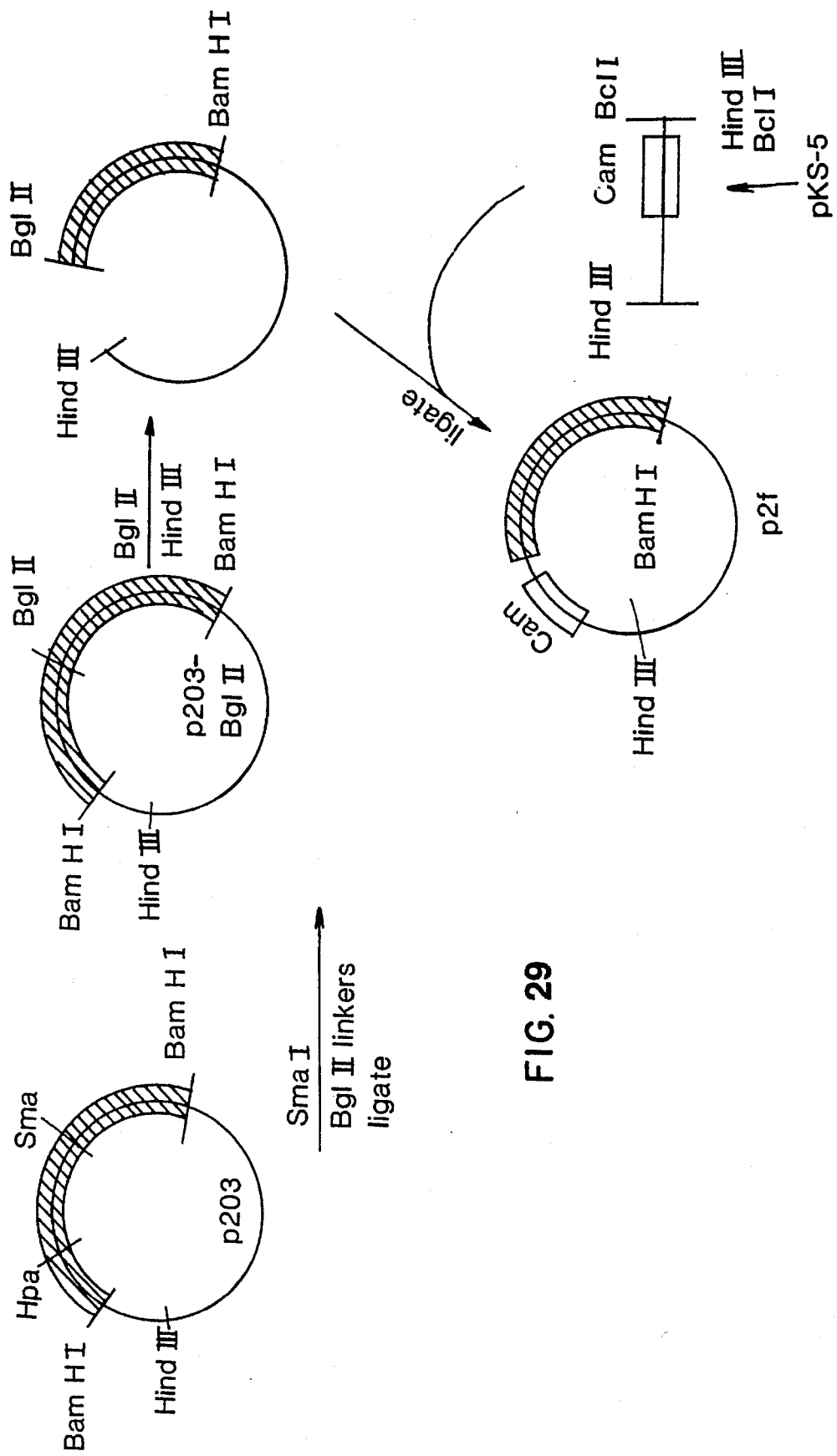
FIG. 29 displays the starting materials and steps for the construction of p2f. p203 was converted to p203BglII by cutting with SmaI, adding BglII linkers, digesting with BglII and ligating. p203-BglII is digested with BglII and HindIII and the large fragment is ligated with the cam-containing BclI/HindIII fragment of pKS-5. T-DNA sequences are indicated by cross-hatching and the cam gene is indicated by an open box.

The right hand arm of the T-DNA deletion is constructed by insertion of BglII sites into the SmaI sites of p203 (see FIG. 1). p203 is digested by SmaI, ligated with BglII linkers, digested with BglII, religated, and transformed into K802. In an alternative construction, BamHI linkers may be substituted for BglII linkers and the appropriate BamHI partial digest products are isolated.) The resultant plasmid is labeled p203-BglII, and is digested with BglII and HindIII. The large BglII/HindIII vector containing fragment is ligated with the chloramphenicol resistance fragment whose isolation was described in Example 12.1. Chloramphenicol resistance is selected for after transformation into K802. The resultant plasmid is labeled p2f (FIG. 29).

12.3 Construction of Left-Hand Arm of T-DNA Deletion Clone

Figure 30:
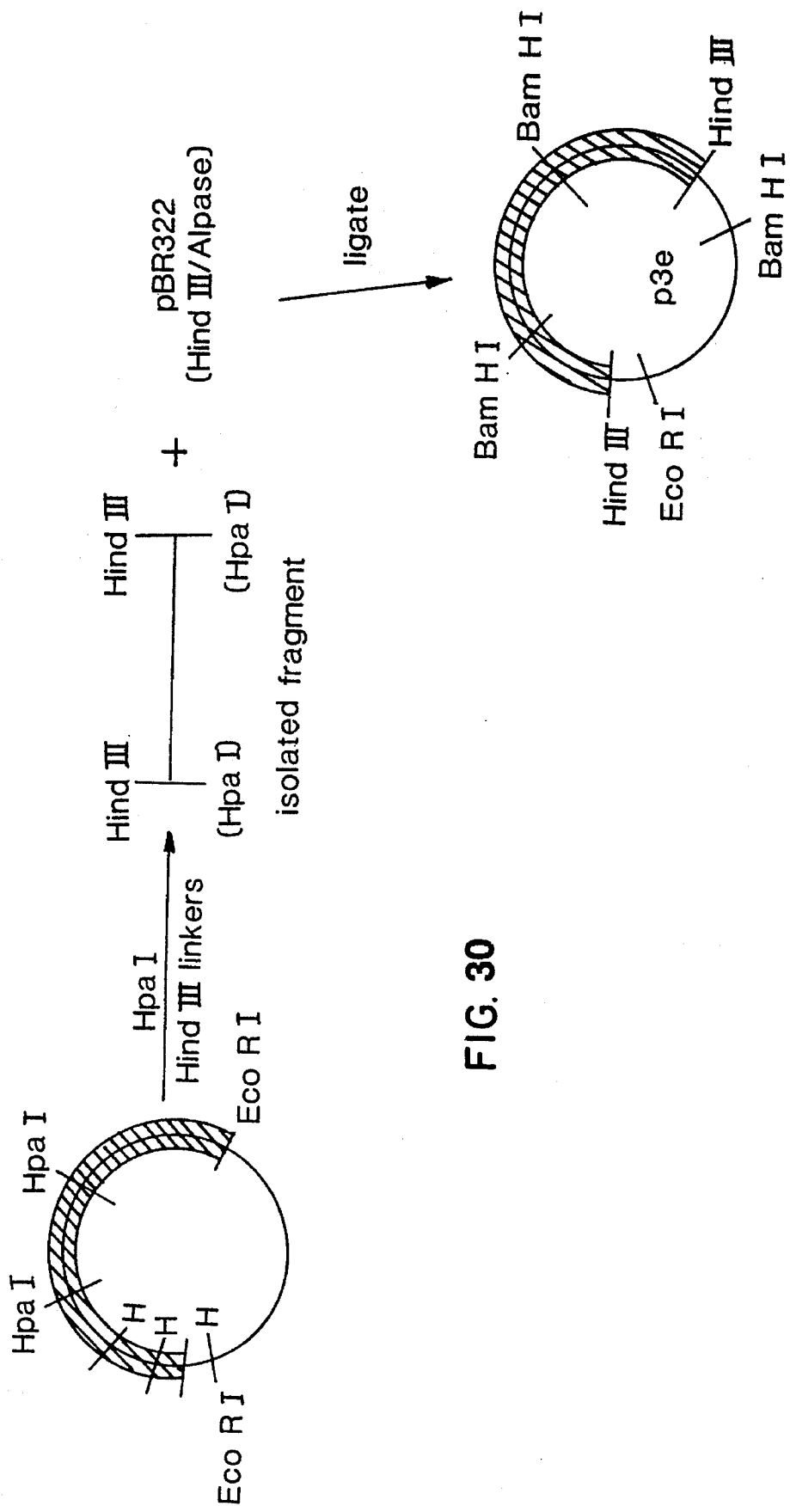
FIG. 30 illustrates the starting materials and steps for the construction of p3e. The HpaI fragment internal to the T-DNA of p202 is converted to a HindIII fragment by digesting with HindIII, adding HpaI linkers, digesting with HpaI. The resultant T-DNA fragment with HindIII ends is then ligated with HindIII-cut, alkaline phosphatase-treated pBR322 to give p3e. T-DNA sequences are indicated by cross-hatching.

HindIII sites are inserted into the HpaI site of p202 by digestion with HpaI and ligation with HindIII linkers. After unmasking of the HindIII sticky ends by digestion with that restriction enzyme, the 2 kbp HpaI fragment which now bears HindIII ends is isolated. The HindIII digested HindIII-ended HpaI fragment is ligated to alkaline phosphatase-treated HindIII-cut pBR322 and transformed into K802. After a colony containing the desired construction is isolated, and characterized, the plasmid is labeled p3e (FIG. 30).

12.4 Construction of the T-DNA Deletion Clone

Figure 31:
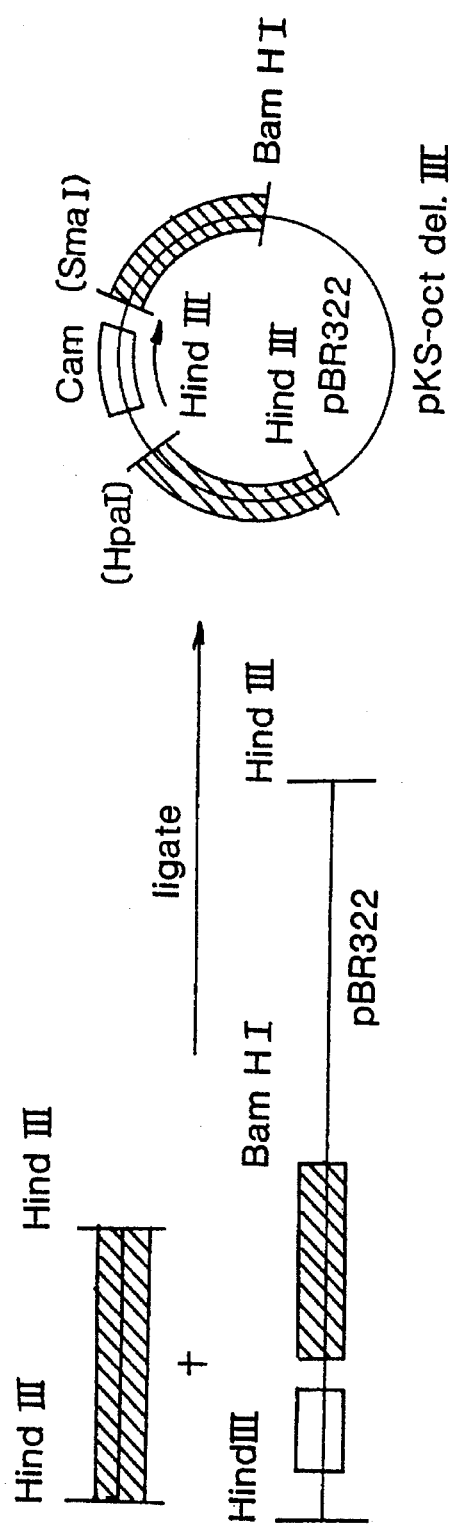
FIG. 31 illustrates the starting materials and steps for the construction of pKS-oct.delIII. The 2 kbp HindIII fragment of p3e is ligated with HindIII-cut p2f (larger component). T-DNA sequences are indicated by cross-hatching and the cam gene is indicated by an open box. The pBR322 sequences are labeled.

The left-hand arm of the clone is obtained by purifying a 2 kbp fragment of a HindIII digest of p3e by elution from an agarose gel after electrophoresis. p2f is cut by HindIII, treated with alkaline phosphatase, mixed with the 2 kbp fragment, ligated, transformed into K802, and selected for chloramphenicol resistance. Plasmids are isolated from individual colonies and characterized by restriction mapping. A plasmid having the two arms in the desired tandem orientation is chosen and labeled pKS-oct.delIII (FIG. 31).

pKS-oct.delIII is moved into *A. tumefaciens* by mating, and homologous recombinants are selected with chloramphenicol. Sunflower and tobacco roots and shoots are inoculated as described in other Examples and the tumors generated are tested for opines.

EXAMPLE 13

This example teaches a construction deleting tmr and tml that provides an alternative to that taught in Example 12.

Figure 32:
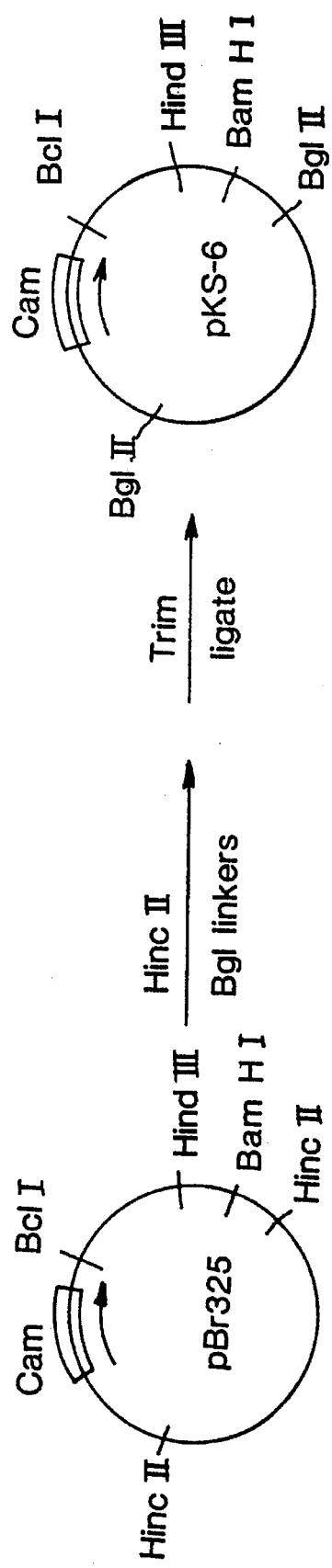
FIG. 32 illustrates the modification of pBR325 by the conversion of a HincII site to a BglII site to give pKS-6. The position and orientation of the cam gene are indicated by an open box and an arrow, respectively.

13.1 Construction of a Chloramphenicol Resistant Fragment with a BglII Site pBR325 is digested with HincII, blunt-end ligated with BglII linkers, digested with BglII, and religated (FIG. 32). Chloramphenicol resistance is selected for after transformation of either K802 or GM33. The resultant plasmid, pKS-6 serves as a source of the BglII/BclI fragment carrying the cam gene.

Figure 33:
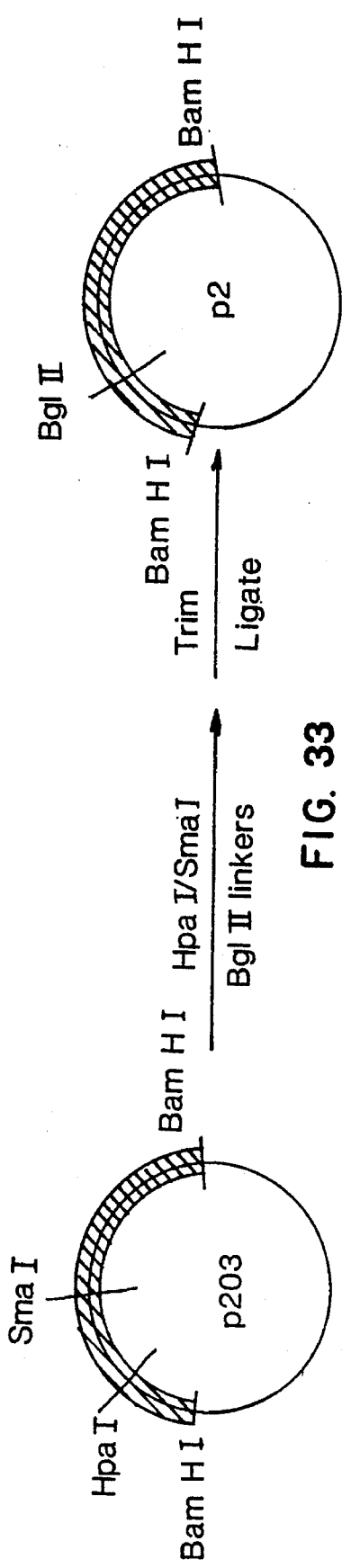
FIG. 33 illustrates the conversion of p203 to p2 by the deletion of the T-DNA internal HpaI/SmaI fragment, the addition of BglII linkers, BglII digestion and ligation.

13.2 Construction of the tmr, tml Deletion Clone p203 is digested with HpaI and SmaI. After blunt end ligation with BglII linkers, it is digested with BglII to expose the BglII sticky-ends, religated, and transformed into K802. The desired construction is identified and labeled p2 (FIG. 33).

13.3 Construction of the T-DNA Deletion Clone (pKS-oct.delIIIa)

Figure 34:
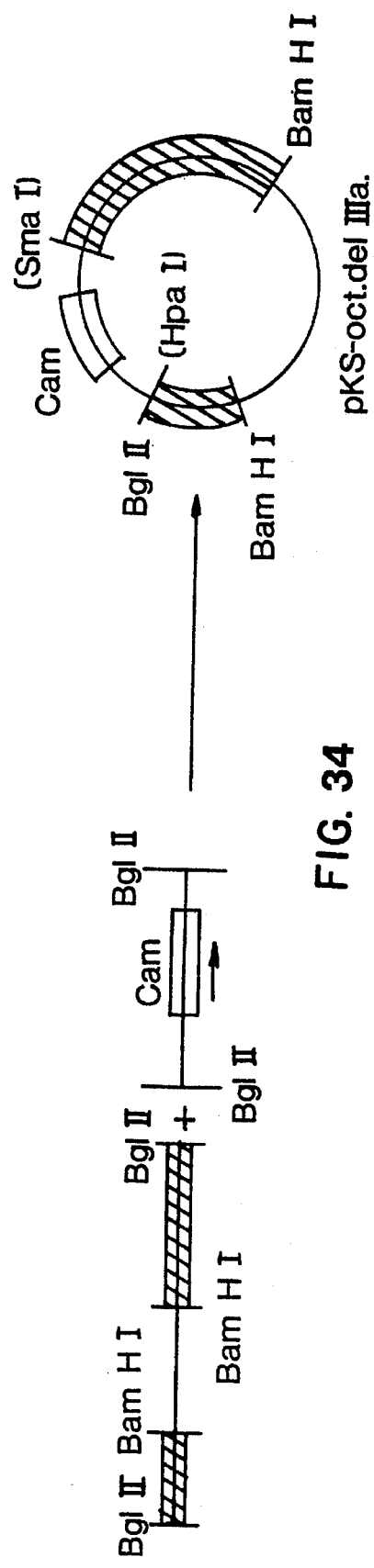
FIG. 34 illustrates the starting materials and construction of pKS-oct.delIIIa. The BglII fragment of pKS-6 comprising the cam gene is ligated with BglII-linearized p2. T-DNA sequences are indicated by cross-hatching and the cam gene is indicated by an open box.

The BglII fragment carrying the Cam gene is isolated from pKS-6 and ligated into BglII-cut p2. Chloramphenicol resistance is selected for after transformation of K802. The resultant plasmid is labeled pKS-oct.delIIIa (FIG. 34), and is tested as described in Example 12.4.

EXAMPLE 14

The purpose of this construction is to provide an example of the mutation of the tmr locus only at the HpaI site by insertion of the chloramphenicol resistance gene. This gene is isolated as the BglII/BclI fragment from pKS-6, and is ligated into the HpaI site of p203 after that site is changed to a BglII site.

14.1 Conversion of the HpaI Site to a BglII Site p203 is digested with HpaI, ligated to BglII linkers, trimmed with BglII and religated. After transformation of K802, colonies are selected and screened by restriction mapping for insertion of BglII sites (FIG. 35).

14.2 Isolation of the Cam Gene pKS-6 is digested with BglII and BclI. The smallest fragment is isolated by agarose gel electrophoresis.

14.3 Construction of the Mutated T-DNA Clone

The modified p203 from Example 14.1 is digested with BglII, ligated with the purified cam gene from Example 14.2 and transformed into K802. Chloramphenicol resistance is selected for, and after isolation from the resistant transformants and characterization by restriction enzyme mapping, the plasmid is labeled pKS-oct.tmr (FIG. 36).

EXAMPLE 15

Regeneration in this example involves carrot tumors incited by an Ri-based TIP plasmid and is effected essentially as described by M. D. Chilton et al. (1982) Nature 295:432–434.

15.1 Infection with Hairy Root

Carrot disks are inoculated with about $10^9$ bacteria in 0.1 ml of water. One to 1.5 cm segments of the ends of the roots obtained are cut off, placed on solid (1–1.5% agar) Monier medium lacking hormones (D. A. Tepfer and J. C. Tempe (1981) C. R. Hebd. Seanc. Acad. Sci., Paris 295:153–156), and grown at 25° C. to 27° C. in the dark. Cultures uncontaminated by bacteria are transferred every 2 to 3 weeks and are subcultured in Monier medium lacking hormones and agar.

15.2 Regeneration of Roots to Plants

The cultured root tissue described in Example 15.1 is placed on solidified (0.8% agar) Monier medium supplemented with 0.36 μM 2,4-D and 0.72 μM kinetin. After 4 weeks, the resulting callus tissue is placed in liquid Monier medium lacking hormones. During incubation at 22° to 25° C. on a shaker (150 r.p.m.) for one month, the callus dissociates into a suspension culture from which embryos differentiate, which, when placed in Petri dishes containing Monier medium lacking hormone, develop into plantlets. Those plantlets are grown in culture, and after exposure to atmospheres of progressively decreasing humidity, are transferred to soil in either a greenhouse or field plot.

15.3 Use of Non-Hairy Root Vectors

Ti-based vectors which do not have functional tmr genes are used instead of the Ri-based vectors as described in Examples 15.1 and 15.2. Construction of suitable deletions is described in Examples 12, 13, and 14.

EXAMPLE 16

Regeneration in this example involves tobacco tumors incited by a Ti- based TIP plasmid and is effected essentially as described by K. A. Barton et al. (1983) supra.

16.1 Infection with Crown Gall

Tobacco tissue is transformed using an approach utilizing inverted stem segments first described by A. C. Braun (1956) Canc. Res. 16:53–56. Stems are surface sterilized with a solution that was 7% commercial Chlorox and 80% ethanol, rinsed with sterile distilled water, cut into 1 cm segments, placed basal end up in Petri dishes containing agar-solidified MS medium (T. Murashige and F. Skoog (1962) Physiol. Plant. 15:473–497) lacking hormones. Inoculation is effected by puncturing the cut basal surface of the stem with a syringe needle and injecting bacteria. Stems are cultured at 25° C. with 16 hours of light per day. The calli which develop are removed from the upper surface of the stem segments, are placed on solidified MS medium containing 0.2 mg/ml carbenicillin and lacking hormones, are transferred to fresh MS-carbenicillin medium three times at intervals of about a month, and are tested to ascertain whether the cultures had been freed of bacteria. The axenic tissues are maintained on solidified MS media lacking supplements under the culture conditions (25° C.; 16 hr.:8 hr. light:dark) described above.

16.2 Culture of Transformed Tissue

Clones are obtained from the transformed axenic tissues as described by A. Binns and F. Meins (1979) Planta 145:365–369. Calli are converted into suspensions of cells by culturing in liquid MS having 0.02 mg/l naphthalene acetic acid (NAA) at 25° C. for 2 or 3 days while being shaken at 135 r.p.m., and filtering in turn through 543 and 213 micron stainless steel meshes. The passed filtrate is concentrated, plated in 5 ml of MS medium containing 0.5% melted agar, 2.0 mg/l NAA, 0.3 mg/l kinetin and 0.4 g/l yeast extract (Difco Laboratories, Inc., Detroit, Mich.) at a density of about $8 \times 10^3$ cells/ml. Colonies reaching a diameter of about 1 mm are picked by scalpel point, placed onto and grown on solidified MS medium having 2.0 mg/l NAA and 0.3 mg/l kinetin. The resulting calli are split into pieces and tested for transformed phenotypes.

16.3 Regeneration of Plants

Transformed clones are placed onto solidified MS medium having 0.3 mg/l kinetin, and cultured as described in Example 16.1. The shoots which form are rooted by putting them on a solid (1.0% agar) medium containing 1/10 strength MS medium salts, 0.4 mg/l thiamine, lacking sucrose and hormones, and having a pH of 7.0. Rooted plantlets are grown in culture, hardened as described in Example 15.2, and are transferred to soil in either a greenhouse or field plot.

16.4 Vectors Used

The methods described in Examples 16.1, 16.2 and 16.3 are suitable Ti-based vectors lacking functional tmr genes. Construction of suitable deletions is described in Examples 12, 13, and 14. These methods are also effective when used with Ri-based vectors. The method described in Example 16.1 for infection of inverted stem segments is often useful for the establishment of TIP transformed plant cell lines.

EXAMPLE 17

The techniques for chemical synthesis of DNA fragments used in these Examples utilize a number of techniques well known to those skilled in the art of DNA synthesis. The modification of nucleosides is described by H. Schaller et al. (1963) J. Amer. Chem. Soc. 8.5:3821–3827. The preparation of deoxynucleoside phosphoramidites is described by S. L. Beaucage and M. H. Caruthers (1981) Tetrahedron Lett. 22:1859. Preparation of solid phase resin is described by S. P. Adams et al. (1983) J. Amer. Chem. Soc. Hybridization procedures useful for the formation of double-stranded synthetic linkers are described by J. J. Rossi et al. (1982) J. Biol. Chem. 257:9226–9229.

EXAMPLE 18

Phaseolin is the most abundant storage protein (approximately 50% of the total seed protein) of *Phaseolis vulgaris*. Transfer of the functional phaseolin gene to alfalfa plants and translation of the phaseolin mRNA into stored phaseolin is of significant economic value since it introduces storage protein into leaf material to be used as fodder. Alfalfa is a valuable plant for the transfer and expression of the phaseolin gene because of its acceptance as cattle fodder, its rapid growth, its ability to fix nitrogen through rhizobial symbiosis, its susceptibility to crown gall infection and the ability to regenerate alfalfa plants from single cells or protoplasts. This example teaches the introduction of an expressible phaseolin gene into intact alfalfa plants.

18.1 Construction of Shuttle Vector

Alfalfa plants are regenerated from crown gall tissue containing genetically engineered Agrobacterium plasmids as described hereafter. In the first step we construct a "shuttle vector" containing a tmr- and a tms-T-DNA mutant linked to a phaseolin structural gene under control of a T-DNA promoter. This construction is, in turn, linked to a nopaline synthase promoter which has a functional neomycin phosphotransferase (NPTII) structural gene (kanamycin resistance) downstream (reported by M. D. Chilton, et al. (18 Jan. 1983) 15th Miami Winter Symposium; see also J. L. Marx (1983) Science 219:830 and R. Horsch et al. (18 Jan. 1983) 15th Miami Winter Symposium). A phaseolin structural gene under control of a T-DNA promoter is illustrated in Example 1.

18.2 Transfer to Agrobacterium and Plant Cells

The "shuttle vector" is then transformed by conventional techniques (Example 21) into a strain of Agrobacterium containing a Ti plasmid such as pTi15955 mutated in one or both of the tmr and tms genes. Bacteria containing recombinant plasmids are selected and co-cultivated with alfalfa protoplasts which later regenerated cell walls (Marton et al. (1979) Nature 277:129–131; G. J. Wullems et al. (1981) Proc. Natl. Acad. Sci. USA 78:4344–4348; and R. B. Horsch and R. T. Fraley (18 Jan. 1983) 15th Miami Winter Symposium).

Cells are grown in culture and the resulting callus tissue is tested for the presence of the appropriate mRNA by Northern blotting (Example 19) and for the presence of the appropriate proteins by ELISA tests (Example 20) (see J. L. Marx (1983) Science 219:830; R. B. Horsch and R. T. Fraley (18 Jan. 1983) 15th Miami Winter Symposium).

18.3 Plant Regeneration

Alfalfa plants are then regenerated from callus tissue by methods similar to those previously used by A. V. P. Dos Santos et al. (1980) Z. Pflanzenphysiol. 99:261–270, T. J. McCoy and E. T. Bingham (1977) Plant Sci. Letters 10:59–66 and K. A. Walker et al. (1979) Plant Sci. Letters 16:23–30. These regenerated plants are then propagated by conventional plant breeding techniques forming the basis for new commercial varieties.

EXAMPLE 19

In all Examples, RNA was extracted, fractionated, and detected by the following procedures.

19.1 RNA Extraction

This procedure was a modification of Silflow et al. (1981) Biochemistry 13:2725–2731. Substitution of LiCl precipitation for CsCl centrifugation was described by Murray et al. (1981) J. Mol. Evol. 17:31–42. Use of 2M LiCl plus 2M urea to precipitate RNA was taken from Rhodes (1975) J. Biol. Chem. 25:8088–8097.

Tissue was homogenized using a polytron or ground glass homogenizer in 4–5 volumes of cold 50 mM Tris-HCl (pH8.0) containing 4% p-amino salicylic acid, 1% tri-isopropyl naphthalene sulfonic acid, 10 mM dithiothreitol (freshly made) and 10 mM Na-metabisulfite (freshly made). N-octanol was used as needed to control foaming. An equal volume of Tris-saturated phenol containing 1% 8-hydroxyquinoline was added to the homogenate which was then shaken to emulsify and centrifuged at 20,000–30,000g for 15 minutes at 4° C. The aqueous upper phase was extracted once with chloroform/octanol (24:1) and centrifuged as above. Concentrated LiCl-urea solution was then added to a final concentration of 2M each and the mixture was left to stand at 20° C. for several hours. The RNA precipitate was then centrifuged down and washed with 2M LiCl to disperse the pellet. The precipitate was then washed with 70% ethanol-0.3M Na-acetate and dissolved in sufficient sterile water to give a clear solution. One half volume of ethanol was added and the mixture put on ice for 1 hour, after which it was centrifuged to remove miscellaneous polysaccharides. The RNA precipitate was then recovered and re-dissolved in water or in sterile no salt poly(U) buffer.

19.2 Poly(U)/Sephadex Chromatography

Two poly(U) Sephadex (trademark: Pharmacia, Inc., Uppsala, Sweden) buffers were used; the first with no salt containing 20 mM Tris, 1 mm EDTA and 0.1% SDS, and the second with 0.1M NaCl added to the first. In order to obtain a good match at A42605, a 2x stock buffer should be made and the salt added to a portion. After adjusting the final concentrations, the buffers were autoclaved.

Poly(U) Sephadex was obtained from Bethesda Research Laboratories and 1 gm poly(U) Sephadex was used per 100 μg expected poly(A)RNA. The poly(U) Sephadex was hydrated in no salt poly-U buffer and poured into a jacketed column. The temperature was raised to 60° C. and the column was washed with no salt buffer until the baseline at 260 nm was flat. Finally the column was equilibrated with the salt containing poly(U) buffer at 40° C. The RNA at a concentration of less than 500 μg/ml was then heated in no salt buffer at 65° C. for 5 minutes, after which it was cooled on ice and NaCl added to a concentration of 0.1M. The RNA was then placed on the column which should be run at no more than 1 ml/min until the optical density has fallen to a steady baseline. The column temperature was then raised to 60° C. and the RNA was eluted with no salt poly(U) buffer. The RNA will usually wash off in three column volumes. The eluted RNA was then concentrated with secondary butanol to a convenient volume after addition of NaCl to 10 mM, and precipitated with 2 volumes ethanol. The ethanol precipitate was dissolved in water and $NH_4$-acetate added to 0.1M, followed by re-precipitation with ethanol. Finally the RNA was redissolved in sterile water and stored at −70° C.

19.3 Formaldehyde RNA Gels

The method used followed that of Thomas (1980) Proc. Natl. Acad. Sci. (USA) 77:5201 and Hoffman, et al. (1981) J. Biol. Chem. 256:2597.

0.75–1.5% agarose gels containing 20 mM Na-phosphate (pH 6.8–7.0) were cast. If high molecular weight aggregate bands appeared, then the experiments were repeated with the addition of 6% or 2.2M formaldehyde (use stock solution of 36%) to the gels. The formaldehyde was added to the agarose after cooling to 65° C. Addition of formaldehyde caused visualization with ethidium bromide to be very difficult. The running buffer was 10 mM Na-phosphate (pH 6.8–7.0).

Prior to electrophoresis, the RNA was treated with a denaturing buffer having final concentrations of 6% formaldehyde, 50% formamide, 20 mM Na-phosphate buffer and 5 mM EDTA. The RNA was incubated in the buffer at 60° C. for 10–20 minutes. The incubation was terminated by addition of stop buffer. For a 20 μl sample, 4 μl 50% glycerol, 10 mM EDTA, 5 mM Na-phosphate and bromphenol blue were added.

Submerged electrophoresis was used. The RNA was loaded before the gel was submerged, and run into the gel at 125 mA for 5 minutes. The gels were then submerged and the current reduced to 30 mA (overnight) or 50 mA (6–8 hours). The buffer was recirculated and the electrophoresis was done in a cold room.

19.4 Northern Blots

If the gel was to be blotted to detect a specific RNA, it was not stained; but a separate marker lane was used for staining. Staining was with 5 ug/ml ethidium bromide in 0.1M Na-acetate and destaining was for several hours in 0.1M Na-acetate. Treatment in water at 60°–70° C. for 5–10 minutes prior to staining helped visualization.

A gel to be blotted was soaked for 15 minutes in 10x standard saline citrate (SSC)-3% formaldehyde. If large RNA molecules were not eluting from the gel then a prior treatment in 50 mM NaOH for 10–30 minutes helped to nick the RNA. If base treatment was used, the gel should be neutralized and soaked in SSC-formaldehyde before blotting. Transfer of the RNA to nitrocellulose was done by standard methods.

Prehybridization was done at 42° C. for a minimum of 4 hours in 50% formamide, 10% dextran sulfate, 5x SSC, 5x Denhardt's, 100 μg/ml denatured carrier DNA, 20 μg/ml poly(A), 40 mM Na-phosphate (pH 6.8–7.0) and 0.2% SDS. Hybridization was done by addition of the probe to the same buffer with overnight incubation. The probe was not used at more than approximately $5\times10^5$ c.p.m./ml.

After hybridization, the nitrocellulose was washed a number of times at 42° C. with 2x SSC, 25 mM Na-phosphate, 5 mM EDTA and 2 mM Na-pyrophosphate followed by a final wash for 20 minutes at 64° C. in 1x SSC. Best results were obtained if the filter was not dried prior to autoradiography and the probe could be removed by extensive washing in 1 mM EDTA at 64° C.

EXAMPLE 20

Western blots, to detect antigens after SDS-polyacryamide gel electrophoresis, were done essentially as described by R. P. Legocki and D. P. S. Verma (1981) Analyt. Biochem. 111:385–392.

Micro-ELISA assays were done using Immulon-2 type plates with 96 wells by the following steps:

20.1 Binding Antibody to Plates

On Day 1, the wells were coated with 1:1000 dilution of antibody (rabbit antiphaseolin IgG) in coating buffer. 200 μl/well was added and then incubated at 37° C. for 2–4 hours after the plates were covered with plastic wrap. Then the plates were rinsed three times with phosphate buffered saline-Tween (PBS-Tween) allowing a 5 minute waiting period between each rinse step. Then 1% bovine serum albumin (BSA) was added to rinse and, after addition to the well, left to sit for 20 minutes before discarding. Rinsing was repeated five times more with PBS-Tween.

20.2 Tissue Homogenization

The tissue was sliced up into small pieces and then homogenized with a polytron using 1 gm of tissue/ml phosphate buffered saline-Tween-2% polyvinyl pyrrolidone-40 (PBS-Tween-2% PVP-40). All samples were kept on ice before and after grinding and standard phaseolin curves were obtained. One standard curve was done in tissue homogenates and one standard curve was also done in buffer to check the recovery of phaseolin when ground in tissue. Following centrifugation of the homogenized samples, 100 microliters of each sample were placed in a well and left overnight at 4° C. To avoid errors, duplicates of each sample were done. The plates were sealed during incubation.

20.3 Binding Enzyme

After the overnight incubation, the antigen was discarded and the wells were washed five times with PBS-Tween allowing 5 minutes between each rinse.

A conjugate (rabbit anti-phaseolin IgG alkaline phosphatase-linked) was the diluted 1:3000 in PBS-Tween-2% PVP containing 0.2%BSA and 150 μl was added to each well; followed by incubation for 3-6 hours at 37° C. After the incubation, the conjugate was discarded and the wells were rinsed five times with PBS-Tween, allowing five minutes between each rinse as before.

20.4 Assay

Immediately before running the assay, a 5mg tablet of p-nitrophenyl phosphate (Sigma Chemical Co., St. Louis, Mo., and stored frozen in the dark) was added per 10 ml substrate and vortexed until the tablet was dissolved. 200 μl of the room temperature solution was quickly added to each well. The reaction was measured at various times, e.g., t=0, 10, 20, 40, 60, 90 and 120 minutes, using a Dynatech micro-ELISA reader. When p-nitrophenyl phosphate, which is colorless, was hydrolysed by alkaline phosphatase to inorganic phosphate and p-nitrophenol, the latter compound gave the solution a yellow color, which could be spectrophotometrically read at 410 nm. The lower limit of detection was less than 0.1 ng.

EXAMPLE 21

Triparental matings were generally accomplished as described below; other variations known to those skilled in the art are also acceptable. *E. coli* K802 (pRK290-based shuttle vector) was mated with *E. coli* (pRK2013) and an *A. tumefaciens* strain resistant to streptomycin. The pRK2013 transferred to the shuttle vector carrying strain and mobilized the shuttle vector for transfer to the Agrobacterium. Growth on a medium containing both streptomycin and the drug to which the shuttle vector confers resistance, often either kanamycin or chloramphenicol, resulted in the selection of Agrobacterium cells containing shuttle vector sequences. A mating of these cells with *E. coli* (pPH1J1) resulted in the transfer of pPH1J1 to the Agrobacterium cells. pPH1J1 and pRK290-based shuttle vectors cannot coexist for long in the same cell. Growth on gentamycin, to which pPH1J1 carries a resistance gene, resulted in selection of cells having lost the pRK290 sequences. The only cells resistant to streptomycin, gentamycin, and either kanamycin or chloramphenicol are those which have Ti plasmids that have undergone double-homologous recombination with the shuttle vector and now carry the desired construction.

TABLE 1

| Plasmid, Bacterium, Strain, Etc. | Made or Used in Example: | Shown in FIG.: | Made Out Of | References, Comments or Synonyms |
|---|---|---|---|---|
| Charon 24A | 6.1 | | | bacteriophage vector based on lambda |
| ColEI | 6.2 | | | |
| GM33 | 13.1 | | | E. coli |
| HB101 | 8.1, 6.1 | | | E. coli |
| K802 | passim | | | E. coli, W. B. Wood (1966) J. Mol. Biol 16:118. |
| pA66-12A | 1.7 | | pTiA66, pKS-OSI-KB3.0 | |
| pBR322 | | 17 | | F. Bolivar, et al. (1978) Gene 2:95–113. |
| pBR322-R | 1.1 | | pBR322 | |
| pBR325 | | 34, 26 | | F. Bolivar (1978) 4:121–136. |
| pcDNA31 | | 22, 15 | pBR322/phas. cDNA | equivalent to pMC6 |
| pCF44A | 2 | 6 | pRK290, pTiC58 | |
| pCF44B | 4.1 | | pCF44A | |
| pCF44C | 4.1 | | pCF448 | |
| pKS-B17-KB3.0 | 1.5 | 43 | pKS4-KB, pKS169 | |
| pKS-KB3.8 | 6.3 | 19 | pBR322, pKS-4, p3.8 | |
| pKSnopIV | 2.2 | 5 | pCF44A, pRK290 | |
| pKSnopV | 4.1 | | pCF44c, pRK290 | |
| pKSnopVI | 4.1 | 9 | pKS-nopV | |
| pKS-oct.Cam203 | 11.2 | 27 | pKS-5, p203 | |
| pKS-oct.delI | 11.2 | 39, 29 | pKS-oct.cam203, p103 | |
| pKS-oct.delII | 11.2 | 39, 28 | pKS-oct.cam203, p102 | |
| pKS-oct.delIII | 12.4 | 33,39 | p2f, p3e | p2f-rt./p3e-ft. |
| pKS-oct.delIIIa | 13.3 | 36 | pKS-6, p2 | |
| pKS-oct.tmr | 14.3 | 39, 38 | pKS-6, p203 | |
| pKS-OS-KB3.0 | 1.6 | | pKS-B17-KB3.0, pRK290 | |
| pKS-proI | 5.1 | 12 | pKS111 | |
| pKS-proIA | 10.3 | 24 | pKS-proI | |
| pKS-proI-KB | 5.4 | 14 | pKS-proI, pKS4-KB | |
| pKS4 | 6.2 | 18 | pBR322, pRZ102 | pKS-4 |
| pKS4-KB2.4 | 7.1 | 21 | pBR322, pKS4, pMC6 | |
| pKS4-KB | 5.2 | 7 | pBR322, pKS4, p7.2 | =pKS4-3.0KB, =pKS4-KB3.0 |
| pKS-KBc | 9 | | pKS4-KB, pMC6 | |
| pKS-5 | 11.1 | 26 | pBR325 | |
| pKS-6 | 13.1 | 34 | pBR325 | |
| pKS111 | 5.1 | 12 | pRK290, p403 | |
| pKS-169 | 1.2 | | pBR322-R, p203 | |
| pL-B | 10.2 | 23 | pKS4, IIc | |
| pLK-proIA | 10.4 | 25 | pKS-proIA, pL-B | |
| pMC6 | 4.5, 9 | 20 | pBR322/phas.cDNA | equivalent to pMC36 |
| pNNN1 | 2.2 | 8 | pKS-nopIV, pKS4-KB | |
| pNNN2 | 4.2, 4.4 | 9 | pKS-nopVI | |
| pNNN4 | 4.4 | | pKS4-KB, pNNN2 | |

TABLE 1-continued

| Plasmid, Bacterium, Strain, Etc. | Made or Used in Example: | Shown in FIG.: | Made Out Of | References, Comments or Synonyms |
|---|---|---|---|---|
| pPH1J1 | 21 | | | used to eliminate shuttle vector, same exclusion group as pRK290, carries gene for resistance to gentamycin. P. R. Hirsh (1973) Thesis, Univ. E. Anglia. |
| pPVL134 | 10.2 | 23 | pBR322/1ec.cDNA | |
| p2 | 13.2 | 35 | p203 | |
| p2f | 12.2 | 31 | pKS5, p203-BglII | |
| p2f-rt./p3e-1ft. | | 39 | | =pKS-oct.delIII |
| p2f-rt./p102-1ft. | | 39 | p2f, p102 | |
| p2f-rt./p103-1ft. | | 39 | p2f, p103 | |
| p3e | 12.3 | 32 | pBR322, p202 | |
| p3.8 | 6.1 | 22, 16 | pBR322, 177.4 | =pJS3.8 |
| p3.8-cDNA | 8.1 | 22 | pcDNA31, p3.8 | |
| p7.2 | 6.1 | 13 | pBR322, 177.4 | =pSS7.2, S. M. Sun, et al. (1981) Nature 289:37–41. |
| p202 | | 32 | pBR322, pTi15955 | |
| p203 | 1, 2, 11, 12, 13, 14 | 31, 35, 42 | pBR322, pTi15955 | |
| p203-BglII | 12.2 | 31 | p203 | |
| p401 | 5 | 1, 11 | pBR322, pTi15955 | |
| p402 | | 1, 11 | pBR322, pTi15955 | |
| p403 | 5 | 1 | pBR322, pTi15955 | |
| 15955-12A | 1.7 | | pTiA66, pKS-OSI-KB3.0 | |
| pRK290 | passim | 30 | | G. Ditta, et at., (1980) Proc. Natl. Acad. Sci. USA 77:7347–7357. |
| pRK2013 | 21 | | | used to mobilize the shuttle vector, carries tra genes that mobilize a mob site on pRK290 for conjugational transfer of pRK290 to Agrobacterium. D. H. Figurski & D. R. Helinski, (1979) Proc. Nat. Acad. Sci. USA 76:1648–1652. |
| pRZ102 | 6.2 | | ColE1, Tn5 | =p7.2; R. A. Jorgenson et al., (1979) Molec. Gen. Genet. 177:65–72. |
| pTiA66 | 1, 5, 12 | | | octopine-type plasmid, pTiA6 with a natural insertion in tms |
| pTiB6 | 12 | | | |
| pTiC58 | 2, 4 | 6 | | nopaline-type plasmid |
| pTi15955 | passim | 1, 11 | | octopine-type plasmid |

TABLE 2

| | |
|---|---|
| NRRL B-15376 | A. tumefaciens/p15955-12A |
| NRRL B-15394 | E. coli C600/pKS4 |
| NRRL B-15392 | E. coli HB101/p3.8 |
| NRRL B-15391 | E. coli HB101/pcDNA31 |
| ATCC 39181 | E. coli HB101/pPVL134 |

We claim:

1. A plant comprising a genetically modified dicot plant cell, which dicot plant cell comprises T-DNA sequences flanking a plant structural gene, which gene is expressed in said plant under the control of a T-DNA promoter, wherein said dicot plant cell comprises T-DNA wherein the tms locus or the tmr locus, or both of said loci, have been inactivated.

2. A plant according to claim 1 wherein the plant structural gene comprises an intron.

3. A plant according to claim 1 wherein the plant structural gene is under control of a promoter selected from the group of T-DNA genes consisting of tmr, tml, tms, nopaline synthase, octopine synthase, and the 1.6 transcript.

4. A plant according to claim 1 wherein the plant structural gene is modified.

5. A plant according to claim 4 wherein the plant structural gene modification comprises removal of an intron.

6. A plant according to claim 4 wherein the plant structural gene comprises cDNA.

7. A plant according to claim 4 wherein the plant structural gene modification comprises a DNA segment insertion.

8. A plant according to claim 4 wherein the plant structural gene modification comprises a DNA segment deletion.

9. A plant according to claim 1 wherein the T-DNA is modified.

10. A plant according to claim 9 wherein the T-DNA modification comprises a mutation in tms.

11. A plant according to claim 9 wherein the modification comprises a mutation in tmr.

12. A plant according to claim 9 wherein the modification comprises a deletion in T-DNA.

13. A plant according to claim 1 wherein the T-DNA promoter includes part of the coding region of the T-DNA gene normally controlled by said promoter.

14. A plant according to claim 13 wherein the plant structural gene comprises an intron.

15. A plant according to claim 13 wherein the plant structural gene codes for phaseolin.

16. A plant according to claim 15 wherein the phaseolin gene is inserted under control of a promoter selected from the group of T-DNA genes consisting of tmr, tml, tms, nopaline synthase, octopine synthase, and the 1.6 transcript.

17. A plant according to claim 16 wherein the plant is a member of the family Compositeae.

18. A plant according to claim 16 wherein the plant is a member of the family Solanaceae.

19. A plant according to claim 16 wherein the plant is a member of the family Leguminoseae.

20. Plant tissue comprising a genetically modified dicot plant cell, which dicot plant cell comprises T-DNA sequences flanking a plant structural gene, which gene is expressed in said plant under the control of a T-DNA promoter, wherein said dicot plant cell comprises T-DNA wherein the tms locus or the tmr locus, or both of said loci, have been inactivated.

21. Plant tissue according to claim 20 wherein the inserted plant structural gene comprises an intron.

22. Plant tissue according to claim 20 wherein the plant structural gene is under control of a promoter selected from the group of T-DNA genes consisting of tmr, tml, tms, nopaline synthase, octopine synthase, and the 1.6 transcript.

23. Plant tissue according to claim 20 wherein the plant structural gene is modified.

24. Plant tissue according to claim 23 wherein the plant structural gene modification comprises removal of an intron.

25. Plant tissue according to claim 23 wherein the plant structural gene comprises cDNA.

26. Plant tissue according to claim 23 wherein the plant structural gene modification comprises a DNA segment insertion.

27. Plant tissue according to claim 23 wherein the plant structural gene modification comprises a DNA segment deletion.

28. Plant tissue according to claim 20 wherein the T-DNA is modified.

29. Plant tissue according to claim 28 wherein the T-DNA modification comprises a mutation in tms.

30. Plant tissue according to claim 28 wherein the T-DNA modification comprises a mutation in tmr.

31. Plant tissue according to claim 28 wherein the T-DNA modification comprises a deletion in T-DNA.

32. Plant tissue according to claim 20 wherein the T-DNA promoter includes part of the coding region of the T-DNA gene normally controlled by said promoter.

33. Plant tissue according to claim 32 wherein the inserted plant structural gene comprises an intron.

34. Plant tissue according to claim 32 wherein the plant structural gene is the gene for phaseolin.

35. Plant tissue according to claim 34 wherein the phaseolin gene is inserted under control of a promoter selected from the group of T-DNA genes consisting of tmr, tml, tms, nopaline synthase, octopine synthase, and the 1.6 transcript.

36. Plant tissue according to claim 35 wherein the plant cell is derived from a member of the family Compositeae.

37. Plant tissue according to claim 35 wherein the plant cell is derived from a member of the family Solanaceae.

38. Plant tissue according to claim 35 wherein the plant cell is derived from a member of the family Leguminoseae.

39. A method for genetically modifying a dicot plant cell, said method comprising:
  (a) providing a DNA vector, said vector comprising Ti plasmid-derived DNA integration functions, and farther comprising a plant structural gene and a T-DNA promoter, said T-DNA promoter and said plant structural gene being in such position and orientation with respect to each other that said plant structural gene is expressible in said plant cell under the control of said T-DNA promoter, and wherein said vector comprises a T-DNA fragment wherein the tms locus or the tmr locus, or both of said loci, have been inactivated; and
  (b) transferring said DNA vector into a dicot plant cell under conditions so that said plant cell is transformed.

40. The method of claim 39 wherein said plant structural gene contains at least one intron.

41. The method of claim 39 wherein said plant structural gene comprises a modified DNA sequence of the naturally-occurring form of a plant structural gene.

42. The method of claim 41 wherein said modification comprises the removal of an intron.

43. The method of claim 41 wherein said plant structural gene comprises cDNA.

44. The method of claim 39 wherein said T-DNA is modified.

45. The method of claim 44 wherein said T-DNA modification comprises a mutation in tms.

46. The method of claim 44 wherein the T-DNA modification comprises a mutation in tmr.

47. The method of claim 39 wherein said T-DNA promoter is a promoter that controls a T-DNA gene selected from the group consisting of tmr, tml, tms, nopaline synthase, octopine synthase, and the 1.6 transcript.

48. The method of claim 47 wherein said T-DNA gene is nopaline synthase.

49. The method of claim 47 wherein said T-DNA gene is octopine synthase.

50. The method of claim 47 wherein said T-DNA gene is the 1.6 transcript.

51. The method of claim 39 wherein said plant structural gene is fused to a T-DNA structural gene under the control of said T-DNA promoter.

52. A dicot plant regenerated from a genetically modified, regenerable dicot plane cell, which plant cell comprises T-DNA sequences flanking a plant structural gene, which gene is expressed in said plant under the control of a T-DNA promoter, wherein said dicot plant cell comprises T-DNA wherein the tms locus or the tmr locus, or both of said loci, have been inactivated.

53. A method for expression of a plant structural gene in a plant, said method comprising:
  (a) genetically modifying a dicot plant cell by providing a T-DNA vector, said vector comprising Ti-plasmid-derived DNA integrations functions, and further comprising a plant structural gene and a T-DNA promoter, said T-DNA promoter and said plant structural gene being in such position and orientation with respect to each other that said plant structural gene is expressible in a dicot plant cell under the control of said T-DNA promoter, and wherein said vector comprises a T-DNA fragment wherein the tms locus or the tmr locus, or both of said loci, have been inactivated; and transferring the T-DNA vector into the dicot plant cell under conditions so that said plant cell is transformed; and (b) regenerating said transformed plant cell to a whole plant wherein said plant structural gene is expressed under the control of said T-DNA promoter.

54. A method for expressing a plant structural gene in a plant tissue, said method comprising:

(a) genetically modifying a dicot plant cell by providing a T-DNA vector, said vector comprising T-DNA Ti-plasmid-derived DNA integration functions, and further comprising a plant structural gong and a T-DNA promoter, said T-DNA promoter and said plant structural gene being in such position and orientation with respect to each other that said plant structural gene is expressible in a plant cell under the control eft said T-DNA promoter, and wherein said vector comprises a T-DNA fragment wherein the tms locus or the tmr locus, or both of said loci, have been inactivated; and (b) allowing proliferation of said transformed plant cell into plant tissue wherein said structural gene is expressed under control of said T-DNA promoter.

55. A transformed whole dicot plant selected from the group consisting of a dicot plant regenerated from a dicot cell transformed to express a heterologous plant structural gene under the control of a T-DNA promoter, said cell containing T-DNA wherein the tms locus or the tmr locus, or both of said loci, have been inactivated; and progeny of said plant.

56. Plant tissue comprising a dicot cell transformed to express a heterologous plant structural gene under the control of a T-DNA promoter, said cell containing T-DNA wherein the tins locus or the tmr locus, or both of said loci have been inactivated.

57. Tissue according to claim 56, wherein said plant tissue is a seed.

58. A method for expressing a plant structural gene in plant tissue, said method comprising providing a dicot cell transformed to express a heterologous plant structural gene under the control of a T-DNA promoter, said cell containing T-DNA wherein the tms locus or the tmr locus, or both of said loci, have been inactivated; and maintaining said cell in conditions where said cell proliferates and said plant structural gene is expressed.

* * * * *

UNITED STATES PATENT AND TRADEMARK OFFICE
CERTIFICATE OF CORRECTION

Page 1 of 7

PATENT NO. : 5,591,605

DATED : January 7, 1997

INVENTOR(S) : Hall *et al.*

It is certified that error appears in the above-identified patent and that said Letters Patent is hereby corrected as shown below:

Cover Page:

[*] Notice: The term of this patent shall not extend beyond the expiration date of Pat. No. 5,102,746. --This should read Pat. No. 5,102,796--

Column 7, line 27: "USA 79.:3193" should read --USA 79:3193-- line 39: "39:729-739," should read --19:729-739,-- line 52: "Plasmid 1:15-29," should read --Plasmid 7:15-29,--

Column 8, line 61: "Plasmid 7:151-154," should read --plasmid 6:151-154,--

Column 20, lines 50-56:

```
                                    EcoRI
...ATG/GGC/CAG/CAA/GG*A/AT T/CTT/TTC    ...
...TAC CCG GTC GTT CC T TA*A GAA AAG    ...
...Met Gly Gln Gln Gly Ile  Leu Phe     ...
   84  85  86  87  88  89   90              Octopine synthase
                       12   13   14 15      phaseolin "
```

UNITED STATES PATENT AND TRADEMARK OFFICE
CERTIFICATE OF CORRECTION

PATENT NO. : 5,591,605

DATED : January 7, 1997

INVENTOR(S) : Hall *et al.*

It is certified that error appears in the above-identified patent and that said Letters Patent is hereby corrected as shown below:

```
should read:
                                EcoRI
...ATG/GGC/CAG/CAA/GG*A/AT T/CTT/TTC...
...TAC CCG GTC GTT CC T TA*A GAA AAG...
...Met Gly Gln Gln Gly  Ile Leu Phe...
    84  85  86  87  88   89  90        octopine synthase
                     12  13  14 15     phaseolin --
```

Column 26, bottom table:

```
  BglII         ClaI         ClaI      SstII      SstII      SstII       BglII
...*   1160bp  *    1300   *    355  *   620  *    420  *    1155bp  *...

*  *XXXXXXXX*XXXXXXX*         *          *               *
                 3' nopaline   5'
                    Synthase
``` should read:

```
  BglII         ClaI         ClaI      SstII      SstII      SstII       BglII
...*   1160bp  *    1300   *    355  *   620  *    420  *    1155bp  *...
   *             *  XXXXXXXX*XXXXXXX*         *          *               *
                    3'  nopaline   5'
                           synthase
```

UNITED STATES PATENT AND TRADEMARK OFFICE
CERTIFICATE OF CORRECTION

PATENT NO. : 5,591,605

DATED : January 7, 1997

INVENTOR(S) : Hall *et al.*

It is certified that error appears in the above-identified patent and that said Letters Patent is hereby corrected as shown below:

Column 27, line 4:

| BgIII | ClaI | | ClaI | SstII | BgIII |
|---|---|---|---|---|---|
| ...* 1160 | * | 1300 | * 355 | * 1155 | *... |
| * | * | XXXXXXXXXXXXX*XXXXXXXXX* | | | * |
| | | 3' nopaline 5' | | | |
| | | synthase | | | | should read:

| BglII | ClaI | | ClaI | SstII | BglII |
|---|---|---|---|---|---|
| ...* 1160 | * | 1300 | * 355 | * 1155 | *... |
| * | * | XXXXXXXXXXXXXX*XXXXXXXXX* | | | * |
| | | 3' nopaline 5' | | | |
| | | synthase | | | |

UNITED STATES PATENT AND TRADEMARK OFFICE
CERTIFICATE OF CORRECTION

Page 4 of 7

PATENT NO. : 5,591,605

DATED : January 7, 1997

INVENTOR(S) : Hall *et al.*

It is certified that error appears in the above-identified patent and that said Letters Patent is hereby corrected as shown below:

Column 27, line 18:

| BglII | | ClaI | | SstII | | BglII |
|---|---|---|---|---|---|---|
| ... * | 1160bp | * | 355 | * | 1155bp | * ... |
| * | | *XXXXXXXXX* | | | | * |
| | | | 5' | | | |

Should read:

| BglII | | ClaI | | SstII | | BglII |
|---|---|---|---|---|---|---|
| ...* | 1160bp | * | 355 | * | 1155bp | *... |
| * | | *XXXXXXXXX* | | | | * |
| | | | 5' | | | |

UNITED STATES PATENT AND TRADEMARK OFFICE
CERTIFICATE OF CORRECTION

PATENT NO.    :   5,591,605

DATED         :   January 7, 1997

INVENTOR(S)   :   Hall *et al.*

It is certified that error appears in the above-identified patent and that said Letters Patent is hereby corrected as shown below:

Column 27, line 34: "5' CGATCCATGG" should read --5' CGATCCAT<u>G</u>G--

Column 27, lines 42&43:

---

```
5'  AGTCTCATACTCACTCTCAATCCAAATAATCTGCCATGGAT         3'  (a
3'      GAGTATGAGTGAGAGTTAGGTTTATTAGAACGGTACCTAGC      5'  (b
```

--- should read:

```
5'  AGTCTCATACTCACTCTCAATCCAAATAATCTGCCATGGAT         3'  (a
3'      GAGTATGAGTGAGAGTTAGGTTTATTAGACGGTACCTAGC      5'  (b
```

Column 33, line 52: "5'...C TCCA G... 3'" should read --5'...C TCCA*G... 3'--

Column 37, line 20: "the Cam gene is" --the cam gene is--

Column 38, line 67: "$8\times10^3$ cells/mi." should read --$8\times10^3$ cells/ml.--

UNITED STATES PATENT AND TRADEMARK OFFICE
CERTIFICATE OF CORRECTION

PATENT NO. : 5,591,605

DATED : January 7, 1997

INVENTOR(S) : Hall *et al.*

It is certified that error appears in the above-identified patent and that said Letters Patent is hereby corrected as shown below:

Column 39, line 33: "J. Amer. Chem. Soc. 8.5:3821-3827." should read --J. Amer. Chem. Soc. 85:3821-3827--.

Column 41, line 8: "1 mm EDTA" should read --1 mM EDTA--

Column 43, line 73: "pNNN2    4.2, 4.4" should read --pNNN2    4.3, 4.4--

Column 44, lines 39&40: "F. Bolivar (1978) 4:121-136." should read --F. Bolivar (1978) Gene 4:121-136.--

Column 46, line 33: "G. Ditta, et at.," should read --G. Ditta, et al.,-- line 43: "transfer ofpRK290    should read --transfer of pRK290 to--

Column 48, line 12: "and farther comprising" should read --and further comprising --

Column 48, line 52: "dicot plane cell" should read --dicot plant cell--

UNITED STATES PATENT AND TRADEMARK OFFICE
CERTIFICATE OF CORRECTION

PATENT NO.  : 5,591,605

DATED       : January 7, 1997

INVENTOR(S) : Hall *et al.*

It is certified that error appears in the above-identified patent and that said Letters Patent is hereby corrected as shown below:

Column 49, line 14: "structural gong and" should read --structural gene and-- line 19: "control eft said" should read --control of said--

Column 50, line 11: "the tins locus" should read --the tms locus--

Signed and Sealed this

Thirtieth Day of September, 1997

*Attest:*

BRUCE LEHMAN

*Attesting Officer*     *Commissioner of Patents and Trademarks*